US012599751B2

(12) United States Patent
Bowes et al.

(10) Patent No.: US 12,599,751 B2
(45) Date of Patent: Apr. 14, 2026

(54) MEDICAL DEVICE STABILIZING SYSTEMS AND METHODS

(71) Applicant: EDWARDS LIFESCIENCES CORPORATION, Irvine, CA (US)

(72) Inventors: Robert Bowes, Trabuco Canyon, CA (US); Russ Hunton, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 449 days.

(21) Appl. No.: 18/173,380

(22) Filed: Feb. 23, 2023

(65) Prior Publication Data

US 2023/0201536 A1 Jun. 29, 2023

Related U.S. Application Data

(63) Continuation of application No. PCT/US2021/048333, filed on Aug. 31, 2021.

(60) Provisional application No. 63/073,392, filed on Sep. 1, 2020.

(51) Int. Cl.
| | |
|---|---|
| *A61M 25/02* | (2006.01) |
| *A61B 17/16* | (2006.01) |
| *A61B 17/29* | (2006.01) |
| *A61B 17/34* | (2006.01) |
| *A61B 90/50* | (2016.01) |
| *A61B 90/57* | (2016.01) |

(52) U.S. Cl.
CPC ......... *A61M 25/02* (2013.01); *A61B 17/1608* (2013.01); *A61B 2017/2946* (2013.01); *A61B 2017/3405* (2013.01); *A61B 2017/3407* (2013.01); *A61B 2090/508* (2016.02); *A61B 2090/571* (2016.02)

(58) Field of Classification Search
None
See application file for complete search history.

(56) References Cited

U.S. PATENT DOCUMENTS

| | | | |
|---|---|---|---|
| 2,876,359 | A | 3/1959 | Langley |
| 3,052,750 | A | 9/1962 | Cobaugh |
| 3,874,388 | A | 4/1975 | King et al. |
| 4,340,091 | A | 7/1982 | Skelton et al. |
| 4,506,669 | A | 3/1985 | Blake, III |
| 4,590,937 | A | 5/1986 | Deniega |

(Continued)

FOREIGN PATENT DOCUMENTS

| | | |
|---|---|---|
| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Michael W Kahelin

(74) *Attorney, Agent, or Firm* — Anya Adams

(57) ABSTRACT

Various stabilizing systems and devices are described for holding and maneuvering medical devices. Some systems and devices include a channel and one or more clamps. The one or more clamps can include one or more of a foot and a movable retaining flange for securing the position of the clamp in the channel.

19 Claims, 49 Drawing Sheets

(56) References Cited

U.S. PATENT DOCUMENTS

| | | | |
|---|---|---|---|
| 4,617,916 A | 10/1986 | LeVahn et al. | |
| 4,693,248 A | 9/1987 | Failla | |
| 4,803,983 A | 2/1989 | Siegel | |
| 5,125,895 A | 6/1992 | Buchbinder et al. | |
| 5,171,252 A | 12/1992 | Friedland | |
| 5,195,962 A | 3/1993 | Martin et al. | |
| 5,292,326 A | 3/1994 | Green et al. | |
| 5,327,905 A | 7/1994 | Avitall | |
| 5,363,861 A | 11/1994 | Edwards et al. | |
| 5,370,685 A | 12/1994 | Stevens | |
| 5,389,077 A | 2/1995 | Melinyshyn et al. | |
| 5,411,552 A | 5/1995 | Andersen et al. | |
| 5,450,860 A | 9/1995 | O'Connor | |
| 5,456,674 A | 10/1995 | Bos et al. | |
| 5,474,057 A | 12/1995 | Makower et al. | |
| 5,478,353 A | 12/1995 | Yoon | |
| 5,487,746 A | 1/1996 | Yu et al. | |
| 5,565,004 A | 10/1996 | Christoudias | |
| 5,607,462 A | 3/1997 | Imran | |
| 5,609,598 A | 3/1997 | Aufer et al. | |
| 5,611,794 A | 3/1997 | Sauer et al. | |
| 5,626,607 A | 5/1997 | Malecki et al. | |
| 5,695,504 A | 12/1997 | Gifford, III et al. | |
| 5,716,417 A | 2/1998 | Girard et al. | |
| 5,727,569 A | 3/1998 | Benetti et al. | |
| 5,741,297 A | 4/1998 | Simon | |
| 5,782,746 A | 7/1998 | Wright | |
| 5,797,960 A | 8/1998 | Stevens et al. | |
| 5,836,311 A | 11/1998 | Borst et al. | |
| 5,843,076 A | 12/1998 | Webster, Jr. et al. | |
| 5,855,590 A | 1/1999 | Malecki et al. | |
| 5,885,271 A | 3/1999 | Hamilton et al. | |
| 5,888,247 A | 3/1999 | Benetti | |
| 5,891,017 A | 4/1999 | Swindle et al. | |
| 5,891,112 A | 4/1999 | Samson | |
| 5,894,843 A | 4/1999 | Benetti et al. | |
| 5,921,979 A | 7/1999 | Kovac et al. | |
| 5,944,738 A | 8/1999 | Amplatz et al. | |
| 5,957,835 A | 9/1999 | Anderson et al. | |
| 5,972,020 A | 10/1999 | Carpentier et al. | |
| 5,980,534 A | 11/1999 | Gimpelson | |
| 6,004,329 A | 12/1999 | Myers et al. | |
| 6,010,531 A | 1/2000 | Donlon et al. | |
| 6,017,358 A | 1/2000 | Yoon et al. | |
| 6,086,600 A | 7/2000 | Kortenbach | |
| 6,120,496 A | 9/2000 | Whayne et al. | |
| 6,132,370 A | 10/2000 | Furnish et al. | |
| 6,162,239 A | 12/2000 | Manhes | |
| 6,165,183 A | 12/2000 | Kuehn et al. | |
| 6,182,664 B1 | 2/2001 | Cosgrove | |
| 6,193,732 B1 | 2/2001 | Frantzen et al. | |
| 6,193,734 B1 | 2/2001 | Bolduc et al. | |
| 6,200,315 B1 | 3/2001 | Gaiser et al. | |
| 6,228,032 B1 | 5/2001 | Eaton et al. | |
| 6,241,743 B1 | 6/2001 | Levin et al. | |
| 6,269,819 B1 | 8/2001 | Oz et al. | |
| 6,269,829 B1 | 8/2001 | Chen et al. | |
| 6,312,447 B1 | 11/2001 | Grimes | |
| 6,461,366 B1 | 10/2002 | Seguin | |
| 6,468,285 B1 | 10/2002 | Hsu et al. | |
| 6,508,806 B1 | 1/2003 | Hoste | |
| 6,508,825 B1 | 1/2003 | Selmon et al. | |
| 6,530,933 B1 | 3/2003 | Yeung et al. | |
| 6,537,290 B2 | 3/2003 | Adams et al. | |
| 6,544,215 B1 | 4/2003 | Bencini et al. | |
| 6,626,930 B1 | 9/2003 | Allen et al. | |
| 6,629,534 B1 | 10/2003 | St. Goar et al. | |
| 6,719,767 B1 | 4/2004 | Kimblad | |
| 6,764,510 B2 | 7/2004 | Vidlund et al. | |
| 6,770,083 B2 | 8/2004 | Seguin | |
| 6,837,867 B2 | 1/2005 | Kortelling | |
| 6,855,137 B2 | 2/2005 | Bon | |
| 6,913,614 B2 | 7/2005 | Marino et al. | |
| 6,939,337 B2 | 9/2005 | Parker et al. | |
| 6,945,956 B2 | 9/2005 | Waldhauser et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,288,097 B2 | 10/2007 | Seguin | |
| 7,371,210 B2 | 5/2008 | Brock et al. | |
| 7,464,712 B2 | 12/2008 | Oz et al. | |
| 7,509,959 B2 | 3/2009 | Oz et al. | |
| 7,569,062 B1 | 8/2009 | Kuehn et al. | |
| 7,618,449 B2 | 11/2009 | Tremulis et al. | |
| 7,682,369 B2 | 3/2010 | Seguin | |
| 7,682,389 B2 | 3/2010 | Beith | |
| 7,731,706 B2 | 6/2010 | Potter | |
| 7,744,609 B2 | 6/2010 | Allen et al. | |
| 7,748,389 B2 | 7/2010 | Salahieh et al. | |
| 7,753,932 B2 | 7/2010 | Gingrich et al. | |
| 7,758,596 B2 | 7/2010 | Oz et al. | |
| 7,780,723 B2 | 8/2010 | Taylor | |
| 7,803,185 B2 | 9/2010 | Gabbay | |
| 7,824,443 B2 | 11/2010 | Salahieh et al. | |
| 7,981,123 B2 | 7/2011 | Seguin | |
| 7,988,724 B2 | 8/2011 | Salahieh et al. | |
| 8,052,750 B2 | 11/2011 | Tuval et al. | |
| 8,070,805 B2 | 12/2011 | Vidlund et al. | |
| 8,096,985 B2 | 1/2012 | Legaspi et al. | |
| 8,104,149 B1 | 1/2012 | McGarity | |
| 8,133,239 B2 | 3/2012 | Oz et al. | |
| 8,147,542 B2 | 4/2012 | Maisano et al. | |
| 8,172,856 B2 | 5/2012 | Eigler et al. | |
| 8,206,437 B2 | 6/2012 | Bonhoeffer et al. | |
| 8,216,301 B2 | 7/2012 | Bonhoeffer et al. | |
| 8,303,653 B2 | 11/2012 | Bonhoeffer et al. | |
| 8,313,525 B2 | 11/2012 | Tuval et al. | |
| 8,348,995 B2 | 1/2013 | Tuval et al. | |
| 8,348,996 B2 | 1/2013 | Tuval et al. | |
| 8,414,643 B2 | 4/2013 | Tuval et al. | |
| 8,425,404 B2 | 4/2013 | Wilson et al. | |
| 8,449,599 B2 | 5/2013 | Chau et al. | |
| 8,449,606 B2 | 5/2013 | Eliasen et al. | |
| 8,460,368 B2 | 6/2013 | Taylor et al. | |
| 8,470,028 B2 | 6/2013 | Thornton et al. | |
| 8,480,730 B2 | 7/2013 | Maurer et al. | |
| 8,540,767 B2 | 9/2013 | Zhang | |
| 8,579,965 B2 | 11/2013 | Bonhoeffer et al. | |
| 8,585,756 B2 | 11/2013 | Bonhoeffer et al. | |
| 8,652,202 B2 | 2/2014 | Alon et al. | |
| 8,668,733 B2 | 3/2014 | Haug et al. | |
| 8,721,665 B2 | 5/2014 | Oz et al. | |
| 8,740,918 B2 | 6/2014 | Seguin | |
| 8,771,347 B2 | 7/2014 | DeBoer et al. | |
| 8,778,017 B2 | 7/2014 | Eliasen et al. | |
| 8,834,564 B2 | 9/2014 | Tuval et al. | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,945,177 B2 | 2/2015 | Dell et al. | |
| 9,034,032 B2 | 5/2015 | McLean et al. | |
| 9,198,757 B2 | 12/2015 | Schroeder et al. | |
| 9,220,507 B1 | 12/2015 | Patel et al. | |
| 9,259,317 B2 | 2/2016 | Wilson et al. | |
| 9,282,972 B1 | 3/2016 | Patel et al. | |
| 9,301,834 B2 | 4/2016 | Tuval et al. | |
| 9,308,360 B2 | 4/2016 | Bishop et al. | |
| 9,387,071 B2 | 7/2016 | Tuval et al. | |
| 9,398,922 B2 * | 7/2016 | Parihar ............. A61B 17/3403 |
| 9,427,327 B2 | 8/2016 | Parrish | |
| 9,439,763 B2 | 9/2016 | Geist et al. | |
| 9,510,837 B2 | 12/2016 | Seguin | |
| 9,510,946 B2 | 12/2016 | Chau et al. | |
| 9,572,660 B2 | 2/2017 | Braido et al. | |
| 9,642,704 B2 | 5/2017 | Tuval et al. | |
| 9,700,445 B2 | 7/2017 | Martin et al. | |
| 9,775,963 B2 | 10/2017 | Miller | |
| D809,139 S | 1/2018 | Marsot et al. | |
| 9,889,002 B2 | 2/2018 | Bonhoeffer et al. | |
| 9,949,824 B2 | 4/2018 | Bonhoeffer et al. | |
| 10,076,327 B2 | 9/2018 | Ellis et al. | |
| 10,076,415 B1 | 9/2018 | Metchik et al. | |
| 10,099,050 B2 | 10/2018 | Chen et al. | |
| 10,105,221 B2 | 10/2018 | Siegel | |

(56) References Cited

U.S. PATENT DOCUMENTS

| | | | |
|---|---|---|---|
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Entz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2006/0241745 A1 | 10/2006 | Solem |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0188869 A1 | 8/2008 | Weitzner et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0247942 A1 | 10/2009 | Kirschenman |
| 2009/0270677 A1 | 10/2009 | Dillon |
| 2009/0275902 A1 | 11/2009 | Heeps et al. |
| 2009/0287304 A1 | 11/2009 | Dahlgren et al. |
| 2009/0319037 A1 | 12/2009 | Rowe et al. |
| 2010/0010475 A1 | 1/2010 | Teirstein et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0117281 A1 | 5/2010 | Doyle |
| 2010/0121434 A1 | 5/2010 | Paul et al. |
| 2010/0249497 A1 | 9/2010 | Peine et al. |
| 2010/0286478 A1 | 11/2010 | Ewers et al. |
| 2010/0298929 A1 | 11/2010 | Thornton et al. |
| 2010/0324595 A1 | 12/2010 | Linder et al. |
| 2011/0015490 A1 | 1/2011 | Trovato et al. |
| 2011/0082538 A1 | 4/2011 | Dahlgren et al. |
| 2011/0130718 A1 | 6/2011 | Kidd et al. |
| 2011/0137410 A1 | 6/2011 | Hacohen |
| 2011/0152609 A1 | 6/2011 | Trusty et al. |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0004502 A1 | 1/2012 | Weitzner et al. |
| 2012/0022633 A1 | 1/2012 | Olson et al. |
| 2012/0078355 A1 | 3/2012 | Zipory et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2012/0330411 A1 | 12/2012 | Gross et al. |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |

(56) References Cited

U.S. PATENT DOCUMENTS

| | | |
|---|---|---|
| 2014/0142695 A1 | 5/2014 | Gross et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243963 A1 | 8/2014 | Sheps et al. |
| 2014/0243968 A1 | 8/2014 | Padala |
| 2014/0249546 A1 | 9/2014 | Shvartsberg et al. |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0112427 A1 | 4/2015 | Schweich, Jr. et al. |
| 2015/0142100 A1 | 5/2015 | Morriss et al. |
| 2015/0148896 A1 | 5/2015 | Karapetian et al. |
| 2015/0157268 A1 | 6/2015 | Winshtein et al. |
| 2015/0190201 A1 | 7/2015 | Olson |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0272734 A1 | 10/2015 | Sheps et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0092661 A1 | 4/2018 | Prabhu |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2018/0368928 A1 | 12/2018 | Abedinnasab |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0269477 A1 | 9/2019 | Schaub |
| 2019/0314155 A1 | 10/2019 | Franklin et al. |
| 2020/0108225 A1* | 4/2020 | Jamal .................... A61F 2/2427 |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0023664 A1* | 1/2021 | Plöckl .................. B23Q 9/0085 |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |

(56) References Cited

U.S. PATENT DOCUMENTS

| | | | |
|---|---|---|---|
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0313433 A1 | 10/2022 | Ma et al. |
| 2023/0014540 A1 | 1/2023 | Metchik et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| JP | 2008513057 A | 5/2008 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue-3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

Noune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Janurary 3,1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue-3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskulare Chirurgie, Band 15, Heft 2, Stuttgart, im Apr. 1967, pp. 199-203.

(56) References Cited

OTHER PUBLICATIONS

Praz et al., "Compassionate use of the PASCAL transcatheter mitral valve repair system for patients with severe mitral regurgitation: a multicentre, prospective, observational, first-in-man study," The Lancet, vol. 390, Issue 10096, pp. 773-780, Aug. 19, 2017, Lancet, United States.

Reul RM et al., "Mitral valve reconstruction for mitral insufficiency", Prog Cardiovasc Dis., vol. 39, Issue-6, May-Jun. 1997.

Rosch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10. No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña JP et al., Bow-tie 'mitral valve repair: an adjuvant technique for ischemic mitral regurgitation', Ann Thorac Surg., vol. 66, Issue-6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

Wheatley, David J., "Valve Prosthesis", Rob & Smith's Operative Surgery- Cardiac Surgery, vol. 91, No. 2, pp. 115-424, Feb. 1, 1987, Butterworth Scientific, London, UK.

* cited by examiner

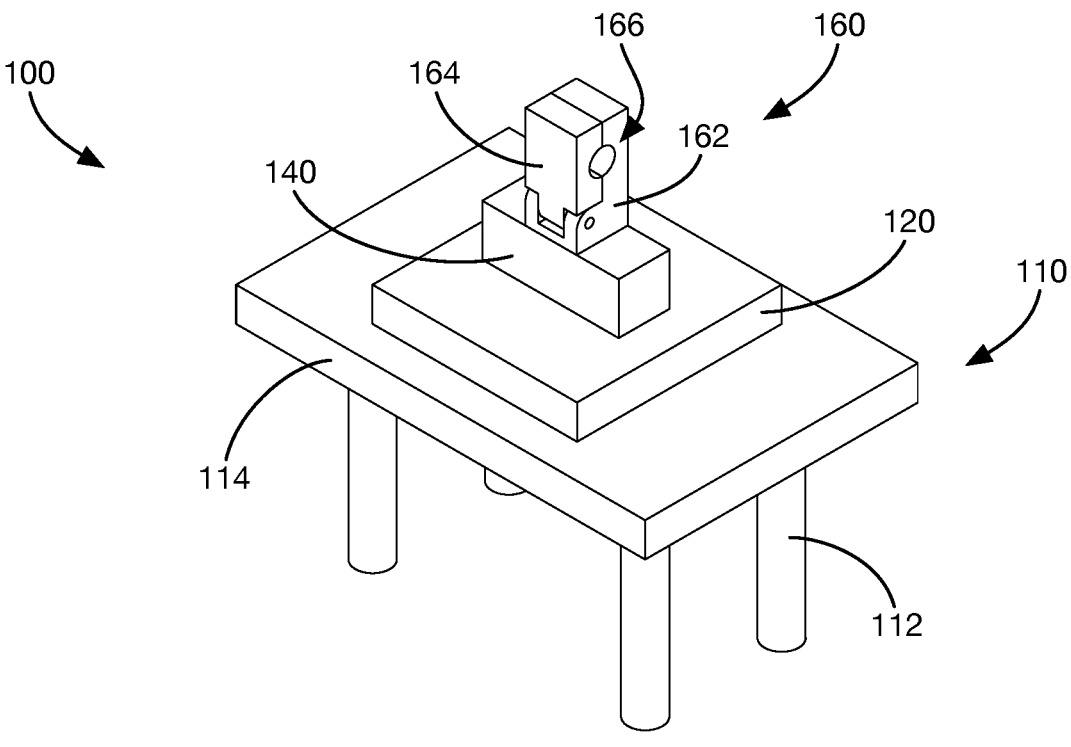
FIG. 1
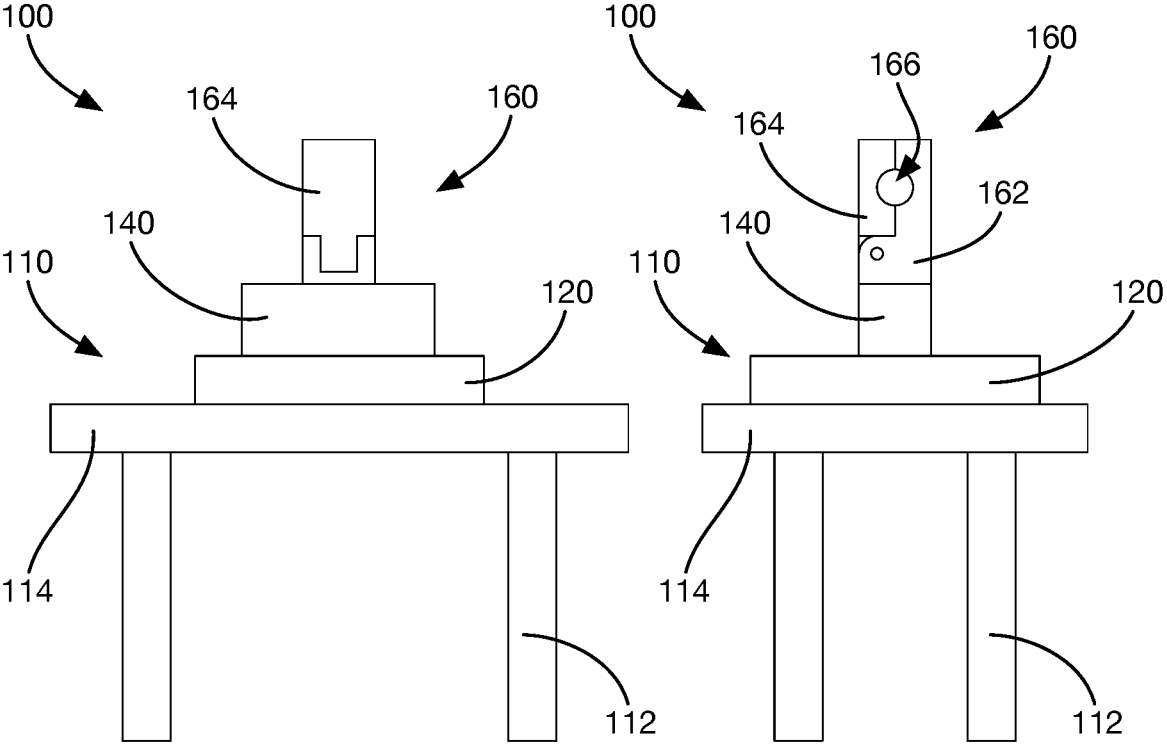
FIG. 2          FIG. 3

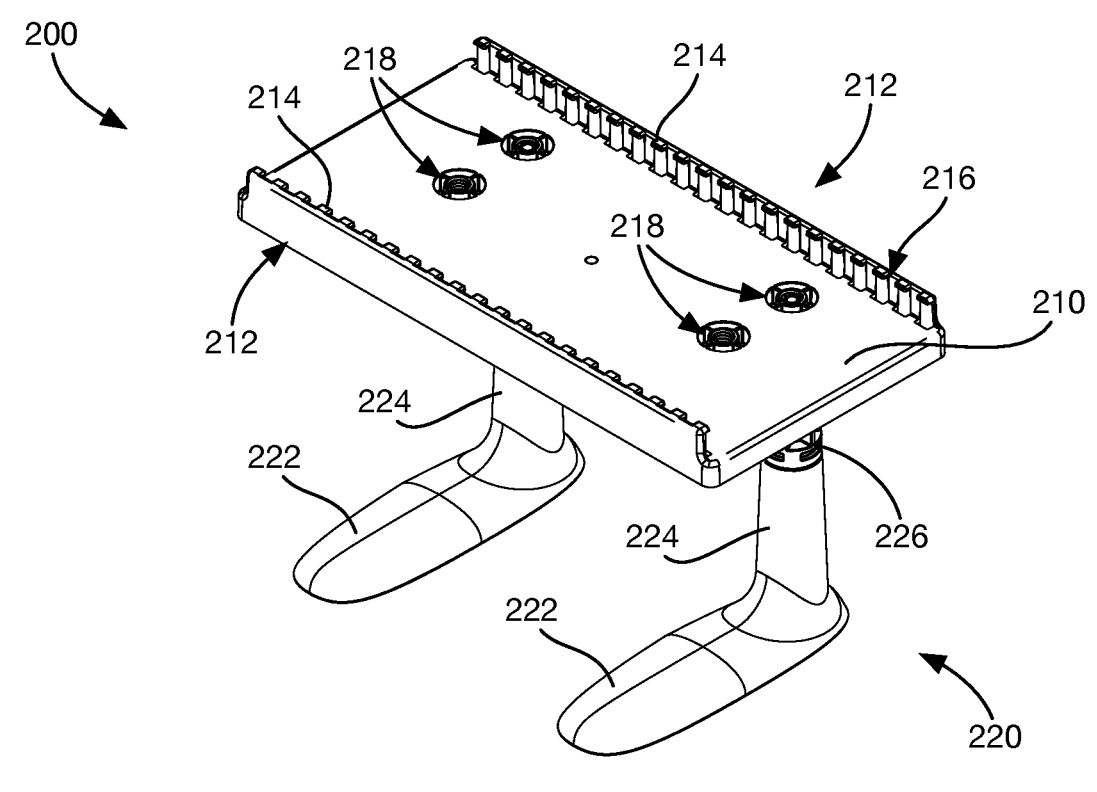
FIG. 10
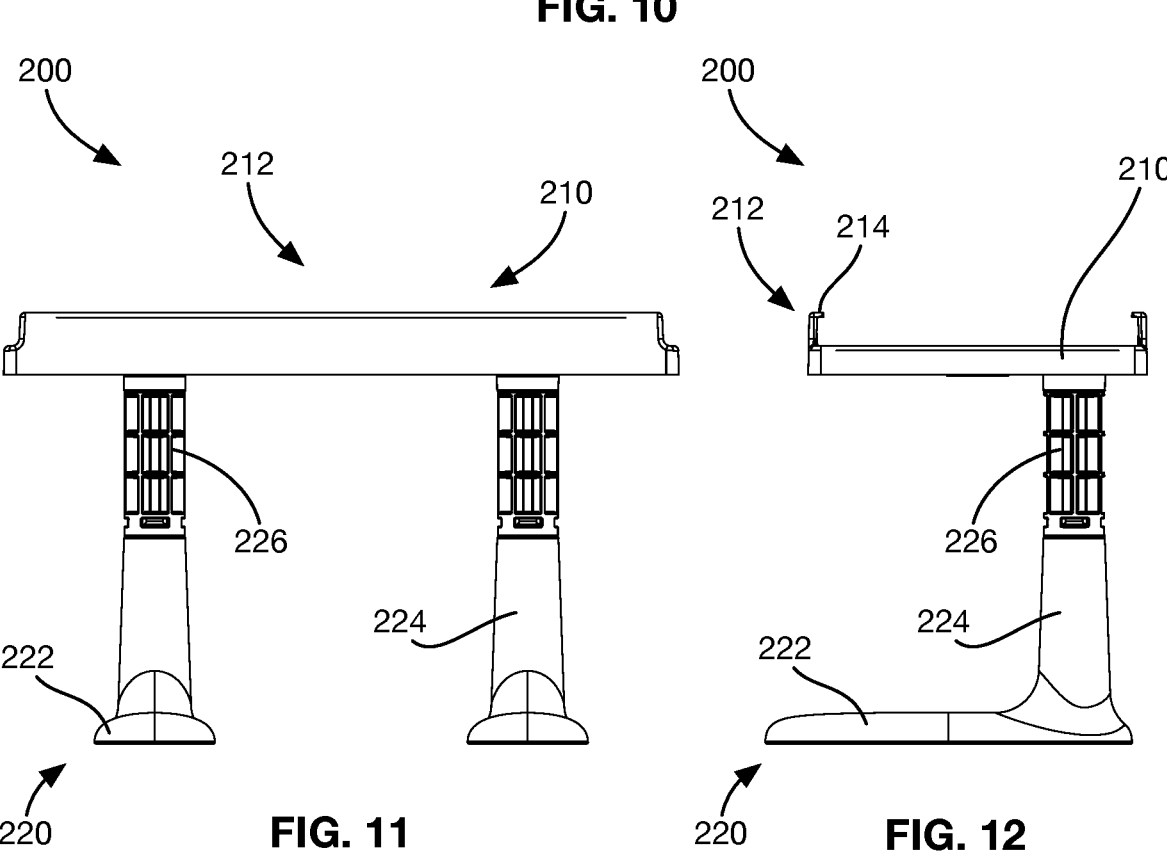
FIG. 11            FIG. 12

340

350

342          344

340

350

342          344

340

356          350

344

346          348

340

342          344

356          356

346

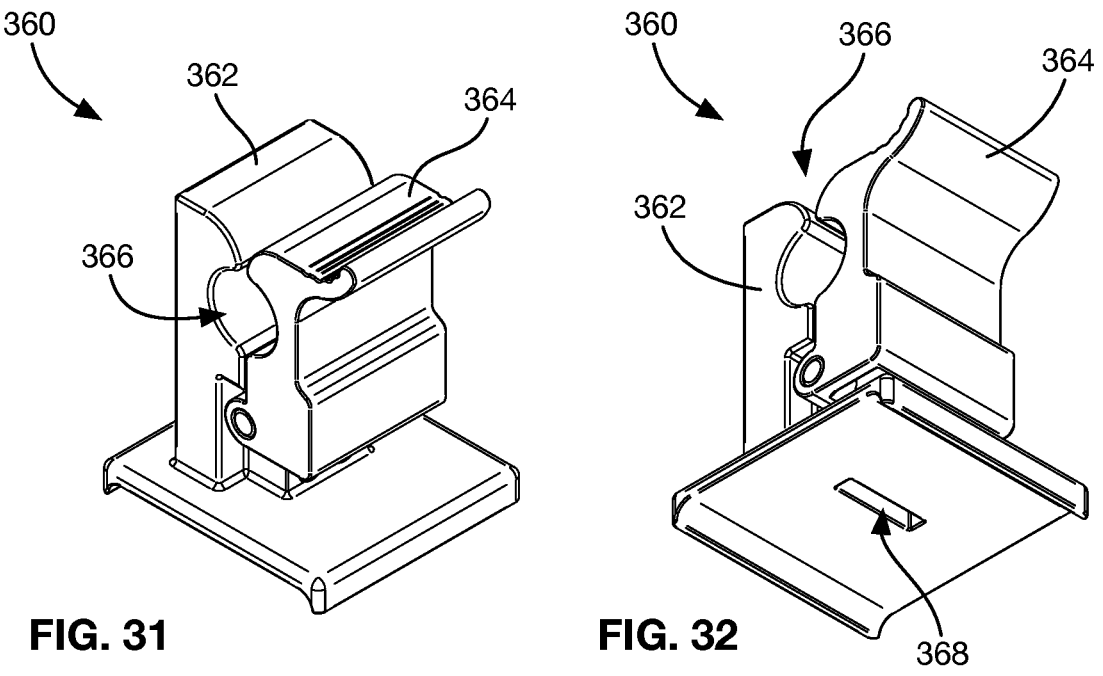
FIG. 31
FIG. 32
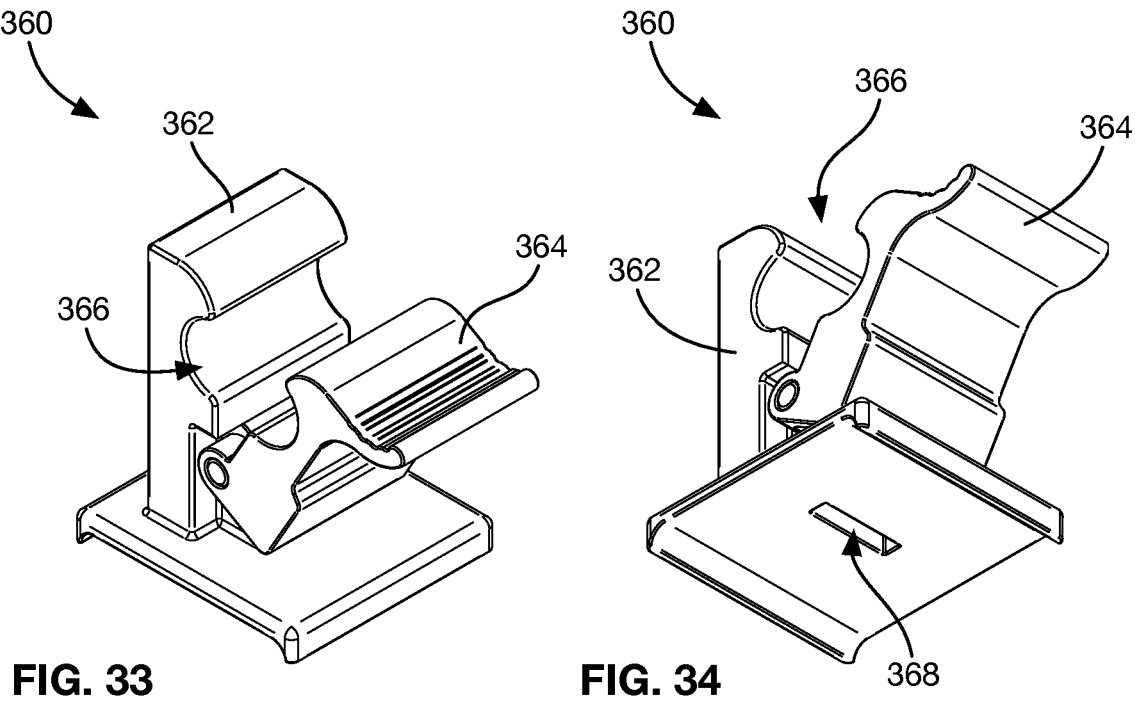
FIG. 33
FIG. 34

560

560

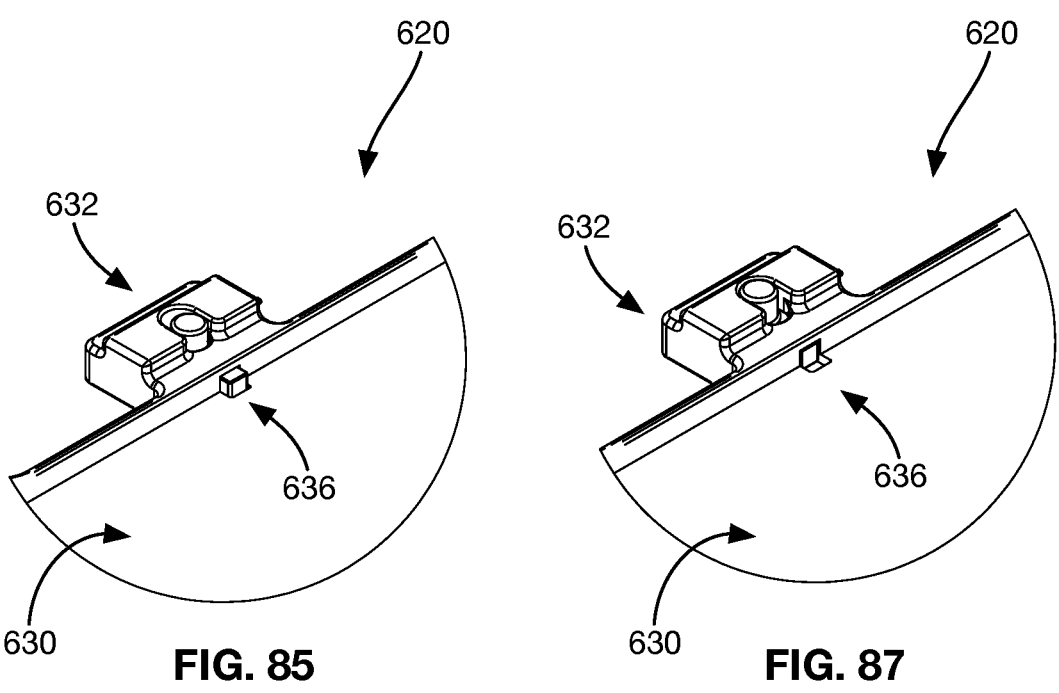
FIG. 85
FIG. 87
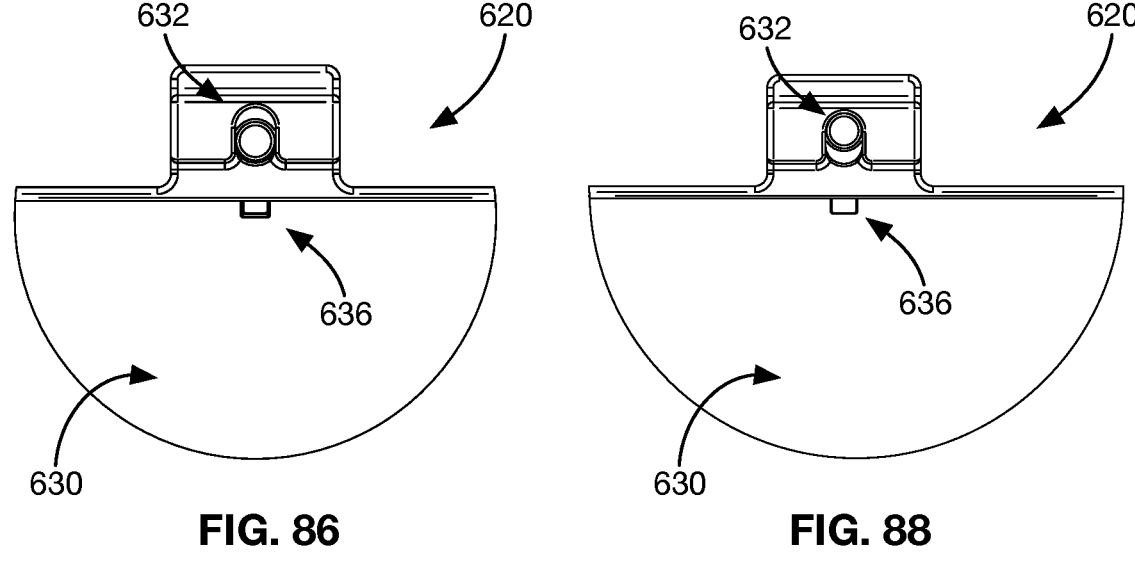
FIG. 86
FIG. 88

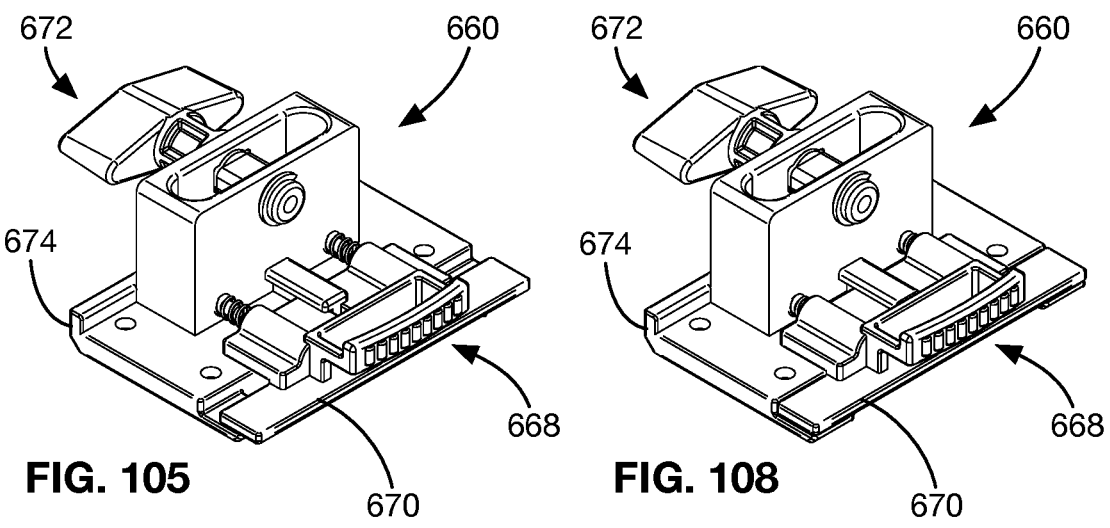
FIG. 105
FIG. 108
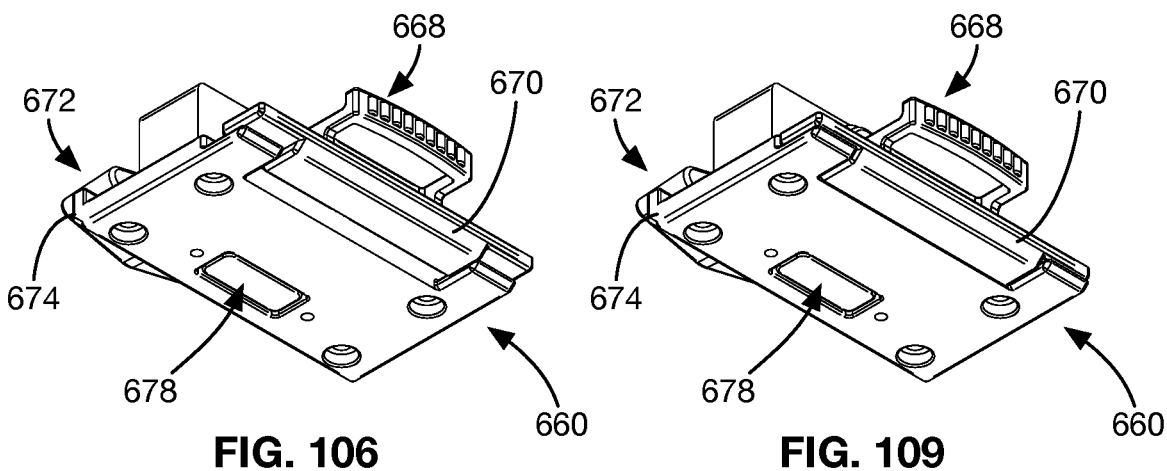
FIG. 106
FIG. 109
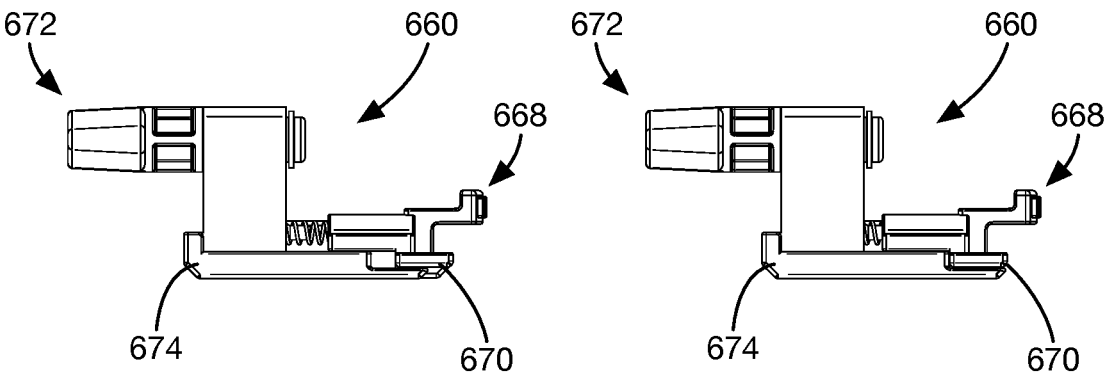
FIG. 107
FIG. 110

MEDICAL DEVICE STABILIZING SYSTEMS AND METHODS

RELATED APPLICATION

The present application is a continuation of Patent Cooperation Treaty Application No. PCT/US2021/048333, filed on Aug. 31, 2021, which claims the benefit of U.S. provisional patent application No. 63/073,392 filed Sep. 1, 2020, which is incorporated herein by reference in its entirety for all purposes.

BACKGROUND

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, for example, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present. Tricuspid regurgitation can be similar, but on the right side of the heart.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In some implementations, stabilizing apparatuses, devices, and systems are described for holding and maneuvering medical devices. Some apparatuses include one or more of a base plate, a carriage, and a clamp, or a combination of some or all of these. The base plate can be attached to one or more tables. The carriage can be moveably attached to the base plate or can be integrally formed with the base plate. The carriage can receive one or more clamps. The one or more clamps can be moveably attached to the carriage or the base and configured to receive one or more medical devices.

In some implementations, an example stabilizing system or device for holding a medical device comprises an integrally formed base plate portion and carriage portion having a clamp mounting channel. The stabilizing system/device includes one or more clamps for receiving the medical device. The one or more clamps are slidably disposable in the clamp mounting channel.

In some implementations, the clamp includes a foot (e.g., an extension) configured to engage the channel to lock the position of the clamp in the channel.

In some implementations, the channel comprises a first mounting rail and a second mounting rail.

In some implementations, the clamp includes a fixed mounting flange and a movable mounting flange.

In some implementations, the fixed mounting flange and the movable mounting flange are disposable in recesses in the first mounting rail and the second mounting rail.

In some implementations, an actuator (e.g., a button, knob, latch, lever, etc.) is actuatable to retract the movable mounting flange.

In some implementations, the movable mounting flange is biased away from the fixed mounting flange.

In some implementations, an actuator (e.g., a button, knob, latch, lever, etc.) is actuatable to move the foot into engagement with the channel.

In some implementations, the clamp includes a cam configured to move the foot into engagement with the channel.

In some implementations, the foot is biased to a retracted position.

In some implementations, the clamp comprises a fixed jaw and a movable jaw that is biased in a closing direction toward the fixed jaw.

In some implementations, the clamp further comprises an actuator (e.g., a button, knob, latch, lever, etc.) that can be actuated or moved into an engaged condition where the clamp is partially opened to facilitate the rotation of the medical device within the clamp.

In some implementations, an example stabilizing system for holding a medical device comprises an integrally formed base plate portion and carriage portion having a clamp mounting channel and at least one clamp for receiving the medical device, wherein the clamp is slidably disposable in the clamp mounting channel.

In some implementations, the clamp includes a foot configured to engage the channel to lock the position of the clamp relative to the channel.

In some implementations, the system includes a table comprising a platform. In some implementations, the platform can comprise side walls for receiving first and second retaining tabs of the base plate portion.

In some implementations, the table includes one or more legs (e.g., a plurality of legs) for supporting the platform.

In some implementations the channel comprises a first mounting rail and a second mounting rail.

In some implementations, the clamp includes a fixed mounting flange and a movable mounting flange.

In some implementations, the fixed mounting flange and the movable mounting flange are disposed in recesses in the first mounting rail and the second mounting rail.

In some implementations, an actuator (e.g., a latch button, etc.) is configured to retract the movable mounting flange.

In some implementations, the movable mounting flange is biased away from the fixed mounting flange.

In some implementations, a locking knob is configured to move the foot into engagement with the channel.

In some implementations, the clamp includes a cam configured to move the foot into engagement with the channel.

In some implementations, the foot is biased to a retracted position.

In some implementations, the clamp comprises a fixed jaw and a movable jaw that is biased in a closing direction toward the fixed jaw.

In some implementations, the clamp further comprises a free rotate lever that can be moved into an engaged condition where the clamp is partially opened to facilitate the rotation of the medical device within the clamp.

In some implementations, an example stabilizing apparatus or stabilizing device for one or more medical devices includes a base plate and a clamp. The base plate has a channel. The clamp is slidably disposable in the channel.

In some implementations, the clamp includes a foot that is configured to engage the channel to lock the position of the clamp relative to the base plate.

In some implementations, the channel includes a first mounting rail and a second mounting rail.

In some implementations, the clamp includes a fixed mounting flange and a movable mounting flange.

In some implementations, the fixed mounting flange and the movable mounting flange are disposed in recesses in the first mounting rail and the second mounting rail.

In some implementations, a latch button retracts the movable mounting flange.

In some implementations, the movable mounting flange is biased away from the fixed mounting flange.

In some implementations, a locking knob is configured to move the foot into engagement with the channel.

In some implementations, a cam is configured to move the foot into engagement with the channel.

In some implementations, the foot is biased to a retracted position.

In some implementations, the clamp comprises a fixed jaw and a movable jaw that is biased in a closing direction toward the fixed jaw.

In some implementations, the clamp includes a free rotate lever that can be moved into an engaged condition where the clamp is partially opened to facilitate the rotation of the medical device within the clamp.

In some implementations, the stabilizing device is used in a stabilizing system that includes a table. The table includes a platform and a plurality of legs. In some implementations, the platform can include side walls for receiving first and second retaining tabs of the base plate.

In some implementation, an example stabilizing apparatus, device, or system comprises a base plate, a carriage, and at least one clamp for receiving one or more medical devices. At least one of the base plate and the carriage includes at least one rail.

In some implementations, the at least one clamp is attachable to the at least one rail such that the at least one clamp can slide along the rail but is prevented from detaching from the rail.

In some implementations, the base plate includes the at least one rail, and the carriage is moveably attachable to the at least one rail of the base plate such that it is prohibited from moving away from the base plate by the at least one rail.

In some implementations, the at least one rail comprises a plurality of locking teeth for engaging a latch member of at least one of the carriage and the at least one clamp.

In some implementations, at least one of a release button, knob, and/or lever is actuatable to enable the carriage and/or the at least one clamp to move laterally along the at least one rail.

In some implementations, the base plate comprises two mounting rails, and the carriage comprises fixed and movable retaining lips for securing the carriage between the two mounting rails.

In some implementations, the carriage comprises an adjustment mechanism for moving (e.g., sliding) the at least one clamp laterally along the carriage (e.g., along a channel or at least one rail of the carriage).

In some implementations, actuating a button, knob, and/or lever of the at least one clamp disengages the at least one clamp from the adjustment mechanism of the carriage.

In some implementations, the adjustment mechanism comprises a worm drive that engages a pin of a traveler for attaching the clamp.

In some implementations, the clamp further comprises at least one of release button, knob, and/or lever for disengaging the clamp from the adjustment mechanism.

In some implementations, the carriage comprises a first mounting rail and a second mounting rail.

In some implementations, the clamp includes a fixed mounting flange and a movable mounting flange.

In some implementations, the fixed mounting flange and the movable mounting flange are disposable in recesses in the first mounting rail and the second mounting rail.

In some implementations, an example stabilizing apparatus or stabilizing system for one or more medical devices includes a base plate, a carriage, and one or more clamps.

In some implementations, the base plate and carriage can be separate components that are attachable to each other.

In some implementations, the base plate and carriage integrally formed. In some implementations, the carriage can be a channel formed in or on the base plate (e.g., which can be the same as or similar to other channels described herein).

In some implementations, the base plate has at least one rail extending upward. In some implementations, the carriage can be moveably attached to the at least one rail of the base plate and can be prohibited from moving away from the base plate by the at least one rail.

The one or more clamps are configured to receive one or more medical devices.

In some implementations, the one or more clamps can each be moveably (e.g., slidably) attached to the carriage. The one or more clamps can be configured to be removable from or attachable to the carriage by the end user.

In some implementations, the at least one rail of the base plate includes a plurality of locking teeth for engaging a latch member of the carriage.

In some implementations, the at least one rail of the base plate is received within a mounting channel of the carriage.

In some implementations, depressing a release button of the carriage enables the carriage to move laterally along the at least one rail.

In some implementations, depressing the release button of the carriage enables the carriage to be removed from the at least one rail.

In some implementations, the base plate includes two mounting rails, and the carriage includes fixed and movable retaining lips for securing the carriage between the two mounting rails.

In some implementations, the carriage further includes an adjustment mechanism for moving the clamp laterally along the carriage.

In some implementations, depressing a release button of the clamp disengages the clamp from the adjustment mechanism of the carriage.

In some implementations, the adjustment mechanism includes a worm drive that engages a pin of a traveler for attaching the clamp.

In some implementations, the clamp further includes a release lever for disengaging the clamp from the adjustment mechanism.

In some implementations, the release lever can be retained in a released condition.

In some implementations, the clamp comprises a fixed jaw and a movable jaw that is biased in a closing direction toward the fixed jaw.

In some implementations, the clamp includes a free rotate lever that can be moved into an engaged condition where the clamp is partially opened to facilitate the rotation of the medical device within the clamp.

In some implementations, the stabilizing apparatus is used in a stabilizing system.

In some implementations, the stabilizing system includes a table. In some implementations, the table includes a platform and one or more legs (e.g., a plurality of legs).

In some implementations, the platform includes side walls for receiving first and second retaining tabs of the base plate.

In some implementations, an example stabilizing system for holding a medical device comprises a clamp mounting channel defined by first and second mounting rails, and a clamp for receiving the medical device. The clamp is slidably disposable (e.g., positionable) in the clamp mounting channel.

In some implementations, the clamp includes a foot that engages the channel to lock the position of the clamp in the channel.

In some implementations, the channel comprises a gripping strip for engaging the locking foot.

In some implementations, the clamp includes a fixed mounting flange and a movable mounting flange.

In some implementations, the fixed mounting flange and the movable mounting flange are disposable in recesses in the first mounting rail and the second mounting rail.

In some implementations, an actuator (e.g., a button, knob, latch, lever, etc.) is actuatable to retract the movable mounting flange.

In some implementations, the movable mounting flange is biased away from the fixed mounting flange.

In some implementations, an actuator (e.g., a button, knob, latch, lever, etc. is actuatable to move the foot into engagement with the channel.

In some implementations, the system includes a cam for moving the foot into engagement with the channel. In some implementations, the foot is biased to a retracted position.

In some implementations, the clamp comprises a fixed jaw and a movable jaw that is biased in a closing direction toward the fixed jaw.

In some implementations, the clamp further comprises an actuator (e.g., a button, knob, latch, lever, etc.) that can be actuated or moved into an engaged condition where the clamp is partially opened to facilitate the rotation of the medical device within the clamp.

In some implementations, an example clamp for holding a medical device comprises a fixed jaw and a movable jaw. In some implementations, the movable jaw is opened and closed by pivoting the movable jaw relative to the fixed jaw.

In some implementations, a movable retaining flange extends from a first side of the clamp. In some implementations, a fixed retaining flange extending from a second side of the clamp that is opposite the first side.

In some implementations, a movable locking foot extending from a bottom of the clamp.

In some implementations, the movable retaining flange includes a beveled edge.

In some implementations, an actuator (e.g., a button, knob, latch, lever, etc.) is actuatable to retract the movable retaining flange.

In some implementations, the movable retaining flange is biased away from the fixed retaining flange.

In some implementations, an actuator (e.g., button, knob, latch, lever, etc.) is actuatable to move the foot into engagement with the channel.

In some implementations, the clamp comprises a cam for moving the foot into engagement with the channel. In some implementations, the foot is biased to a retracted position.

In some implementations, the clamp further comprises an actuator (e.g., a button, knob, latch, or lever) that can be actuated or moved into an engaged condition where the clamp is partially opened to facilitate the rotation of the medical device within the clamp.

In some implementations, an example clamp mounting channel of a stabilizing system comprises a first mounting rail and a second mounting rail. The first mounting rail and the second mounting rail are configured to receive a clamp for holding a medical device, such that the clamp is slidably disposable in the clamp mounting channel between the first mounting rail and the second mounting rail, and such that a foot of the clamp can engage the clamp mounting channel to lock the position of the clamp in the clamp mounting channel.

In some implementations, the channel comprises a gripping strip for engaging the locking foot.

In some implementations, the channel comprises recesses in the first mounting rail and the second mounting rail, wherein the recesses are configured to receive at least one of a first flange and a second flange of the clamp.

In some implementations, the recesses include top surfaces configured to engage the first flange and the second flange of the clamp when the locking foot presses down on the bottom of the clamp mounting channel such that the position of the clamp in the clamp mounting channel is locked.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of examples of the present disclosure, a more particular description of the certain examples will be made by reference to various aspects of the appended drawings. It is appreciated that these drawings depict only typical examples of the present disclosure and are therefore not to be considered limiting of the scope of the disclosure. Moreover, while the figures can be drawn to scale for some implementations, the figures are not necessarily drawn to scale for all examples. Examples and other features and advantages of the present disclosure will be described and explained with additional specificity and detail through the use of the accompanying drawings in which:

FIGS. 1-8 show an example of a stabilizer for holding a delivery device used to implant an implantable prosthetic;

FIGS. 10-12 show an example table for stabilizer devices disclosed herein;

FIGS. 13-34 show various views of components of an example of a stabilizer for holding a delivery device used to implant an implantable prosthetic;

FIGS. 76-116 show various views of components of an example of a stabilizer for holding a delivery device used to implant an implantable prosthetic.

DETAILED DESCRIPTION

Figures 4, 5, 6:
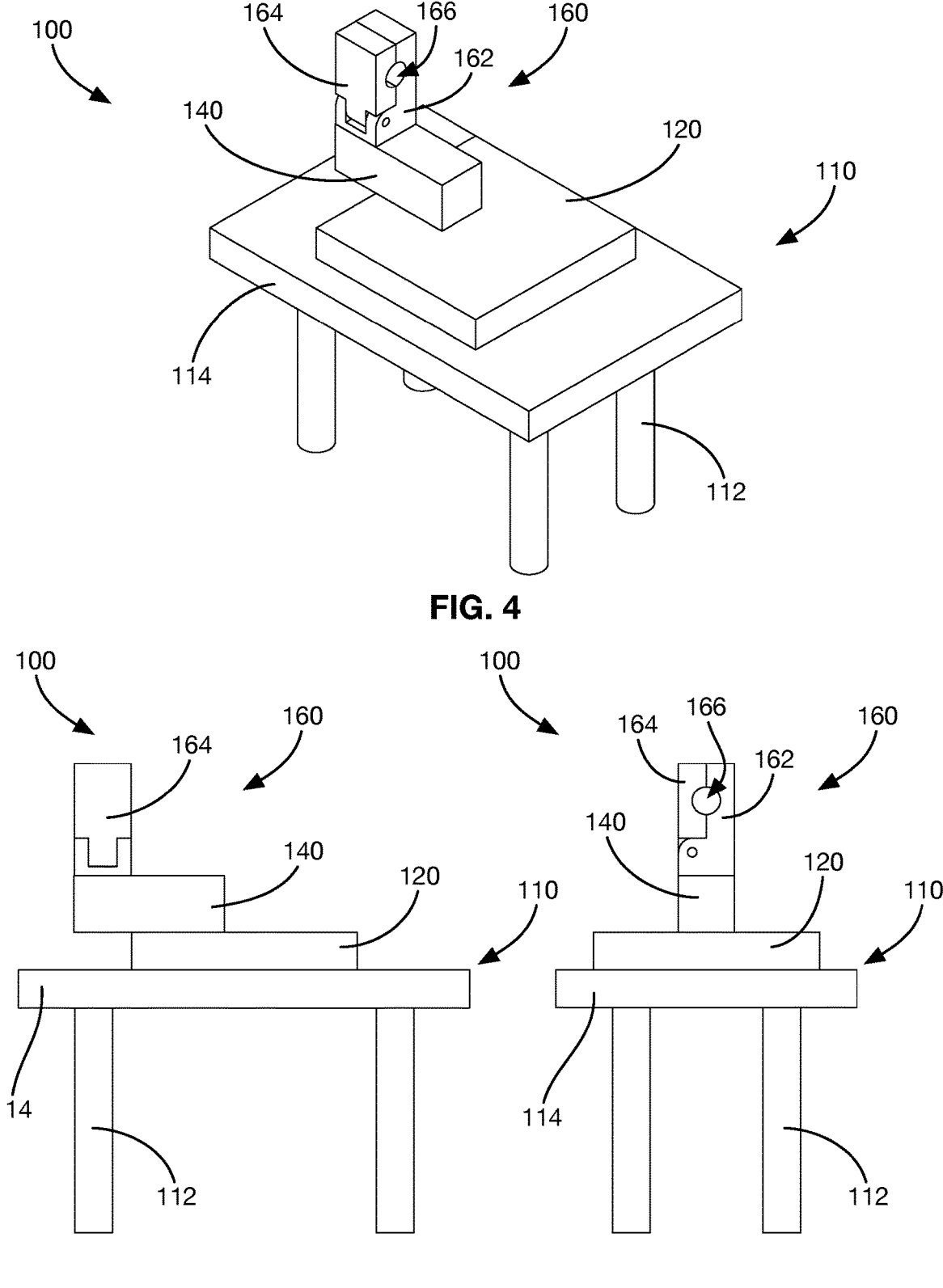
Figure 7:
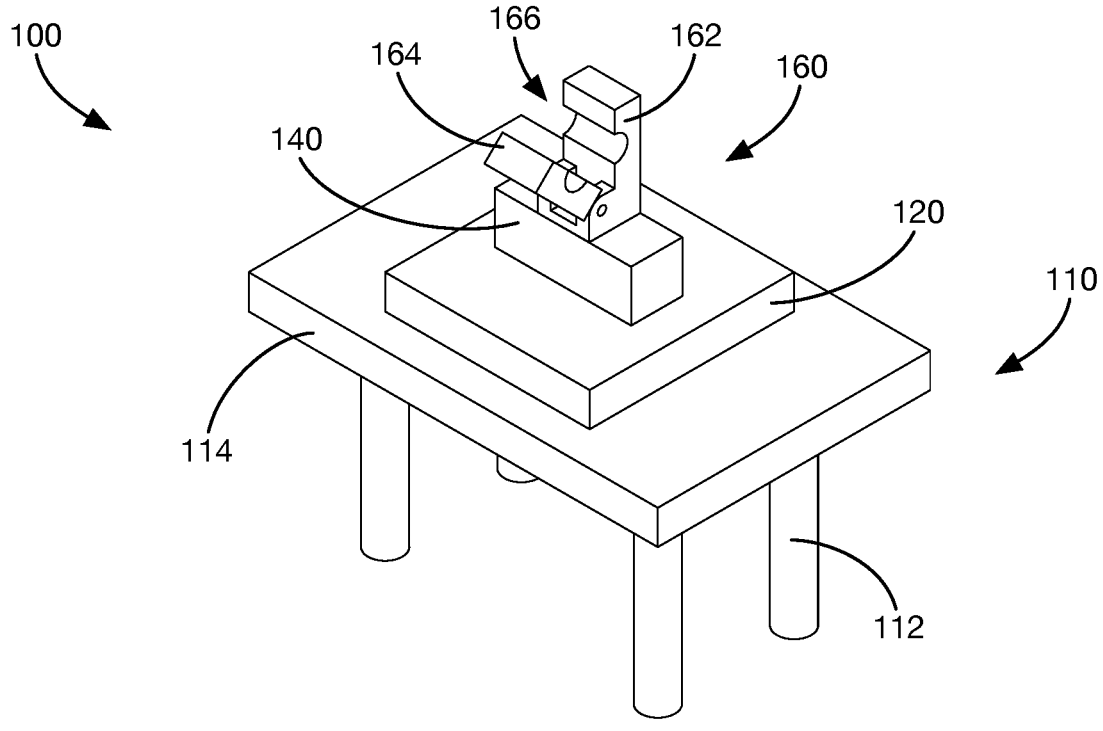
Figure 8:
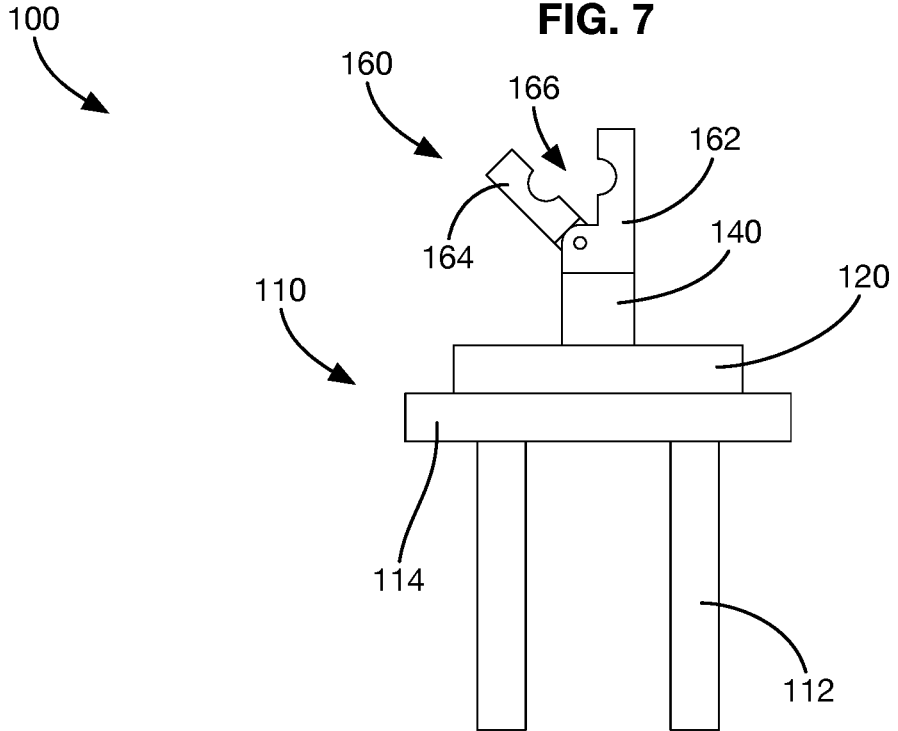
Figure 9:
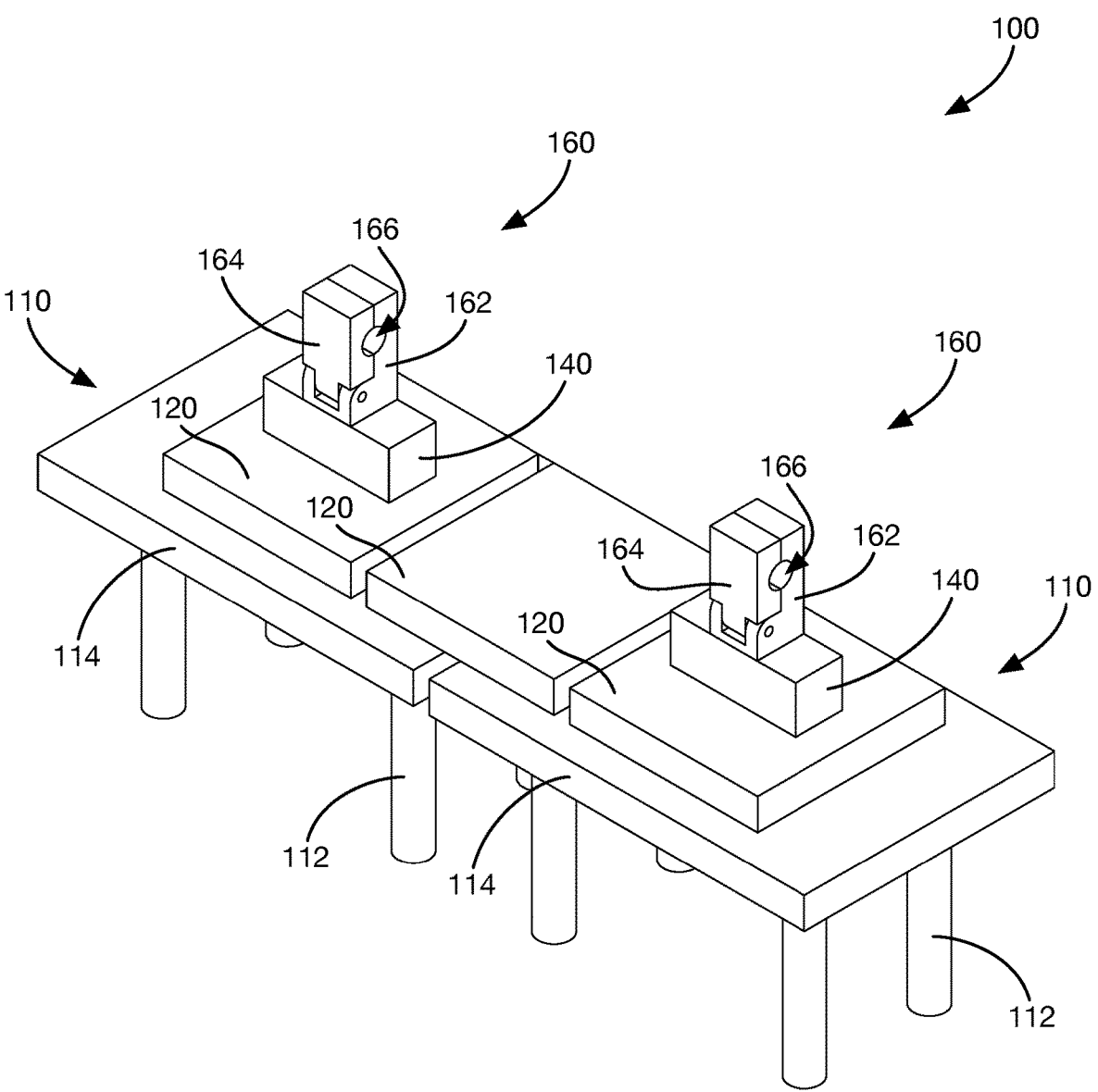
FIG. 9 shows a perspective view of multiple stabilizers of FIGS. 1-8 connected together.

The following description refers to the accompanying drawings, which illustrate specific examples of the present disclosure. Other implementations having different structures and operation do not depart from the scope of the present disclosure.

Examples of the present disclosure are directed to devices and methods for stabilizing medical devices. It should be noted that various examples of medical device stabilization devices are disclosed herein, and any combination of the features of these examples can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

During surgical procedures using a catheter, it typically is beneficial for the operator to be able to precisely control the operation of the catheter because the catheter must be directed through a patient's vasculature. This includes mechanisms that allow the catheter to be bent to assist in navigating the vasculature, and mechanisms that control deployment of the prosthetic valve. During a procedure, the operator can control the catheter using a handle, which can provide controls for extending, retracting, and bending the catheter, including during navigating the patient's vasculature to the delivery or repair site.

Transcatheter procedures can have a long duration, and it may be inconvenient for an operator to manually maintain the position of the catheter handle during the entire procedure. While it may be desirable to adjust the location of the catheter handle relative to the patient at some points during the procedure, at other times it can be desirable to maintain the position of the catheter handle relative to the patient, such as to maintain the depth of insertion of the catheter or the rotational position of the handle.

A catheter handle can be secured to a table proximate the patient using a locking mechanism. Typically, locking mechanisms require a user to actively engage or disengage a locking device to secure or release the catheter handle from a stand or mount. For example, a clamping mechanism may be advanced, such as by advancing a clamp over a threaded shaft, to secure the clamp against the catheter handle and thus secure the catheter handle during a procedure. If it is desired to adjust the position of the catheter handle, the clamp can be released, the position of the catheter handle and/or mount adjusted, and the clamp re-secured. However, these processes can be time consuming and inconvenient.

Stabilizing systems, devices, and tables for supporting the same can be used to hold a medical device—such as a catheter delivery system for implanting an implantable prosthetic device—above a patient during a surgical procedure. The table can also be used as a work surface to hold other tools, implements, or materials, or the like that are needed for the particular procedure. Example stabilizing systems/devices support and position the medical device in a desired location so that the medical device does not move without the direction of the operator of the device. The stabilizing systems/devices disclosed herein can also be easily adjusted so that when the operator does want to reconfigure or move the medical device, such movements are easily accomplished. The example stabilizing systems/devices and tables disclosed herein can also accommodate a sterile barrier, such as a drape, arranged between the stabilizing system/device and the table and remain adjustable without removing the sterile barrier. This arrangement provides a significant advantage over prior art methods of fixing stabilizing systems/devices to tables using clamps that must be opened and moved to adjust the position of the stabilizing system/device relative to the table. To accommodate medical devices of different lengths, the example stabilizing systems/devices disclosed herein can span multiple tables, thereby enabling an operator to configure work surfaces of different lengths using the same components.

The stabilizing systems/devices can be configured to be assembled to a table with a sterile barrier provided between the two. A base plate of the stabilizing system/device engages the table to securely attach the stabilizing system/device to the table. A carriage and a clamp of the stabilizing system/device remain movable relative to the base plate and table to provide customizability of the clamp position to the operator. Various mechanisms can be employed to connect the clamp, carriage, and base plate to facilitate adjustment of the relative positions of these components, and the locking or release thereof. The stabilizing methods for various examples can be different and are more fully discussed below with respect to each example. Additional information regarding these and other stabilization devices can be found in U.S. Provisional Application No. 62/491,392 and U.S. patent application Ser. No. 15/905,257 each of which is incorporated herein by reference in its entirety.

Referring now to FIGS. 1-9, an example of a stabilizing apparatus, system, or device 100 is shown. In some implementations, the stabilizing system or device 100 includes a table 110, a base plate 120 removably attached to the table 110, a carriage 140 attached to or formed on the base plate 120, and a clamp 160 attached to the carriage 140. The stabilizing system/device 100 can incorporate any of the features of stabilizing systems/devices disclosed herein and can be made from any suitable material, such as, for example, metal or plastic. In some implementations, the carriage can be a separate component or integrally formed with the base plate.

The table 110 has legs 112 for elevating a platform 114 above a patient undergoing a procedure with a medical device that is stabilized by the stabilizing system/device 100. The legs 112 can optionally be removed from the platform 114 so that the table 110 can be stored or transported in a compact manner. The legs 112 can include feet (not shown) so that fewer than four legs are needed to support the table 110 in a stable condition. (E.g., the table 200 shown in FIGS. 10-12.) The platform 114 can also include a variety of leg attachment locations for reconfiguring the legs 112, for example, to avoid obstacles.

The base plate 120 is removably attached to the table by any suitable means, such as, for example, with threaded fasteners, snaps, spring-loaded clamps, hook and loop fasteners, or the like. The base plate 120 can be configured to be entirely or partially retained by features of the table 110 so that when the table is covered by a sterile barrier (not shown), such as a drape, the base plate 120 can still be attached to the table 110. (See, e.g., the examples described below.) That is, the base plate 120 can be attached to the table 110 without attachment means, such as fasteners, that would pierce or puncture the sterile barrier arranged between the table 110 and the base plate 120. Also, the base plate 120 can be formed as a single piece or as multiple pieces that can be rearranged to change the size or length of the base plate 120.

In some implementations, the carriage 140 is moveably—and optionally, removably—attached to the base plate 120 so that the carriage 140 can be moved along the base plate 120 relative to the table 110 while the base plate 120 remains fixed relative to the table 110. For example, as can be seen in FIGS. 4-6, the carriage 140 can be moved to one side of the base plate 120 and can even extend beyond the edge of the base plate 120 if allowed by the means used to attach the carriage 140 to the base plate 120. The carriage 140 can be attached to one or more rails protruding from the base plate 120 or can include protrusions that are received within one or more grooves or channels formed in the base plate 120. The carriage 140 can be moved relative to the base plate 120 along a predetermined path and can be locked into position along the path in a desired location. The carriage 140 can be locked in place with a spring-loaded latch (not shown) or any other suitable locking means, such as, for example, a threaded fastener, a set screw, a locking pin, a cam lock, or the like. Also, the locking means can be configured to retain the carriage 140 on the base plate 120 so that the carriage 140 resists forces that would tend to pull the carriage 140 away from the base plate 120.

In some implementations, the clamp 160 includes a fixed jaw 162 and a movable jaw 164 and is opened and closed by pivoting (FIGS. 7-8) and/or sliding relative to the fixed jaw 162, but the clamp can be the same as or similar to other clamps described herein. The movable jaw 164 can optionally be biased—such as, for example, with a spring—toward the fixed jaw 162 so that the clamp 160 remains in a closed condition unless opened by an application of an opening force to the movable jaw 164. The opening force can be applied to the movable jaw 164 directly or with an actuation device, such as a lever or actuator. A lever or actuator used to open the movable jaw 164 can also be configured to hold the jaw 164 in an open or partially open position, to facilitate insertion and/or rotation of a medical device. In some implementations, the clamp 160 does not have a fixed jaw 162 and instead has two movable jaws 164 that can optionally be biased toward each other. The jaws 162, 164 of the clamp 160 come together to form an opening 166 for receiving the medical device (not shown) to be stabilized by the stabilizing device 100.

The clamp 160 is moveably attached to the carriage 140 so that the position of the clamp 160 can be adjusted along the length of the carriage 140 (shown in FIGS. 4-6), thereby providing additional adjustability to the user. The clamp 160 can optionally be adjusted rotationally relative to the carriage 140 to accommodate different shaped medical devices. The adjustment of the position of the clamp 160 can be done directly or by way of an adjusting mechanism. The clamp 160 can also be locked in position by a locking mechanism (not shown) to secure the clamp 160 in a desired position. The locking mechanism can be opened or released to enable the clamp 160 to be moved along the carriage 140. Optionally, the locking mechanism can be biased in a locking direction so that the clamp 160 remains locked in position unless the locking mechanism is actively released. The release mechanism for such a biased locking mechanism can also include a holding position that enables the locking mechanism to be held open without the operator having to continuously hold the locking mechanism open. In some implementations, the locking and adjustment mechanism are combined into a single mechanism that provides both functions to the clamp 160 and carriage 140 assembly. In some implementations, the carriage can include one or more rails (e.g., similar to rails 646 and 648 shown and described later herein) to which the clamp(s) can be slidably attached.

Referring now to FIGS. 10-12, an example table 200 for use with stabilizing devices disclosed herein is shown. The table 200 includes a platform or tabletop 210 supported by two legs 220. The platform has side walls or barriers 212 extending above the platform 210 to a plurality of latching protrusions 214 that are spaced apart by gaps 216 and configured to engage a baseplate of a stabilizing device such as the stabilizing devices disclosed herein and described in detail below. The platform 210 also includes two pairs of openings 218 for receiving and attaching to the legs 220. The openings 218 can be threaded, as shown in FIG. 10, or can include a slot or other locking feature that would sufficiently secure the legs 220 to the platform 210, such as, for example, for a quarter-turn locking feature.

The legs 220 include horizontally extending feet 222 and vertical supports 224 that extend upward from the feet 222 toward the platform 210. A threaded connection (not shown) at the top of the vertical supports 224 can be used to connect the legs 220 to the platform 220. Optional extensions 226 can be attached to the top of the vertical supports 224 to further increase the height of the platform 210 of the table 200 relative to the bottom of the feet 222. The extensions 226 include a female thread portion (not shown) to engage the vertical supports 224 and a male thread portion (not shown) for engaging the threaded openings 218 of the platform 210. The male thread portion of the extensions 226 is the same as the male thread portion of the vertical supports 224. While threaded connections are used in the illustrated example, any suitable connection for removably connecting the legs 220 to the platform 210 can be used, such as, for example, slotted connections, quarter turn connections, pinned connections, spring-loaded latch or clamp connections, or the like.

Referring now to FIGS. 13-35, an example of a stabilizing device 300 is shown. The stabilizing device 300 includes a base plate 320. A carriage 340 can be attached to the base plate 320 or integrally formed therewith. One or more clamps 360 can be attached to the carriage 340 or the base plate 320. The stabilizing device 300 can incorporate any of the features of stabilizing devices disclosed herein and can be made from any suitable material, such as metal or plastic.

Referring now to FIGS. 14-17, in some implementations, the stabilizing device 300 includes a release 342 (such as a release button, knob, latch, lever, etc.) (See FIG. 14) for releasing the carriage 340 from the base plate 320 for disassembly and/or for lateral movement of the carriage 340 along the base plate 320. In some implementations, a knob 344 (or other actuator such as a button, latch, lever, etc.) arranged on a side of the carriage 340 can be actuated (e.g., turned) to move the clamp 360 back and forth along the carriage 340. In other words, the release 342 can operate as a coarse adjustment mechanism for the position of the clamp 360 relative to the base plate 320 and the actuator/knob 344 can operate as a fine adjustment mechanism for the position of the clamp 360 relative to the carriage 340.

Figure 18:
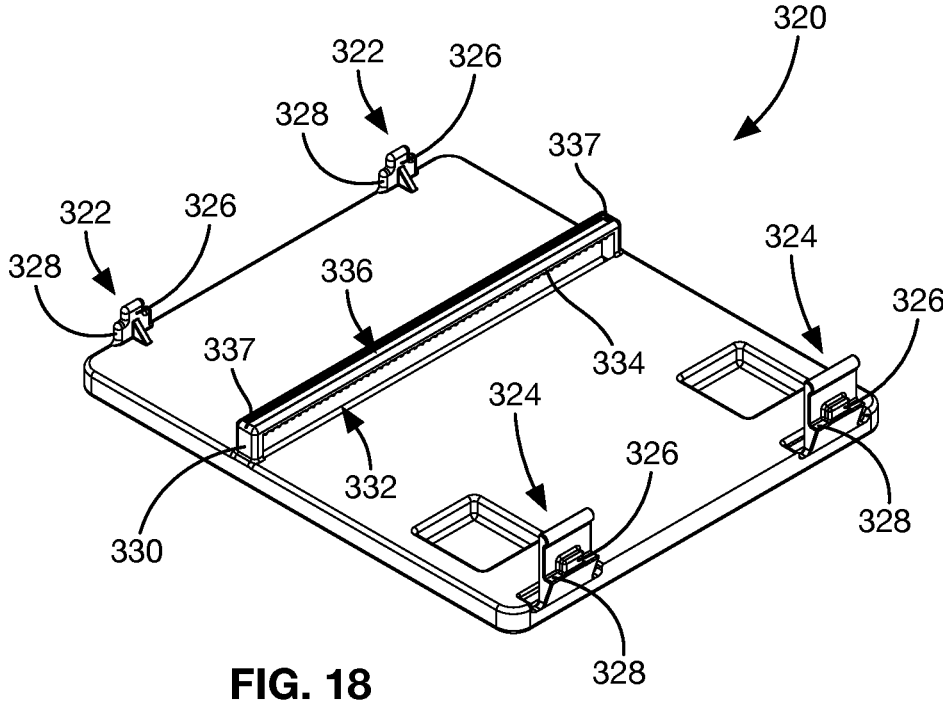
Figure 19:
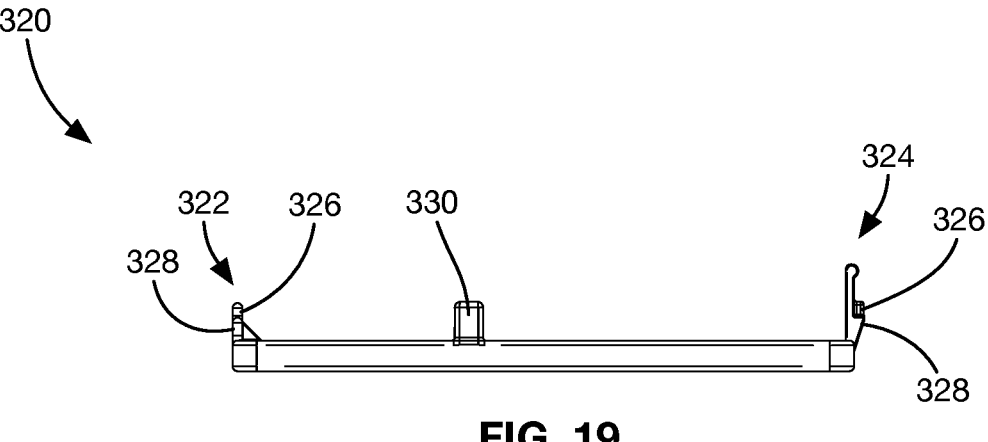
Figure 20:
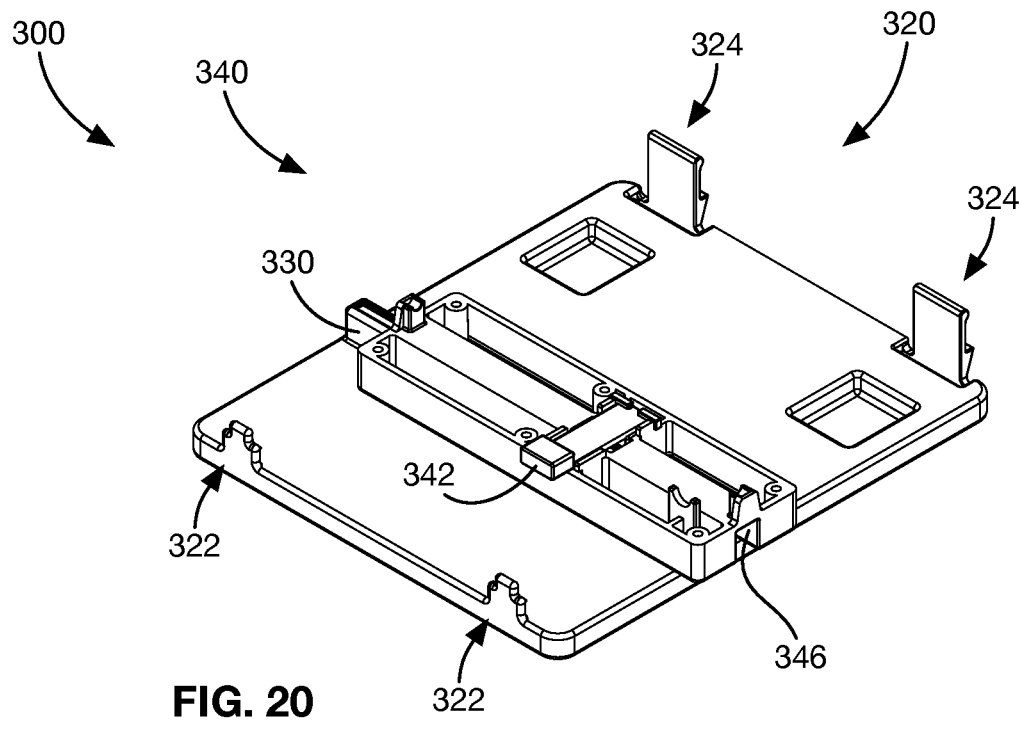
Figure 21:
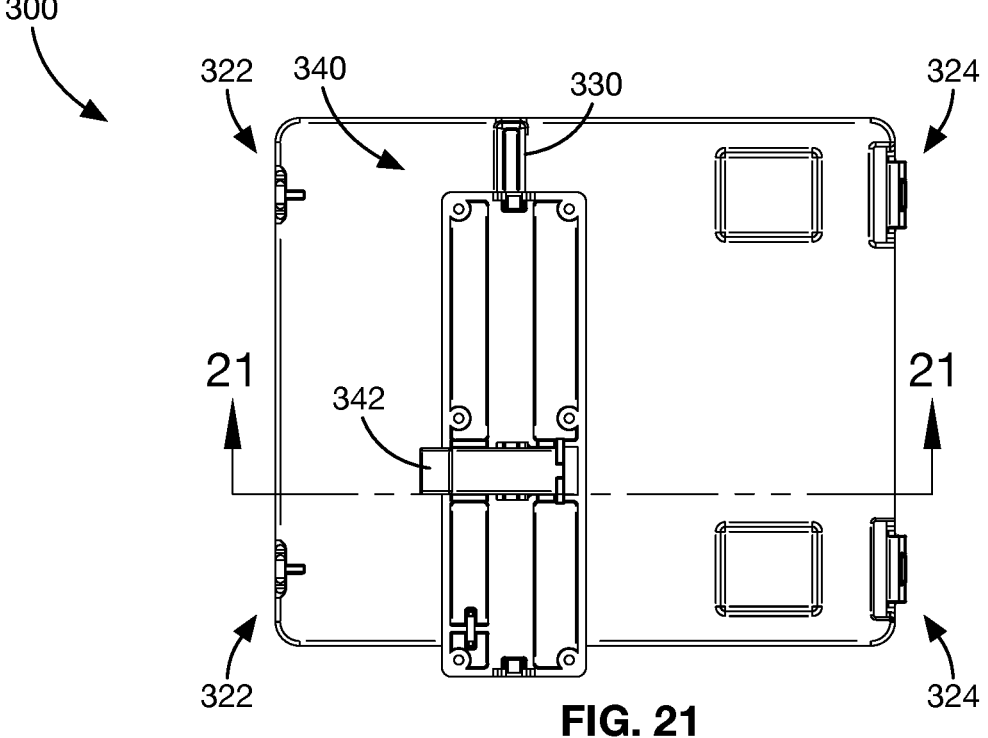

Referring now to FIGS. 18-19, an example base plate 320 is shown. In some implementations, the base plate 320 has rigid tabs 322 and spring or flexible tabs 324 for attaching to the table 200. The tabs 322, 324 include alignment portions 326 that fit in the gaps 216 of the side walls 212 of the table 200 and retention shoulders 328 that fit underneath the latching protrusions 214 of the side walls 212 of the table 200 (See FIG. 10). The base plate 320 is assembled to the table 200 by first inserting the alignment portions 326 of the rigid tabs 322 into the gaps 216 between the latching protrusions 214 of the side walls 212 so that the shoulders 328 of the rigid tabs 322 are retained by the latching protrusions 214. The other side of the base plate 320 is then pressed downward so that the alignment portions 326 and shoulders 328 of the flexible tabs 324 snap into the latching protrusions 214 of the opposite side wall 212. The flexible tabs 324 can include a ramp or inclined portion to provide a smoother engagement with the latching protrusions 214.

Figure 13:
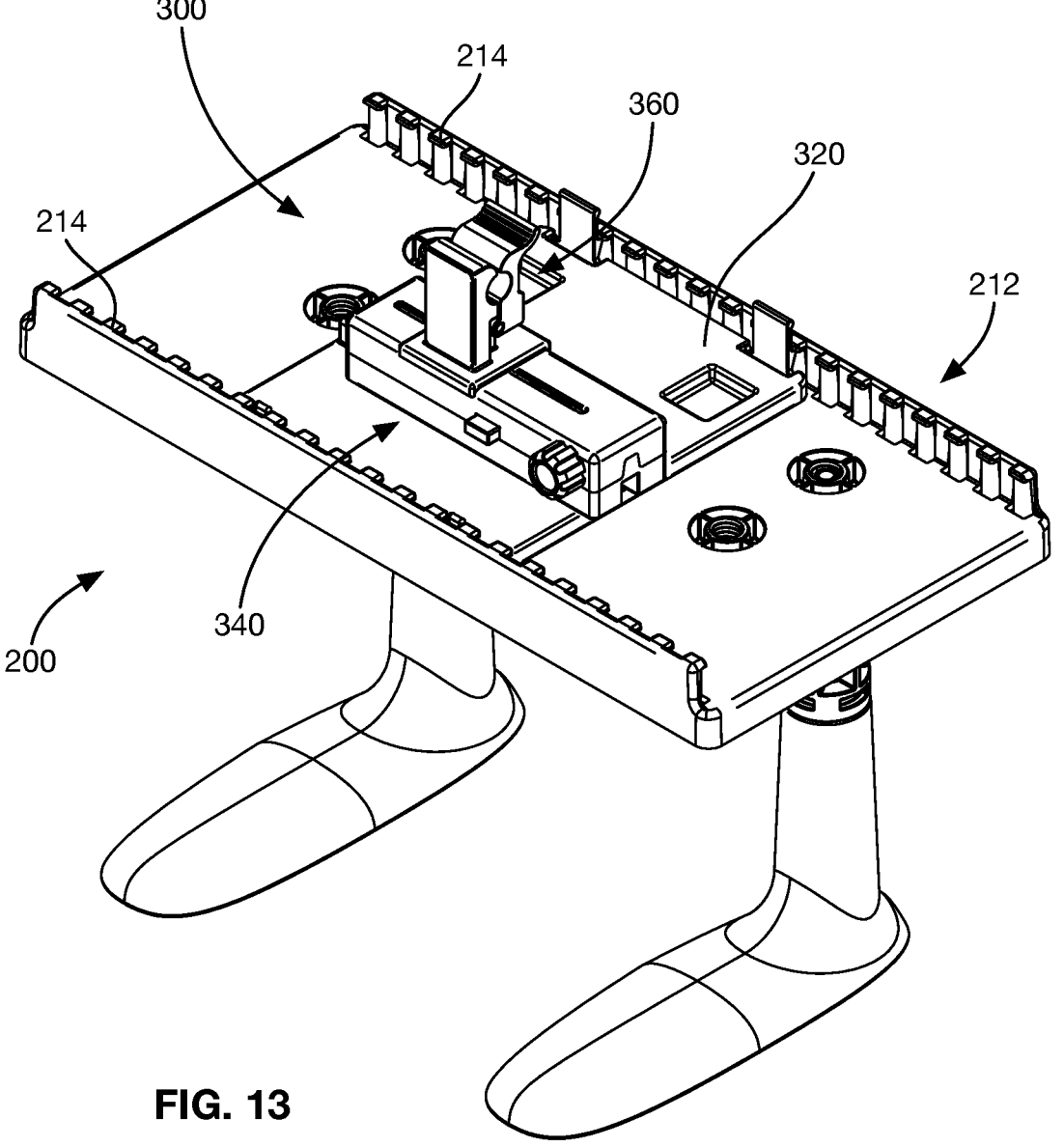
Figure 14:
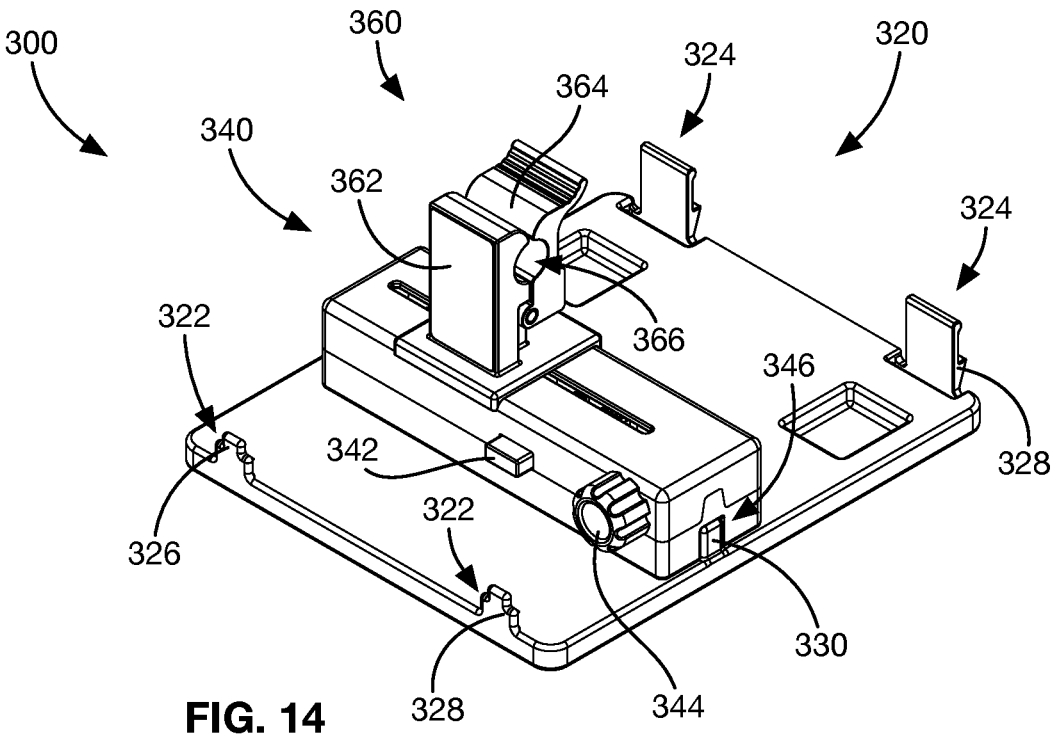
Figure 15:
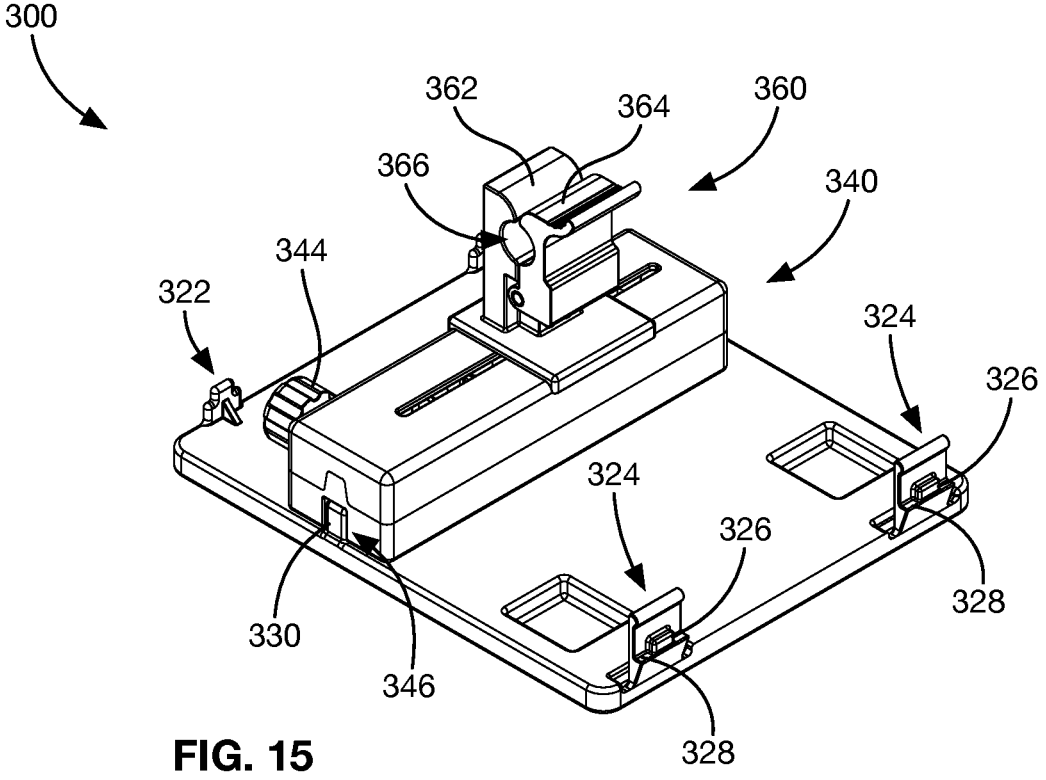
Figure 16:
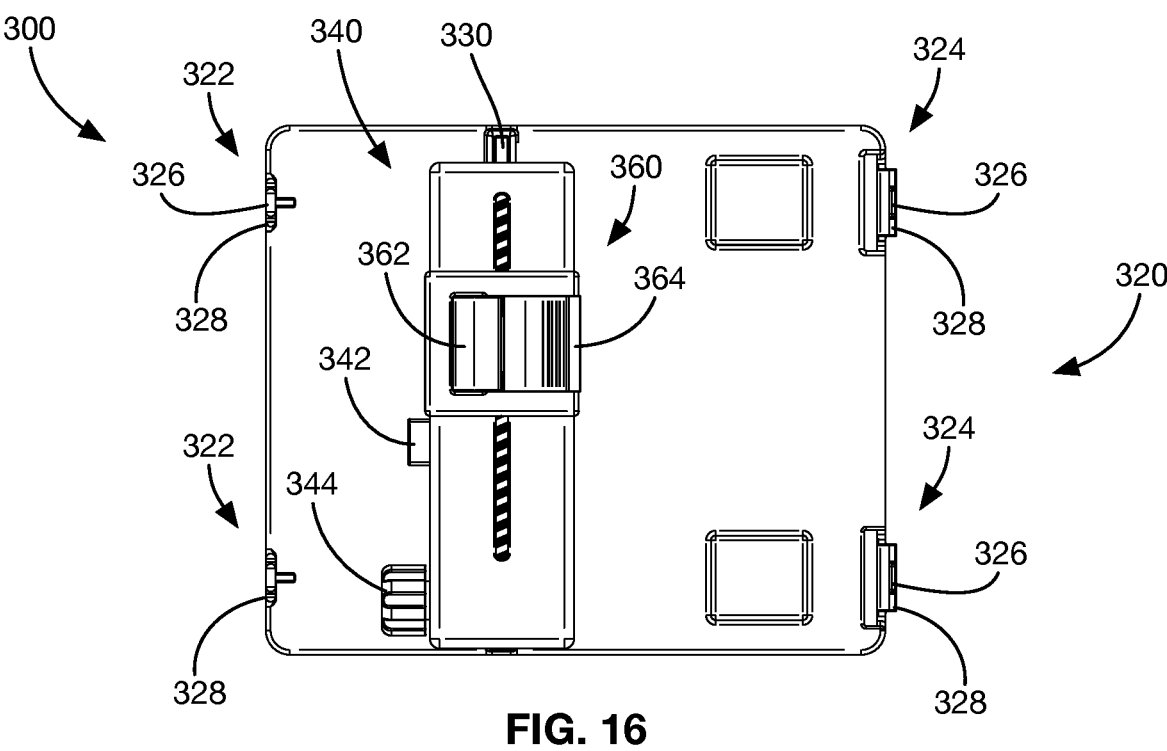
Figure 17:
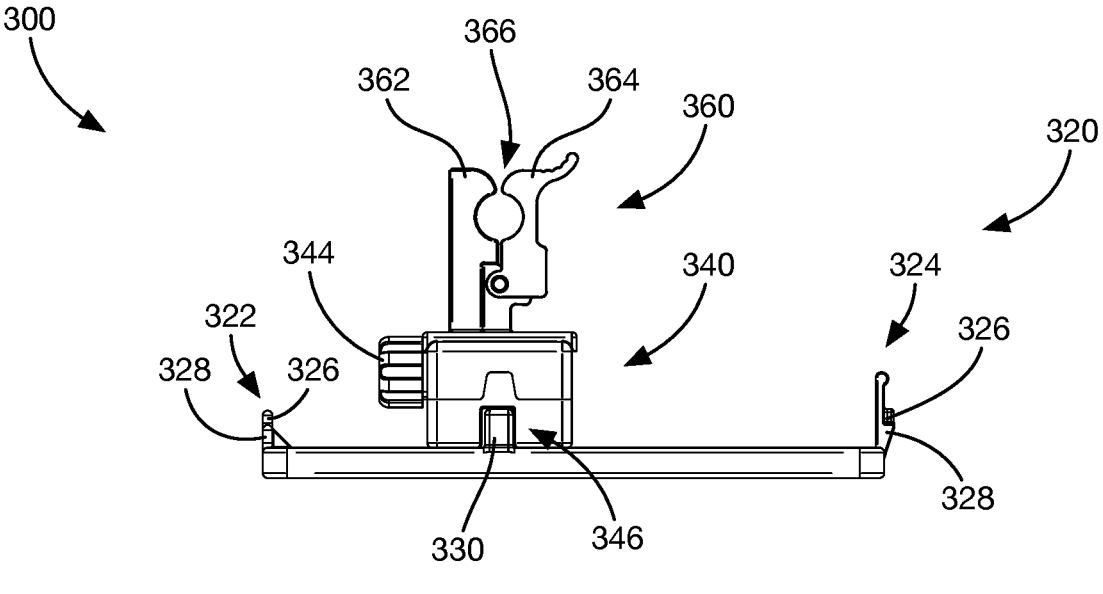
Figure 35:
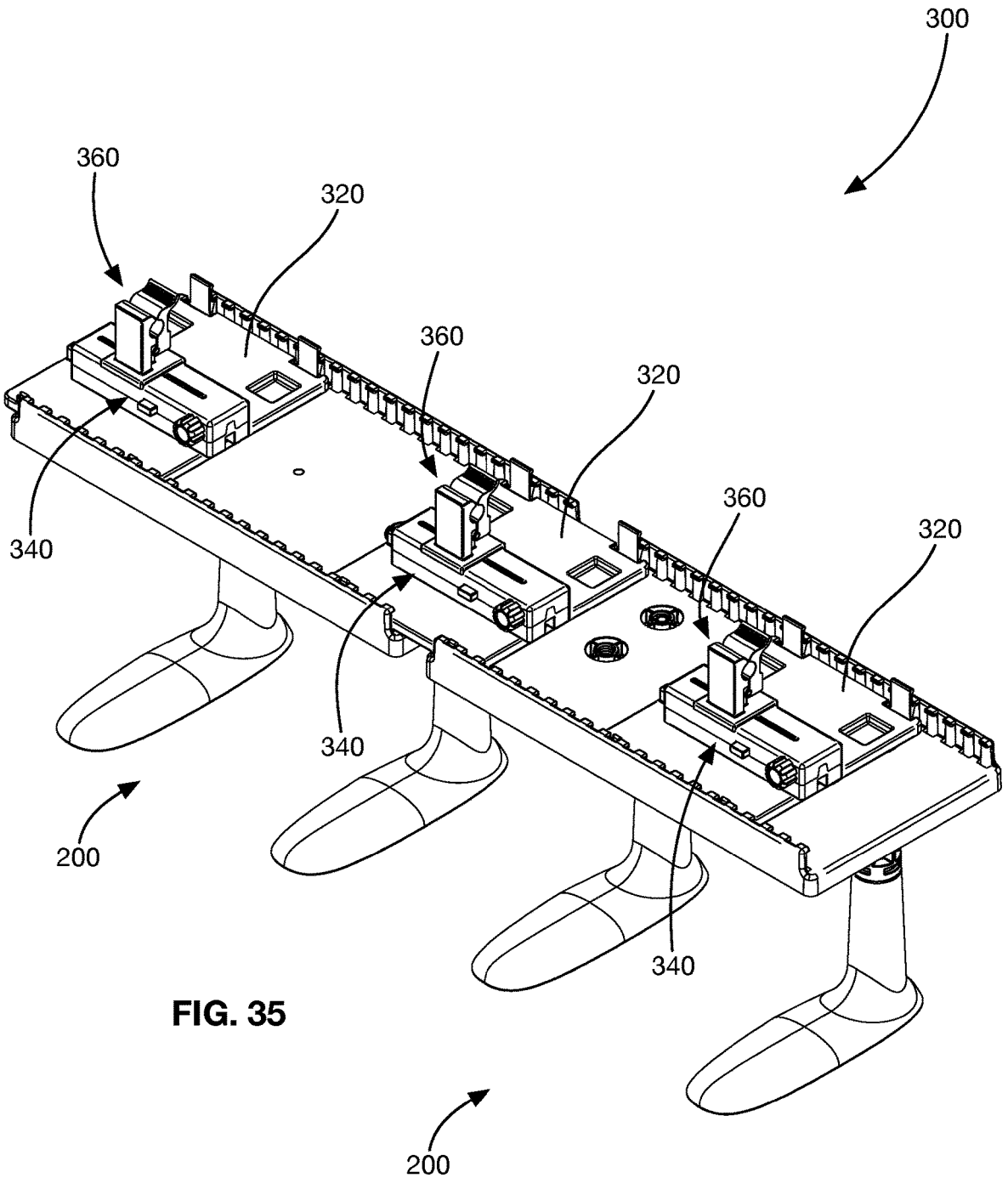
FIG. 35 shows a perspective view of multiple stabilizers of FIGS. 13-22 connected together.
Figure 36:
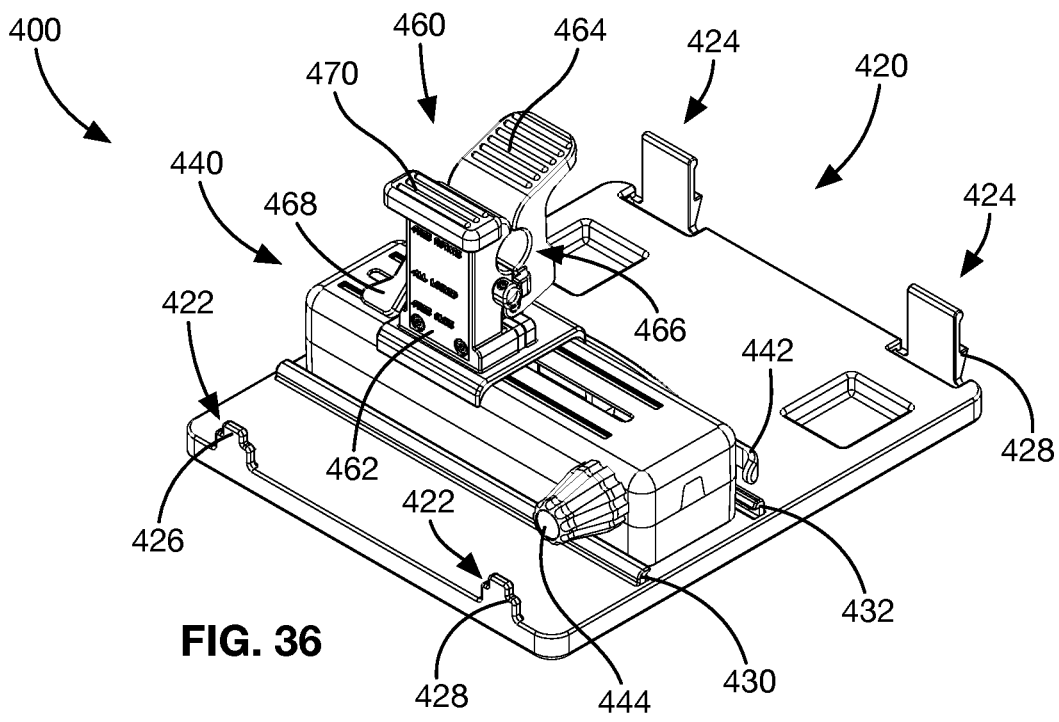
FIGS. 36-58 show various views of components of an example of a stabilizer for holding a delivery device used to implant an implantable prosthetic.
Figure 37:
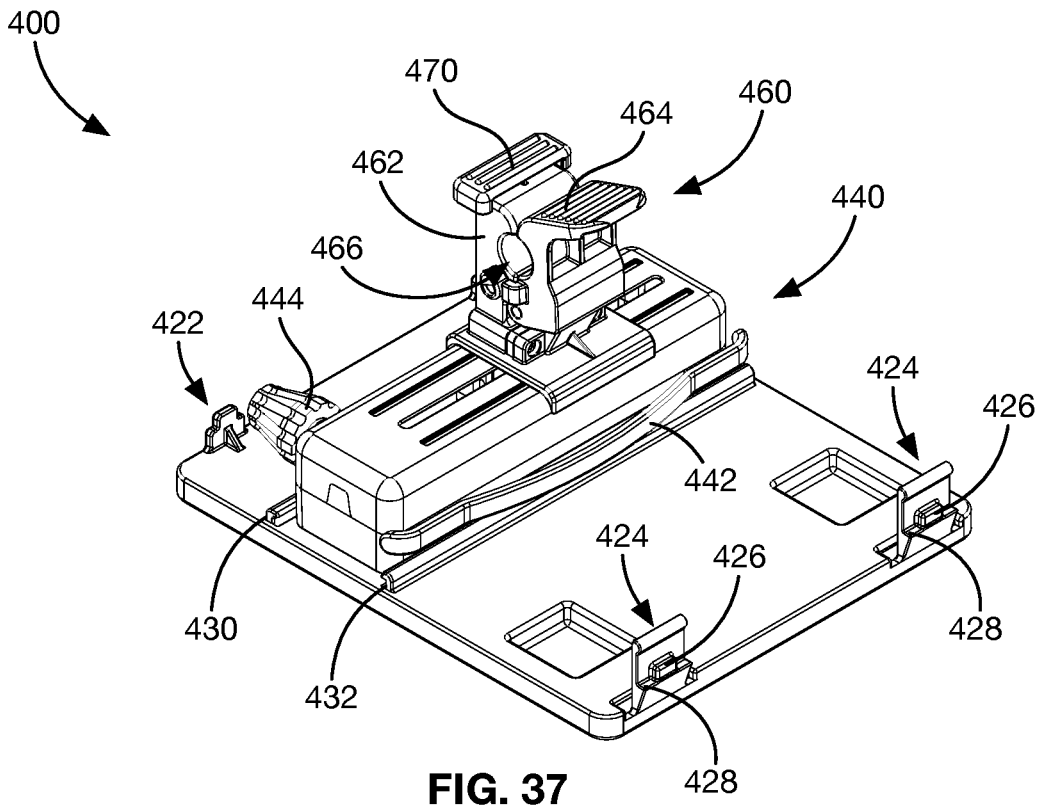
Figure 38:
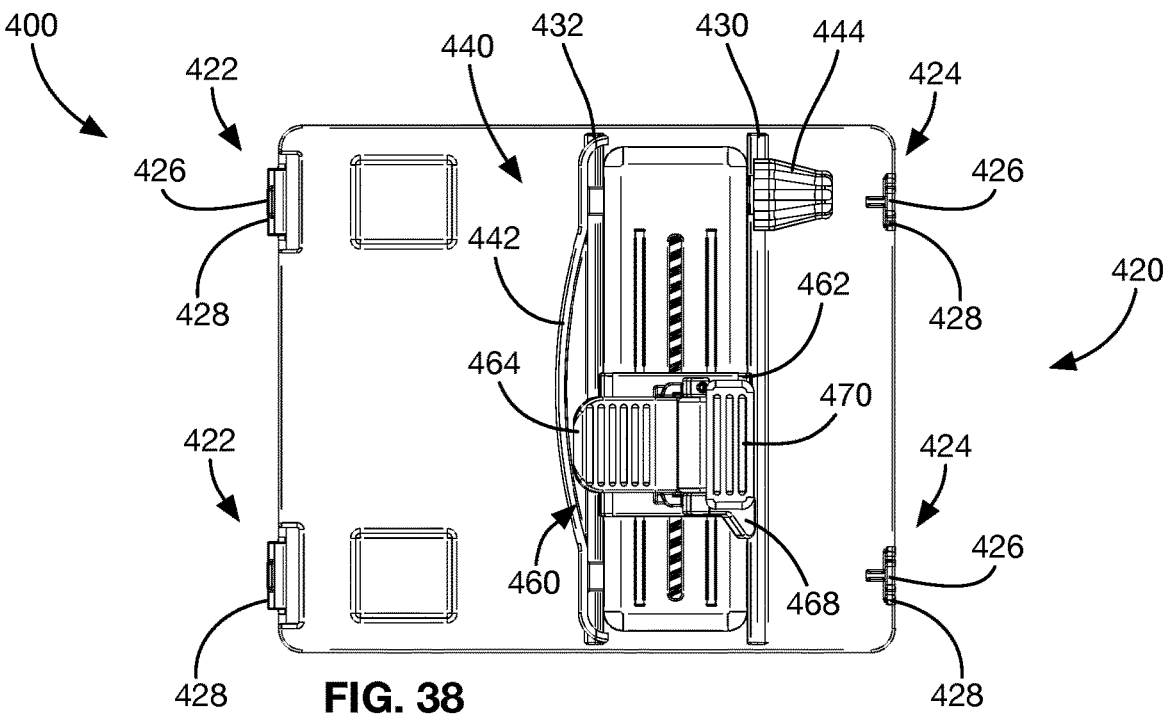
Figure 39:
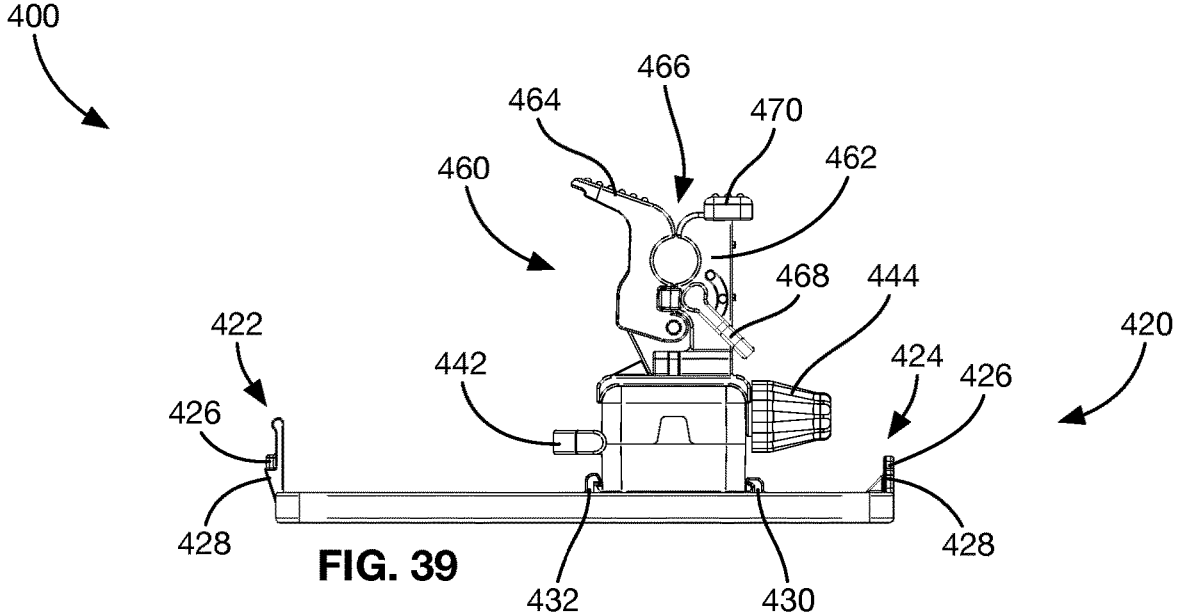

In some implementations, to remove the base plate 320 from the table 200, the upper ends of the flexible tabs 324 are pressed inward until the shoulders 328 are released from beneath the latching protrusions 214 to enable the base plate 320 to be lifted upward and removed from the table 200. Sufficient space is provided between the base plate 320 and table 200 so that a sterile barrier, such as a drape, can be provided between the two. That is, a sterile barrier can be laid on top of the table 200 before the base plate 320 is snapped into place between the side walls 212 of the table 200. As can be seen in FIGS. 13 and 35, the base plate 320 of the stabilizing device 300 can be configured to attach the stabilizing device 300 to one or more tables 200 described above and shown in FIGS. 10-12.

Referring now to FIGS. 20-30, various views of an example carriage 340 and mechanisms thereof are shown. In some implementations, the carriage 340 moveably and removably attaches to a mounting rail 330 that extends across the base plate 320. Though in some implementations, the carriage 340 may be a carriage portion or carriage feature of the base plate 320, e.g., an integral part of the base plate.

Figure 22:
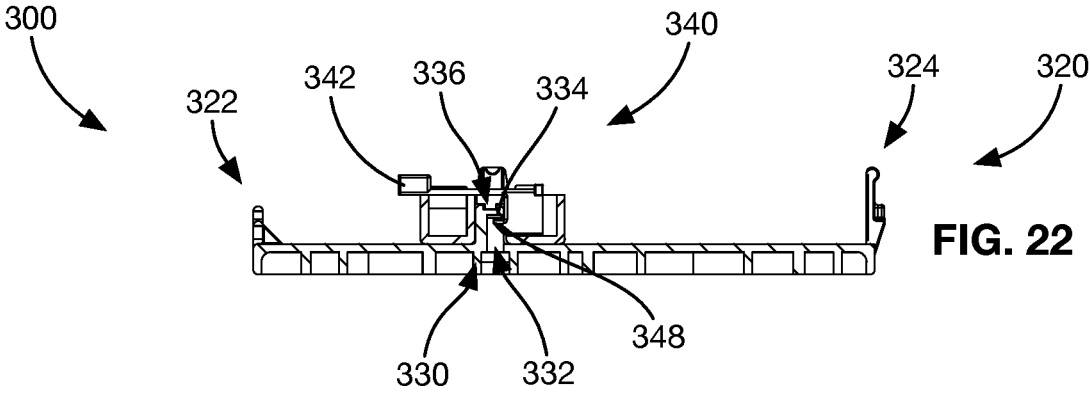
Figure 23:
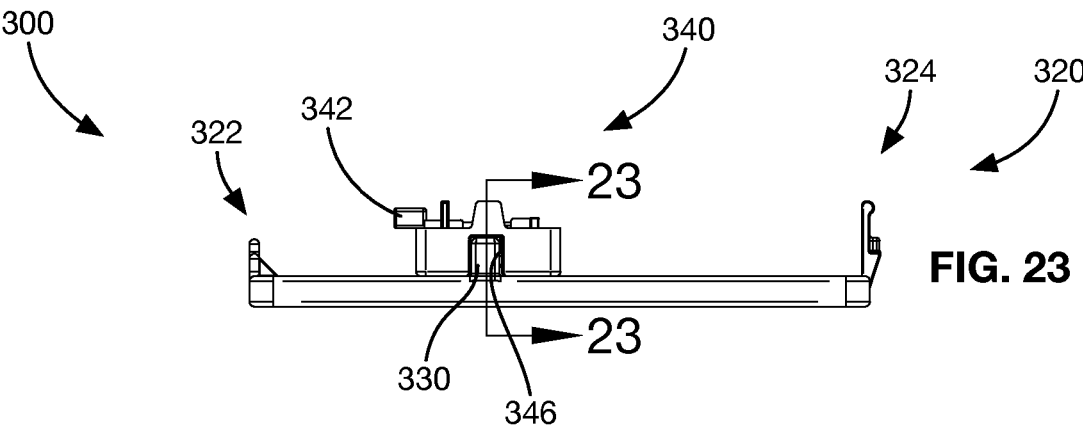
Figure 24:
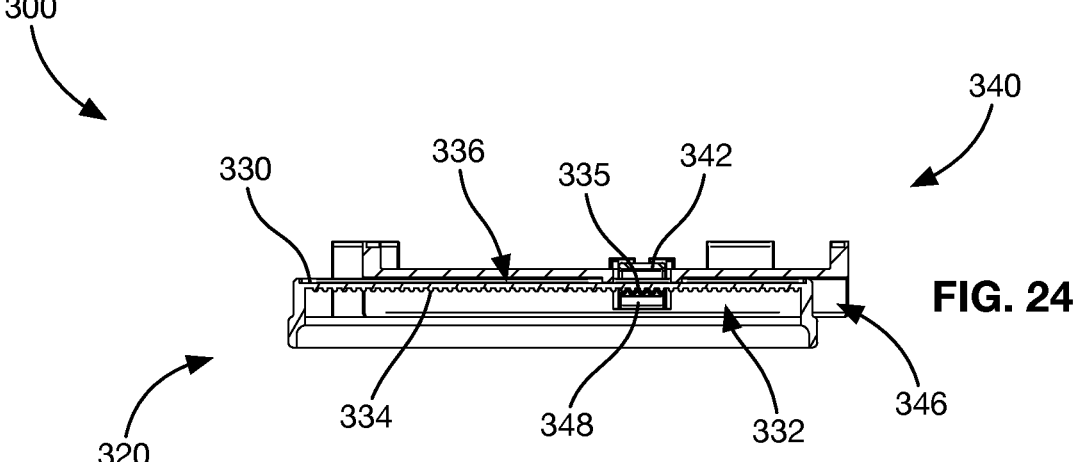

In some implementations, the mounting rail 330 is received within a guide channel 346 of the carriage 340 and latched in place. (See FIGS. 20-24.) Referring to FIG. 22, a latch recess 332 in one or both sides of the mounting rail 330 receives a latch 348 of the carriage 340 that is opened by the release button 342. Referring to FIG. 24, locking teeth 334 extending down from the upper surface of the latch recess 332 engage similar teeth 335 extending up from the latch 348. The locking teeth 334 and teeth of the latch 348 mesh together to prohibit longitudinal movement of the carriage 340 once the mounting rail 330 has been engaged by the latch 348.

The top of the mounting rail 330 (See FIG. 18) includes a limiting recess 336 with ends 337 for receiving limiting tabs 356 (FIGS. 29-30) of the carriage 340 to prevent the carriage 340 from being moved beyond a position on the mounting rail 330 that would not be sufficiently stable to support the clamp 360.

Referring now to FIGS. 20-24, example release 342 and latch 348 mechanism are shown in greater detail. The carriage 340 can be attached or moved to any position on the mounting rail 330 (within the limit defined by the limiting recess 336 and tab 356) by depressing the release 342 to retract the latch 348 out of the latch recess 332 (See FIG. 22). This allows the guide channel 346 to slide over the mounting rail 330 to adjust the position of the carriage 340 on the base plate 320. The latch 348 can optionally be biased to a closed position by a biasing member, such as, for example, a spring, shape memory material, elastic member, etc.

The latch 348 can also include a beveled bottom edge so that the carriage 340 can be attached to the base plate 320 by aligning the guide channel 346 with the mounting rail 330 and pressing down on the carriage 340 to snap the carriage 340 onto the mounting rail 330—that is, by causing the latch 348 to open via the application of force against the inclined portion. Once past the top of the mounting rail 330, the latch 348 springs closed and engages the latch recess and locking teeth 334.

Once attached, a rough or coarse adjustment of the position of the carriage 340 can be made by depressing the release 342 to move the latch 348 out from the latch recess 332 to disengage the teeth of the latch 348 from the locking teeth 334 to free the carriage 340 to be moved along the mounting rail 330.

Figure 25:
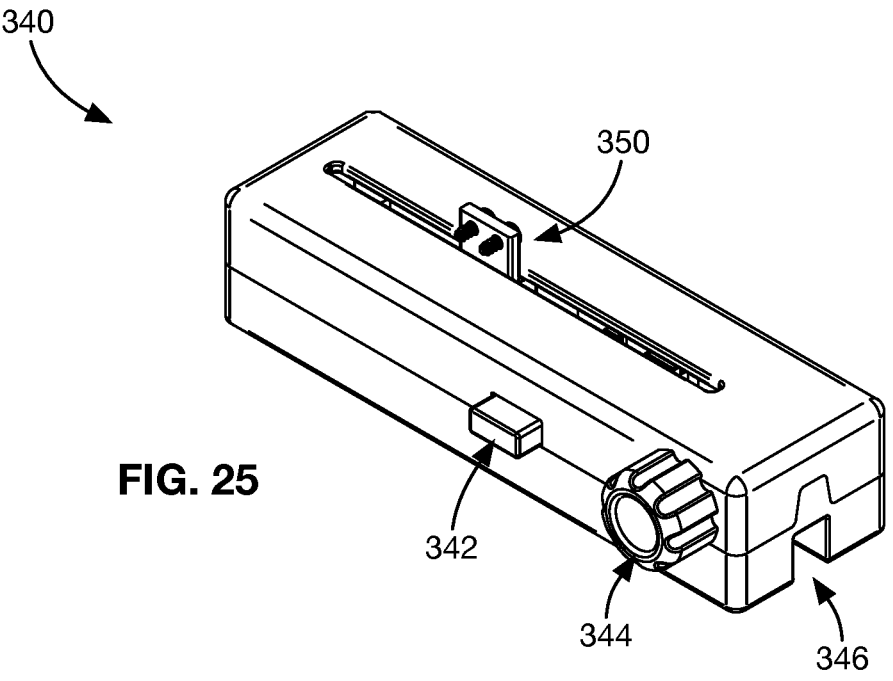
Figure 26:
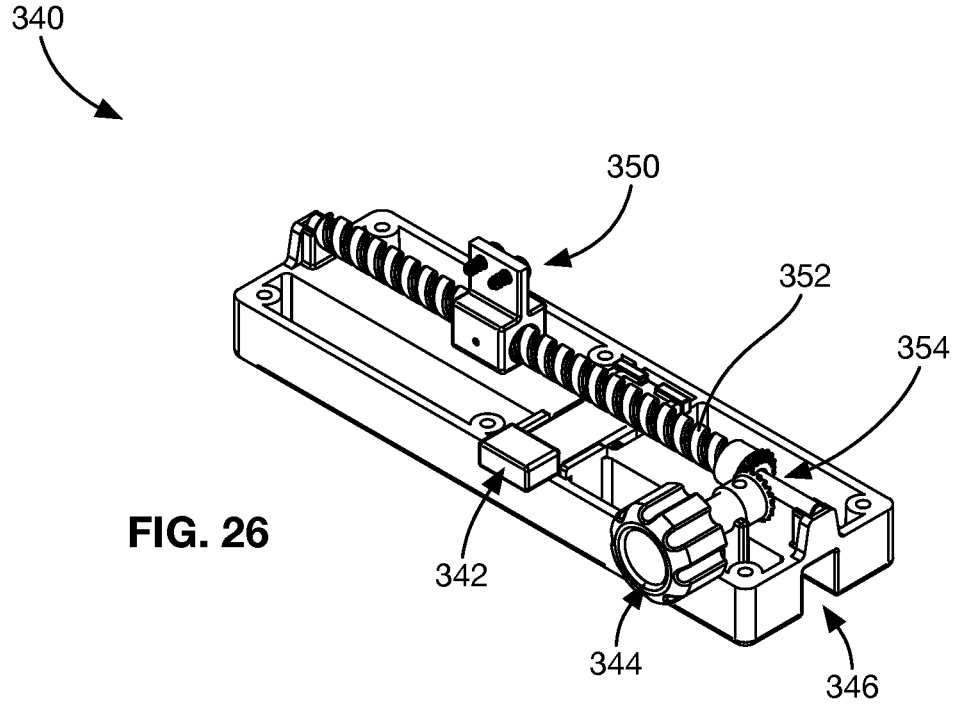
Figure 27:
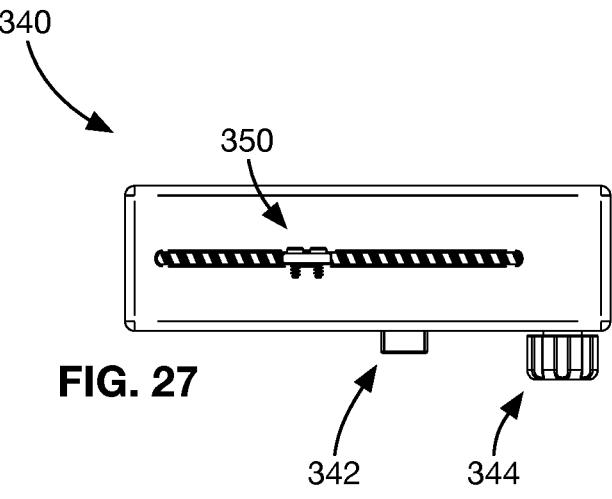
Figure 28:
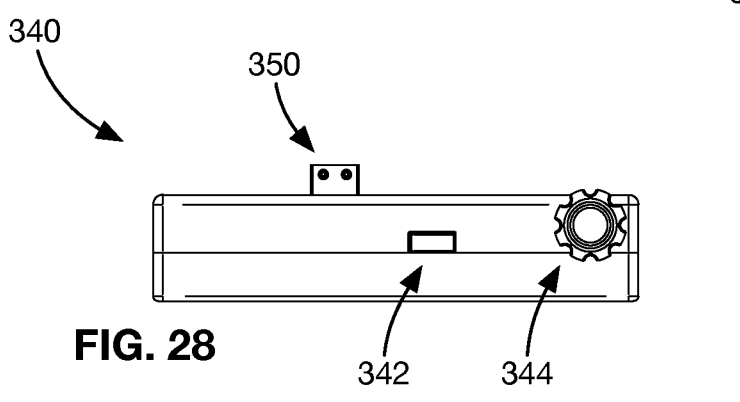
Figure 30:
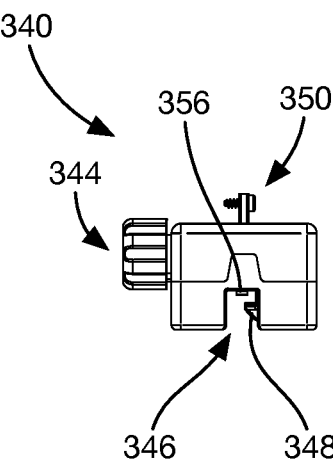
Figure 29:
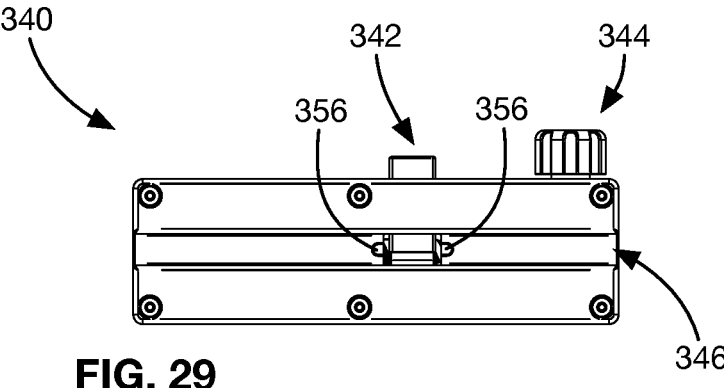

FIGS. 25-30 illustrate the example carriage 340. In FIG. 25 the carriage 340 is shown fully assembled and including the fine adjustment mechanism for adjusting the position of the clamp 360 relative to the carriage 340. Referring to FIG. 26, a fine adjustment actuator or knob 344 is attached to a set of bevel gears 354 for translating the rotation of the knob 344 into rotation of a worm drive or gear 352 that extends through a traveler 350. While sometimes referred to as a knob, other actuators could also be used. The traveler 350 includes a pin (not shown) that fits within the groove of the worm drive 352 so that rotation of the worm drive 352 causes the traveler 350—and, consequently, the clamp 360—to translate along the worm drive 352 and thus, the length of the carriage 340.

Referring now to FIGS. 31-34, the clamp 360 is shown in closed (FIGS. 31-32) and open (FIGS. 33-34) positions. The clamp 360 includes a fixed jaw 362 and a movable jaw 364 that is opened and closed by pivoting the movable jaw 364 relative to the fixed jaw 362. The movable jaw 364 is biased with a spring toward the fixed jaw 362 so that the clamp 360 remains in a closed condition unless opened by an application of an opening force to the movable jaw 364. The jaws 362, 364 of the clamp 360 come together to form an opening 366 for receiving the medical device (not shown), such as a catheter, to be stabilized by the stabilizing device 300. In the closed position, the fixed and movable jaws 362, 364 might remain spaced apart so that the closing force of the clamp 360 is applied to the medical device to stabilize and prohibit rotation of the medical device.

The clamp 360 further includes a mounting recess 368 configured to receive and engage with a mounting portion of the traveler 350 so that the position of the clamp 360 can be adjusted along the length of the carriage 340 by rotation of the adjustment knob 344.

Referring to FIG. 35, in one example, one or more base plates 320 can be used to attach two or more tables together. In the example illustrated by FIG. 35, a base plate 320 spans between and attaches two tables 200 together. The spanning base plate 320 can be attached to the tables 200 in a wide variety of different ways. In one example, the spanning base plate attaches to the two connected tables 200 in the same manner as a base plate 320 is attached to a single table 200.

Referring now to FIGS. 36-58, an example of a stabilizing system or stabilizing device 400 is shown. The stabilizing device 400 can includes a base plate 420, a carriage 440 attached to the base plate 420 (or a carriage-like feature formed in or as part of the base plate), and one or more clamps 460. The one or more clamps 460 can be attachable to the carriage 440. The stabilizing device 400 can incorporate any of the features of stabilizing devices disclosed herein and can be made from any suitable material, such as metal and/or plastic.

Referring now to FIGS. 36-39, in some implementations, the stabilizing device 400 includes a release 442 (e.g., a button, latch, knob, lever, etc.) for releasing the carriage 440 from the base plate 420 for disassembly and/or for lateral movement of the carriage 440 along the base plate 420. An actuator or knob 444 arranged on a side of the carriage 440 can be turned to move the clamp 460 back and forth along the carriage 440 or a carriage portion/feature of the base plate. In other words, the release 442 can operate as a coarse adjustment mechanism for the position of the clamp 460 relative to the base plate 420 and the actuator/knob 444 can operate as a fine adjustment mechanism for the position of the clamp 460 relative to the carriage 440.

Figure 40:
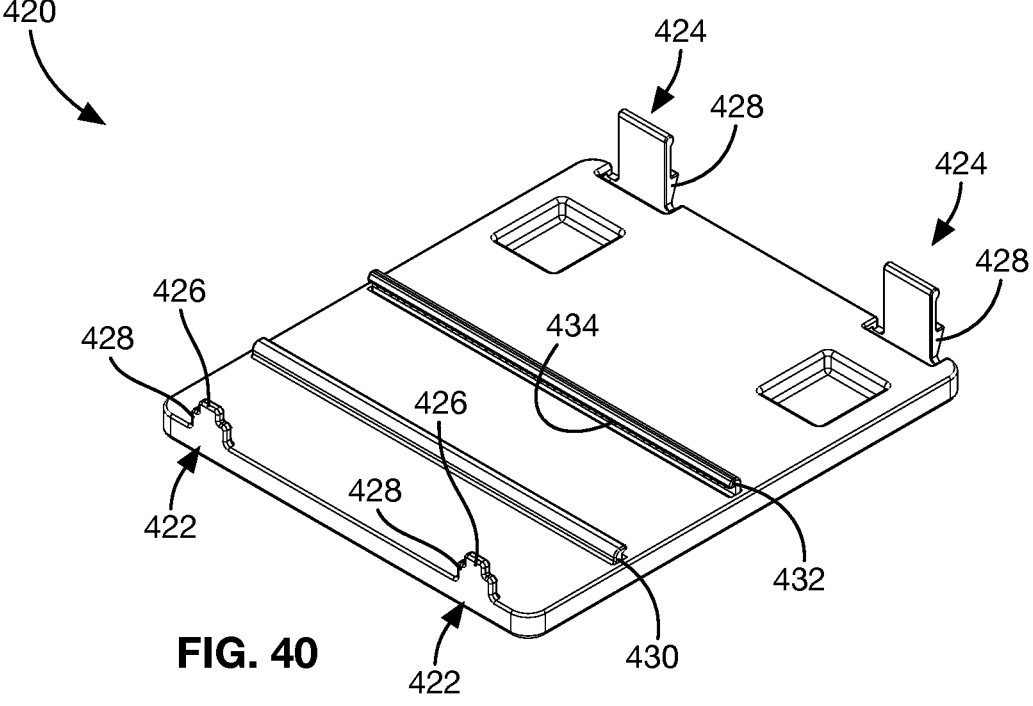
Figure 41:
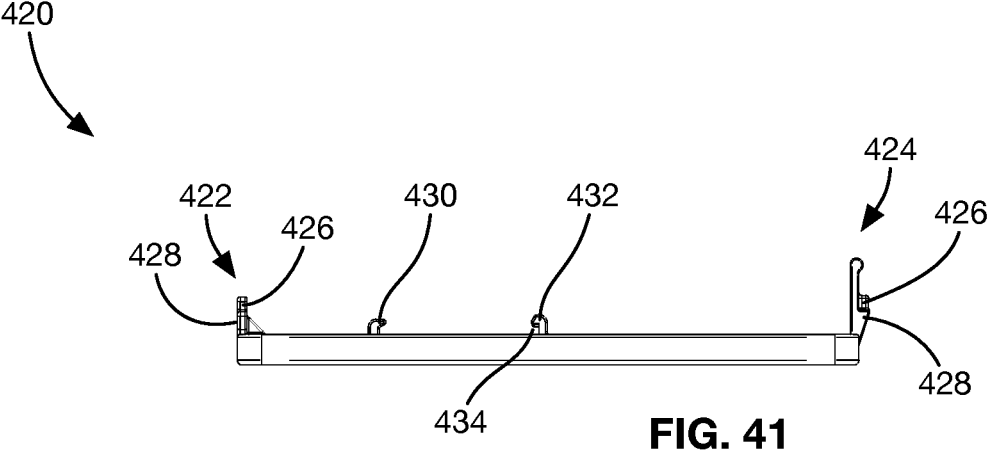
Figure 42:
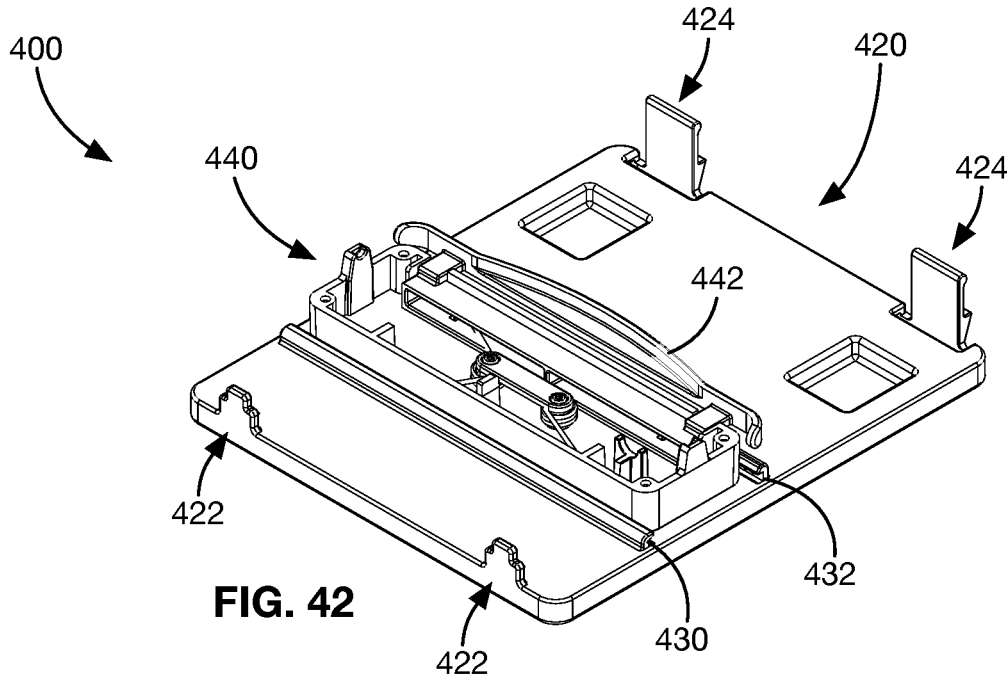
Figure 43:
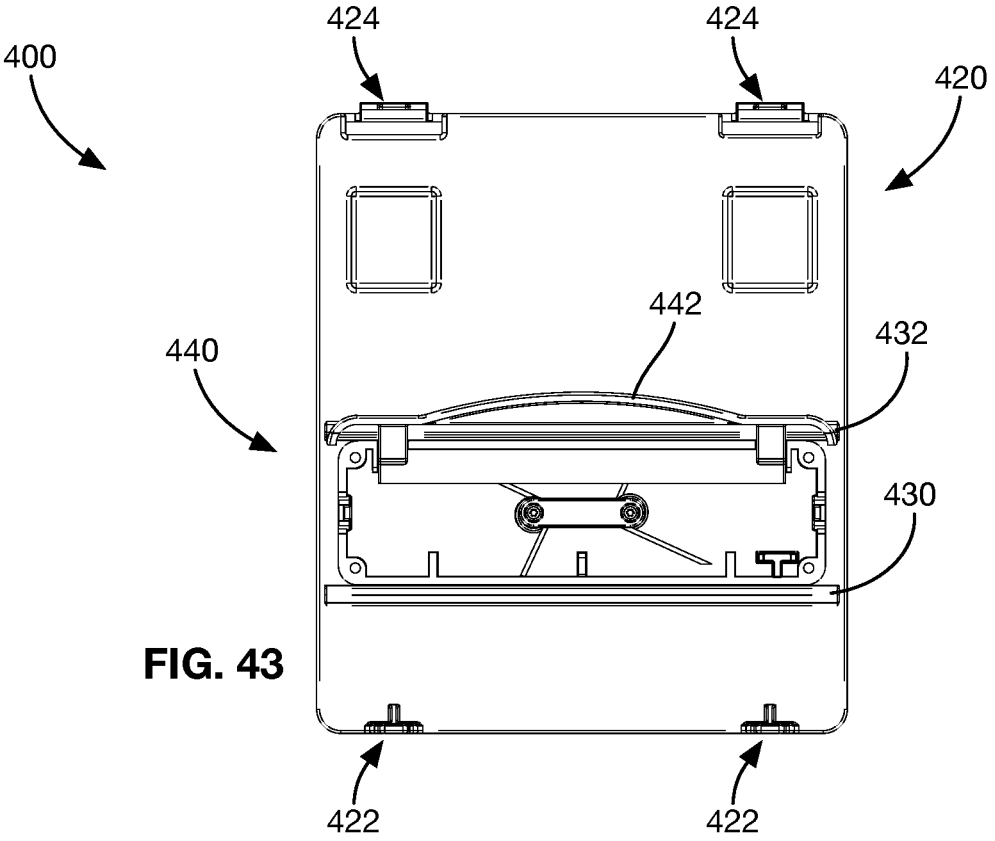
Figure 44:
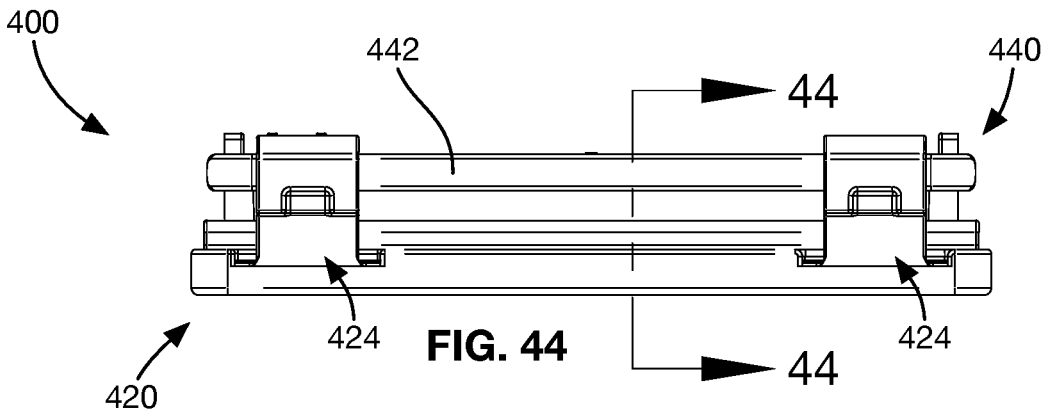

Referring now to FIGS. 40-41, an example base plate 420 is shown. Like the base plate 320, in some implementations, the base plate 420 has rigid tabs 422 and spring or flexible tabs 424 for attaching to the table 200. The tabs 422, 424 include alignment portions 426 that fit in the gaps 216 of the side walls 212 of the table 200 and retention shoulders 428 that fit underneath the latching protrusions 214 of the side walls 212 of the table 200. The base plate 420 is assembled to the table 200 by first inserting the alignment portions 426 of the rigid tabs 422 into the gaps 216 between the latching protrusions 214 of the side walls 212 so that the shoulders 428 of the rigid tabs 422 are retained by the latching protrusions 214. The other side of the base plate 420 is then pressed downward so that the alignment portions 426 and shoulders 428 of the flexible tabs 424 snap into the latching protrusions 214 of the opposite side wall 212. The flexible tabs 424 can include a ramp or inclined portion to provide a smoother engagement with the latching protrusions 214.

In some implementations, to remove the base plate 420 from the table 200, the upper ends of the flexible tabs 424 are pressed inward until the shoulders 428 are released from beneath the latching protrusions 214 to enable the base plate 420 to be lifted upward and removed from the table 200. Other removal or release mechanisms are also possible.

In one example, sufficient space is provided between the base plate and table 200 so that a sterile barrier, such as a drape, can be provided between the two. That is, a sterile barrier can be laid on top of the table 200 before the base plate 420 is snapped into place between the side walls 212 of the table 200. Like the base plate 320 shown in FIGS. 13 and 35, the base plate 420 is configured to attach the stabilizing device 400 to one or more tables 200 described above and shown in FIGS. 10-12.

Figure 45:
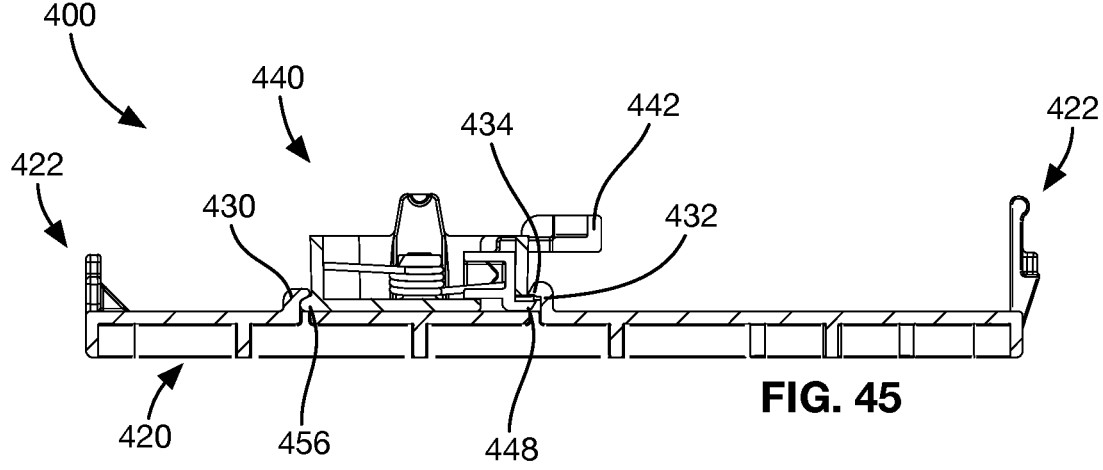
Figure 46:
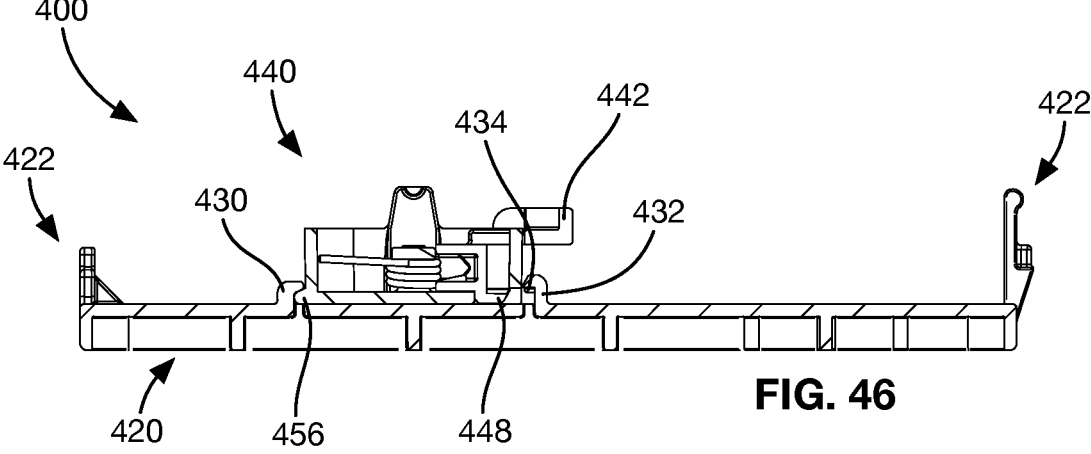
Figure 47:
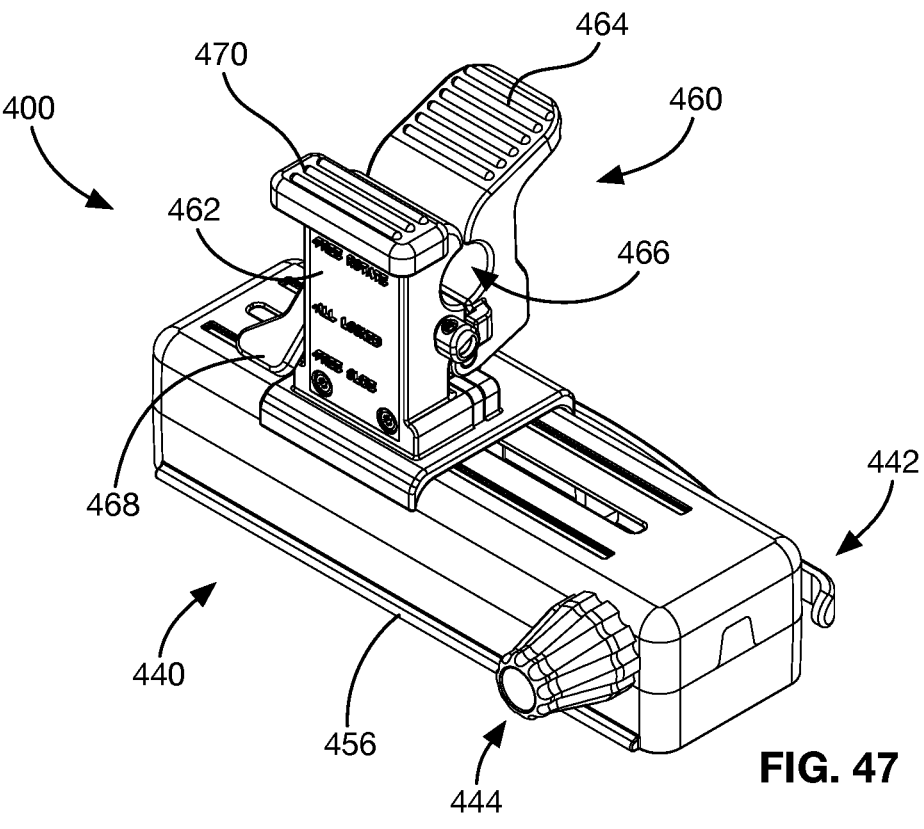
Figure 48:
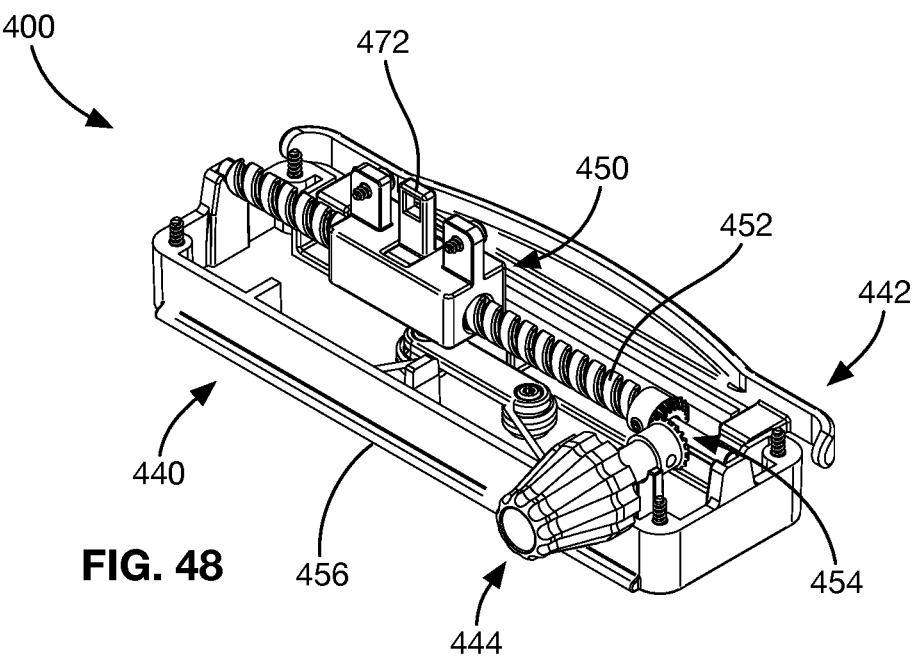
Figure 49:
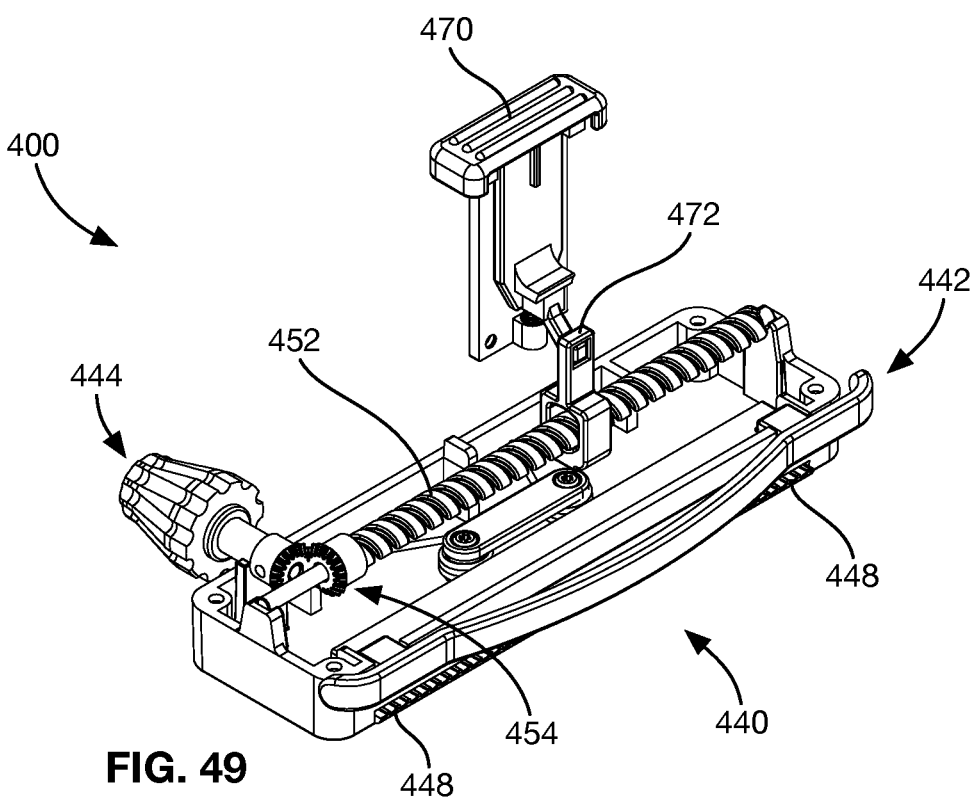
Figure 50:
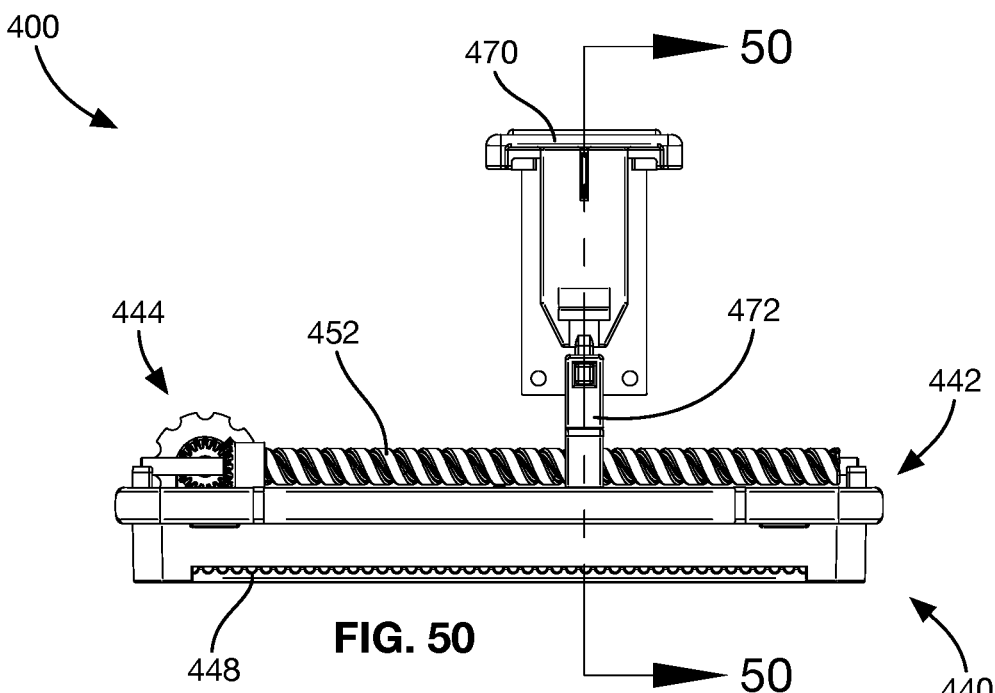

As can be seen in FIGS. 45 and 46, in some implementations, the carriage 440 is moveably and removably attached to the base plate 420 by a first mounting rail 430 and a second mounting rail 432 and latched in place. The first and second mounting rails 430, 432 extend across the base plate 420 and are spaced apart by the width of the carriage 440 and each include a recess for receiving retaining features of the carriage 440—i.e., a retaining lip 456 that engages the first mounting rail 430 and a latch 448 that engages the second mounting rail 432. The latch 448 is opened by the release button or bar 442. The second mounting rail 432 also includes locking teeth 434 extending downward from the upper surface of the recess for engaging and meshing together with corresponding teeth extending upward from the latch 448 to prohibit longitudinal movement of the carriage 440 once the second mounting rail 432 has been engaged by the latch 448.

Referring now to FIGS. 42-58, various views of the carriage 440 and clamp 460 and mechanisms thereof are shown. In particular, FIGS. 42-46 show the latch mechanism in greater detail. The carriage 440 can be attached or moved to any position on the mounting rails 430, 432 by depressing the release button 442 to retract the latch 448 (See FIGS. 49 and 50) out of the recess of the second mounting rail 432. This retracting disengages the teeth of the latch 448 from the teeth 434 (See FIG. 40) of the second mounting rail 432 so that the carriage 440 can be removed from or moved along the base plate 420.

The latch 448 can optionally be biased to a closed position by a biasing member, such as, for example, a spring, shape memory material, or an elastic member. The latch 448 can also include a beveled bottom edge so that the carriage 440 can be attached to the base plate 420 by inserting the retaining lip 456 in the recess of the first mounting rail 430 and then pressing down on the carriage 440 to snap the carriage 440 onto the second mounting rail 432—that is, by causing the latch 448 to open via the application of force against the inclined portion. Once past the second mounting rail 432, the latch 448 springs closed and engages the latch recess and locking teeth 434. Once attached, a rough or coarse adjustment of the position of the carriage 440 can be made by depressing the release button 442 to move the latch 448 out from the recess of the second mounting rail 432 to disengage the teeth of the latch 448 from the locking teeth 434 to free the carriage 440 to be moved along the mounting rails 430, 432.

Referring now to FIGS. 47-58, the carriage 440 is shown fully assembled (FIG. 47) and with various components removed to show the fine adjustment mechanism for adjusting the position of the clamp 460 relative to the carriage 440. FIGS. 47-58 also show a multi-function or selection actuator or lever 468 and release 470 for interacting with the same. The fine adjustment actuator or knob 444 is attached to a set of bevel gears 454 for translating the rotation of the knob 444 into rotation of a worm drive or gear 452. The worm drive or gear extends through a traveler 450 and a clutch 472 that extends through the center of the traveler 450. The traveler 450 extends above the carriage 440 to attached to the clamp 460. The clutch 472 includes a pin 474 (FIGS. 51-52) that fits within the groove of the worm drive 452 so that rotation of the worm drive 452 causes the clutch 472 and traveler 450—and, consequently, the clamp 460—to translate along the worm drive 452 and thus, the length of the carriage 440. While particular actuators may be described, these are just examples and other actuators could be used, e.g., buttons, knobs, latches, levers, etc.

The clamp 460 includes a fixed jaw 462 and a movable jaw 464 that is opened and closed by pivoting the movable jaw 464 relative to the fixed jaw 462. The movable jaw 464 is biased with a spring toward the fixed jaw 462 so that the clamp 460 remains in a closed condition unless opened by an application of an opening force to the movable jaw 464. The jaws 462, 464 of the clamp 460 come together to form an opening 466 for receiving the medical device (not shown) to be stabilized by the stabilizing device 400. In the closed position, the fixed and movable jaws 462, 464 might remain spaced apart so that the closing force of the clamp 460 is applied to the medical device to stabilize and prohibit rotation of the medical device. The clamp 460 is configured to receive and engage with a mounting portion of the traveler

450 so that the position of the clamp 460 can be adjusted along the length of the carriage 440 by rotation of the adjustment knob 444.

Figures 51, 52:
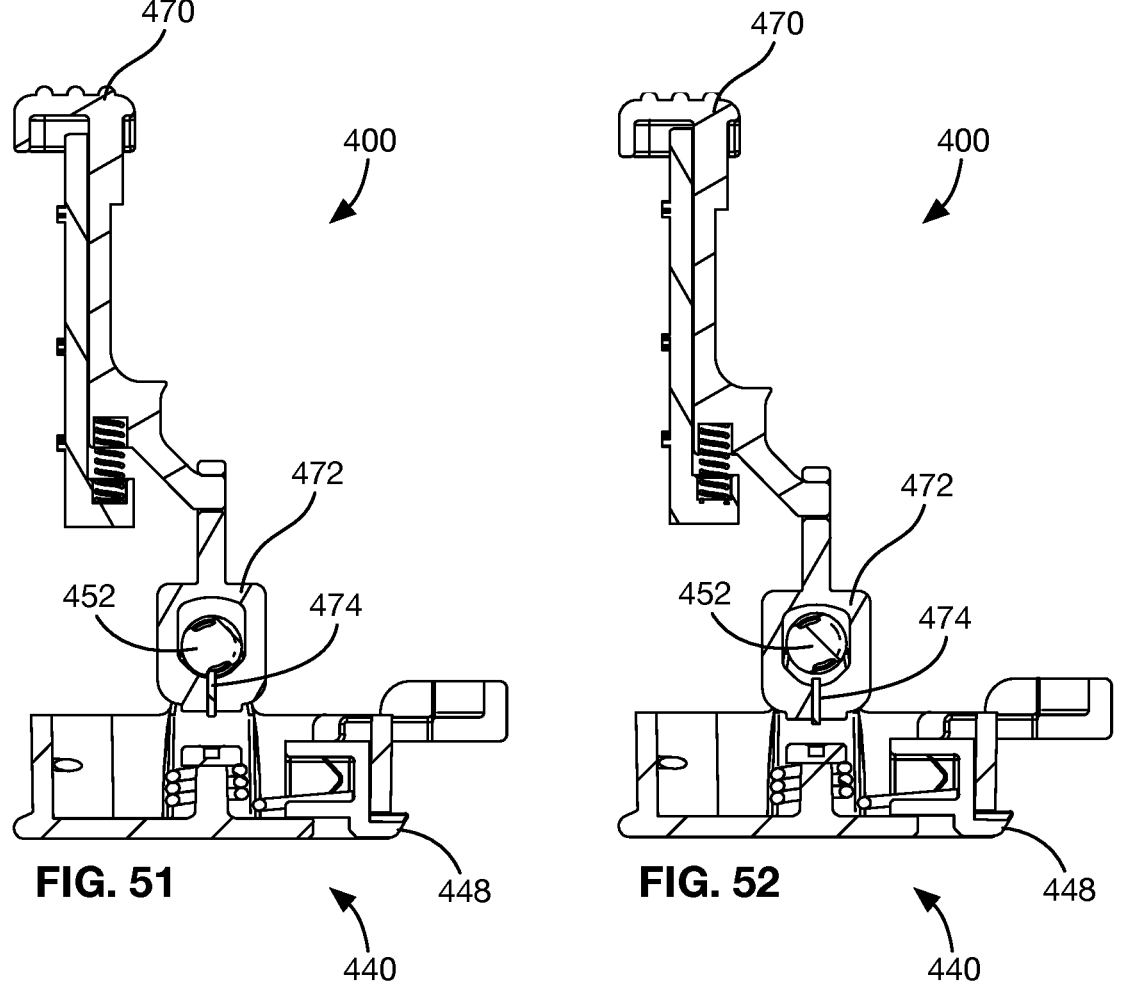

The fine adjustment mechanism can be disengaged to facilitate free adjustment of the position of the clamp 460 along the length of the carriage 440 without requiring repeated turning of the fine adjustment knob 444. As can be seen in FIGS. 49-52, the release button 470 engages the clutch 472. Referring to FIG. 52, pressing down on the release button 470 causes the clutch 472 to also move down, thereby disengaging the clutch pin 474 from the groove of the worm drive 452. While the release button 470 is held down, the clutch pin 474 remains disengaged from the worm drive 452 so that the clamp 460 can be moved along the carriage 440. The release button 470 is biased in an upward direction so that removing the actuation force from the release button 470 allows the release button 470 and clutch 472 to move upward, thereby re-engaging the groove of the worm drive 452 with the clutch pin 474 (See FIG. 51). If the clutch pin 474 is not aligned with the groove of the worm drive 452, the clamp 460 can be moved laterally or the worm drive 452 can be rotated by rotation of the fine adjustment knob 444 until the clutch pin 474 slips into place.

Referring now to FIGS. 53-58, an example multi-function or selection lever 468 is shown in greater detail. The selection lever 468 can be moved into three different positions that each correspond to a different operating state of the clamp 460 and carriage 440 mechanisms. The selection lever 468 can include retaining features, such as a ball detent (e.g., in FIGS. 57-58), to hold the selection lever 468 in each position. Other actuators are also possible.

Figures 53, 54:
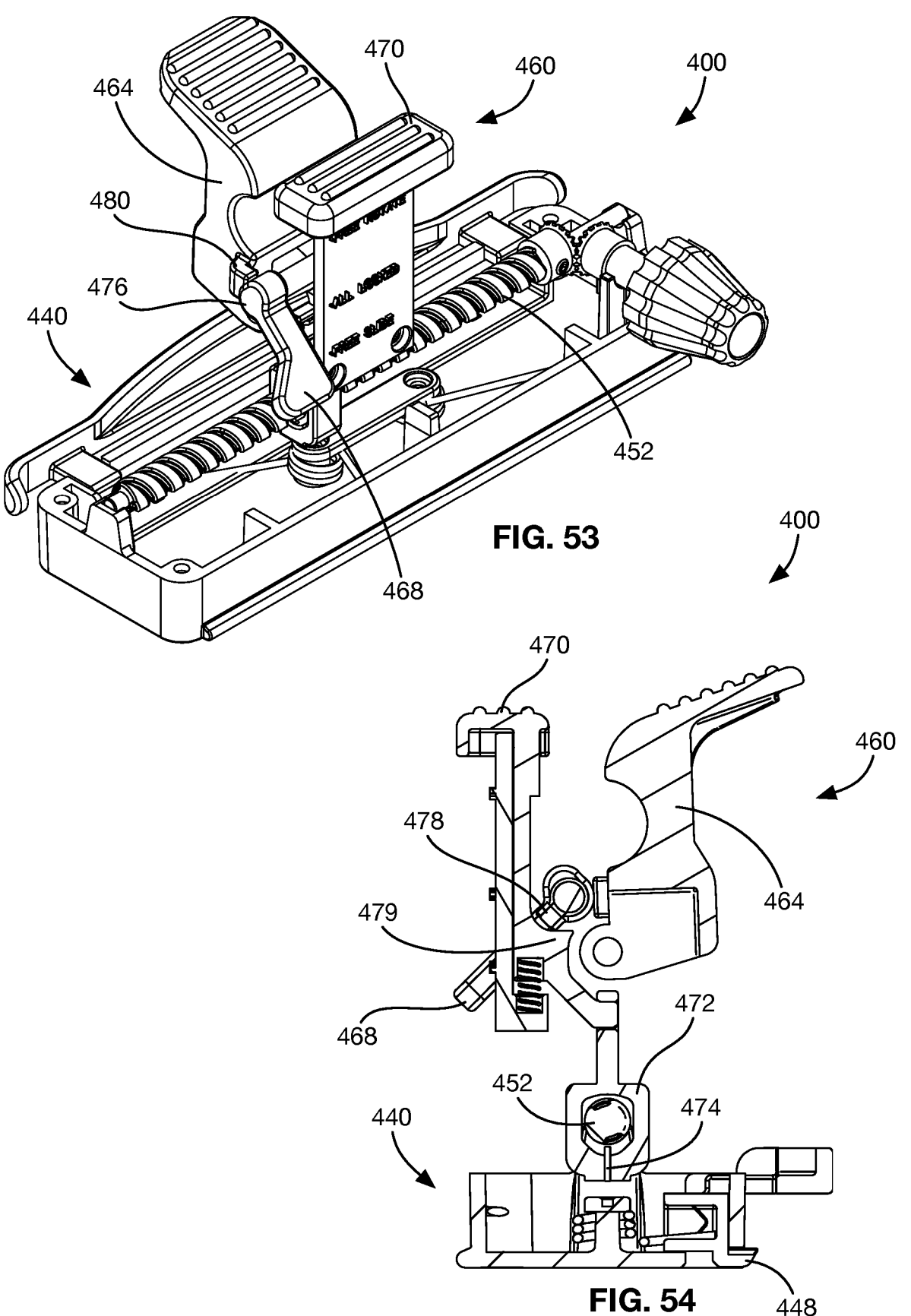

Moving the lever 468 downward into the "free slide" position, shown in FIGS. 53-54 causes a cam portion 478 (e.g., a screw head in the illustrated example) to engage a protrusion or shelf 479 that is connected to the release button 470, thereby causing the release button 470 to move downward. The downward movement of the release button 470 disengages the fine adjustment mechanism so that the clamp 460 can be moved freely from along the length of the carriage 444. Thus, when the selection lever 468 is moved into the free slide position, the lever 468 remains in the free slide position and the clutch pin 474 remains disengaged from the worm drive 452 until the selection lever 468 is moved back into the neutral or "all locked" center position shown in FIGS. 55-56. In one example, the clamp is in the closed position when the selection lever 468 is in the in the free slide position.

Figures 55, 56:
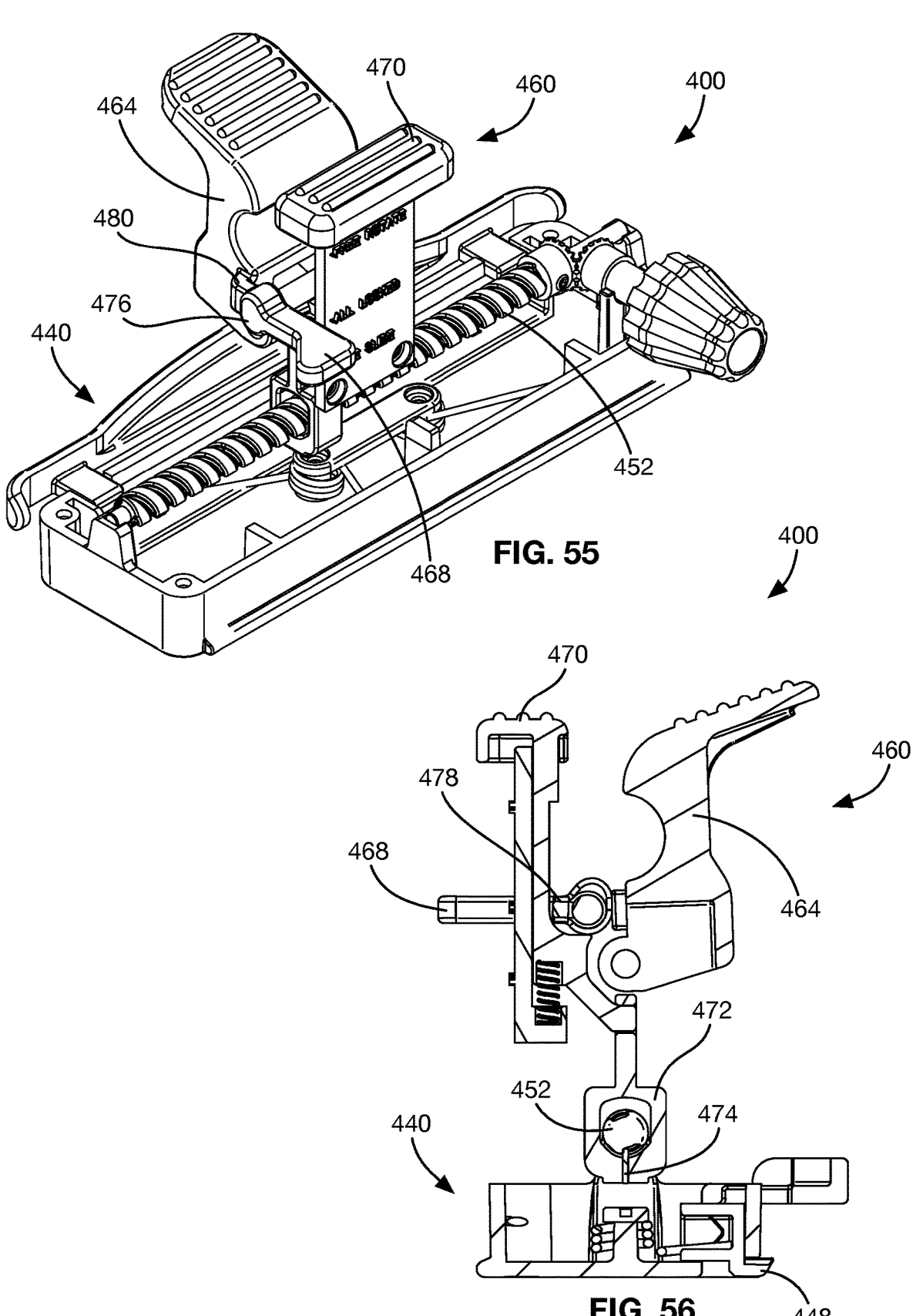

In the all-locked position, the cam portion 478 is rotated out of the way so that the clutch 472 can be moved upward by a spring, thereby engaging the worm drive 452 with the clutch pin 474 (See FIG. 56). In the "all locked" position, the clutch pin 474 remains engaged with the worm drive 452 unless overridden by actuation of the release button 470. As such, rotation of the worm drive 452 translates the clamp 460 along the length of the carriage 440. In one example, the clamp is in the closed position when the selection lever 468 is in the in the free slide position. From the "all locked" position, the selection lever 468 can be moved further upward to a "free rotate" position.

Figures 57, 58:
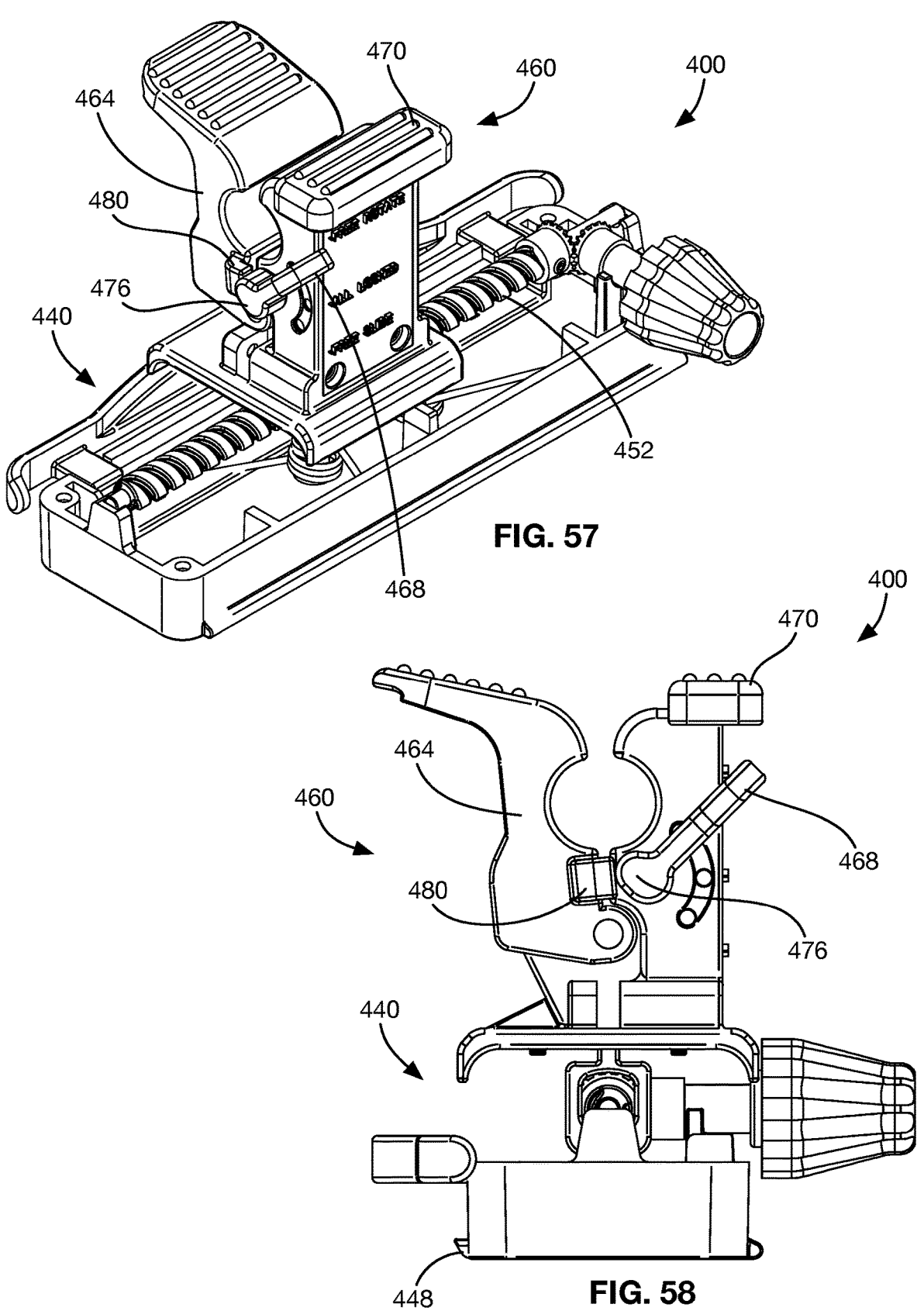
Figures 59, 60:
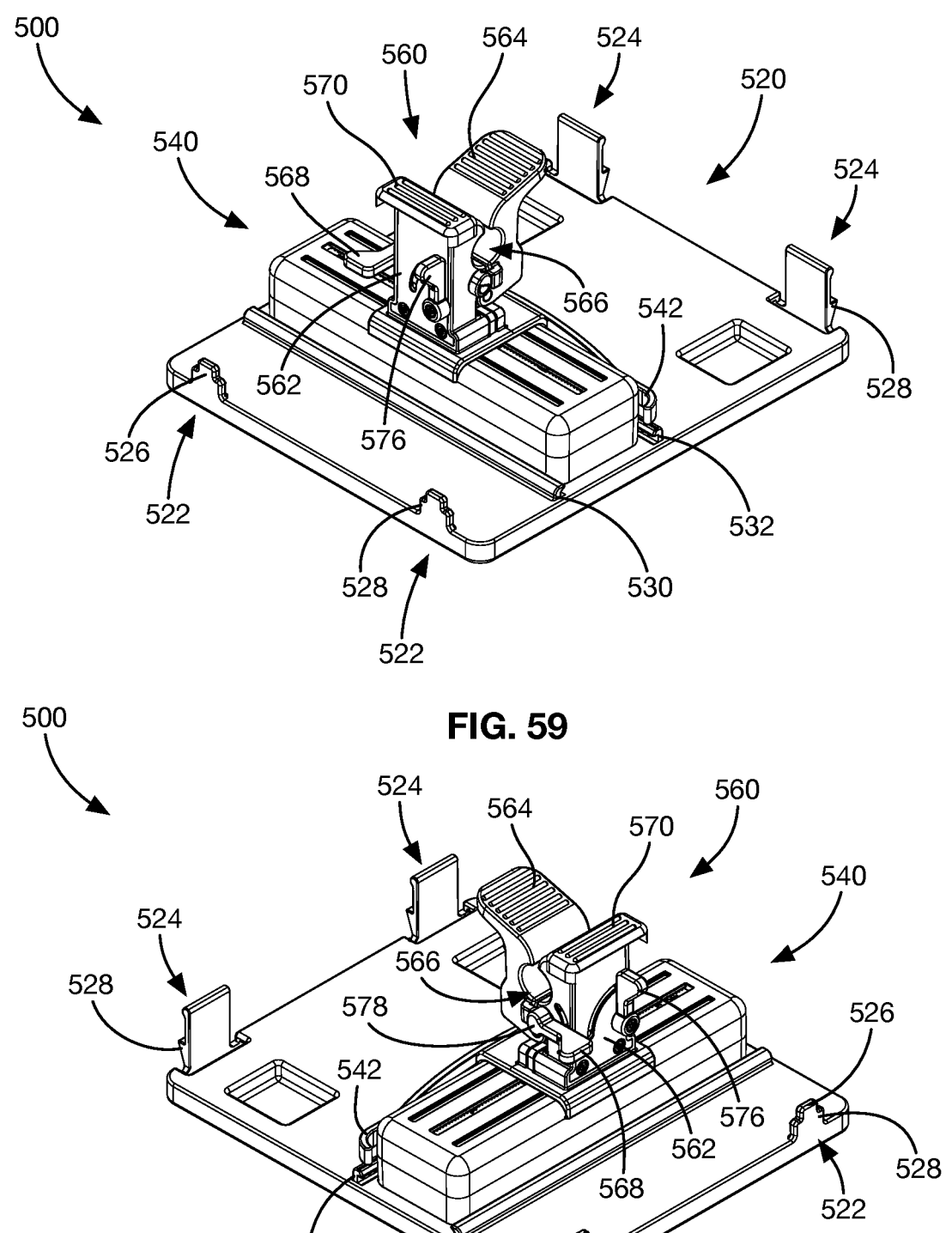
FIGS. 59-75 show various views of components of an example of a stabilizer for holding a delivery device used to implant an implantable prosthetic.
Figure 61:
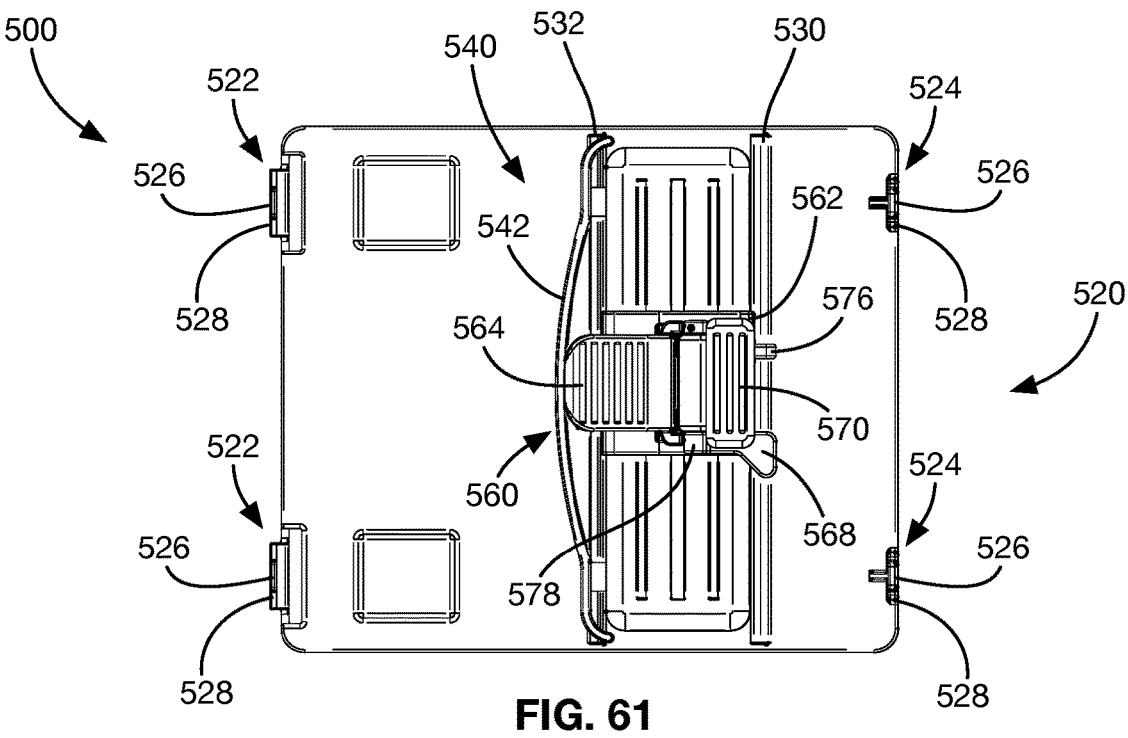
Figure 62:
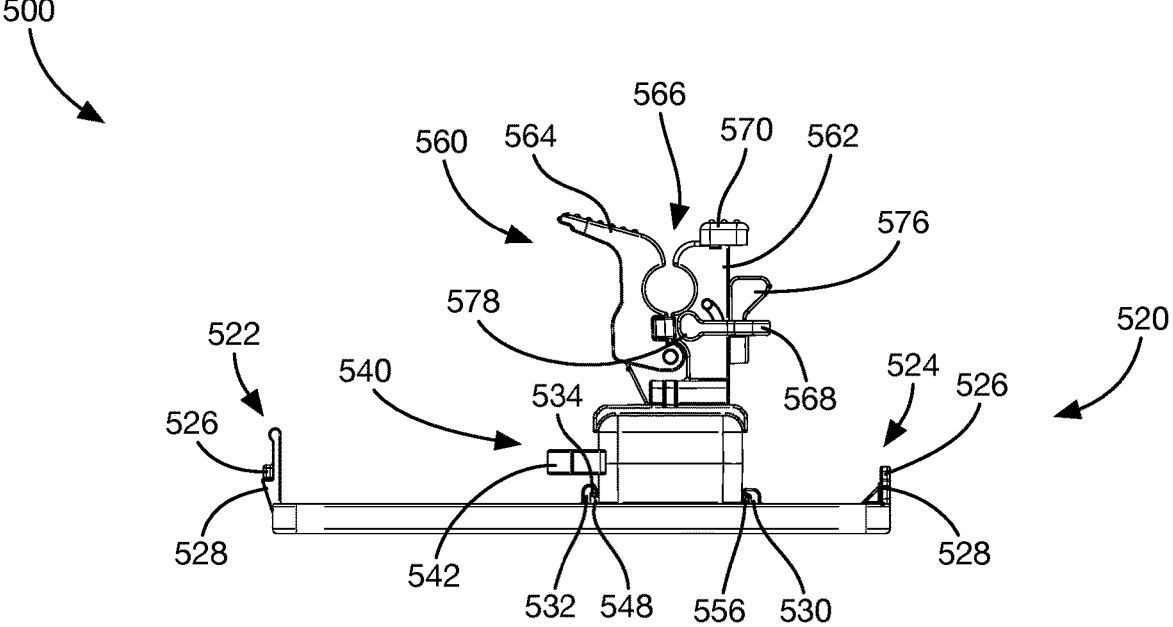
Figure 63:
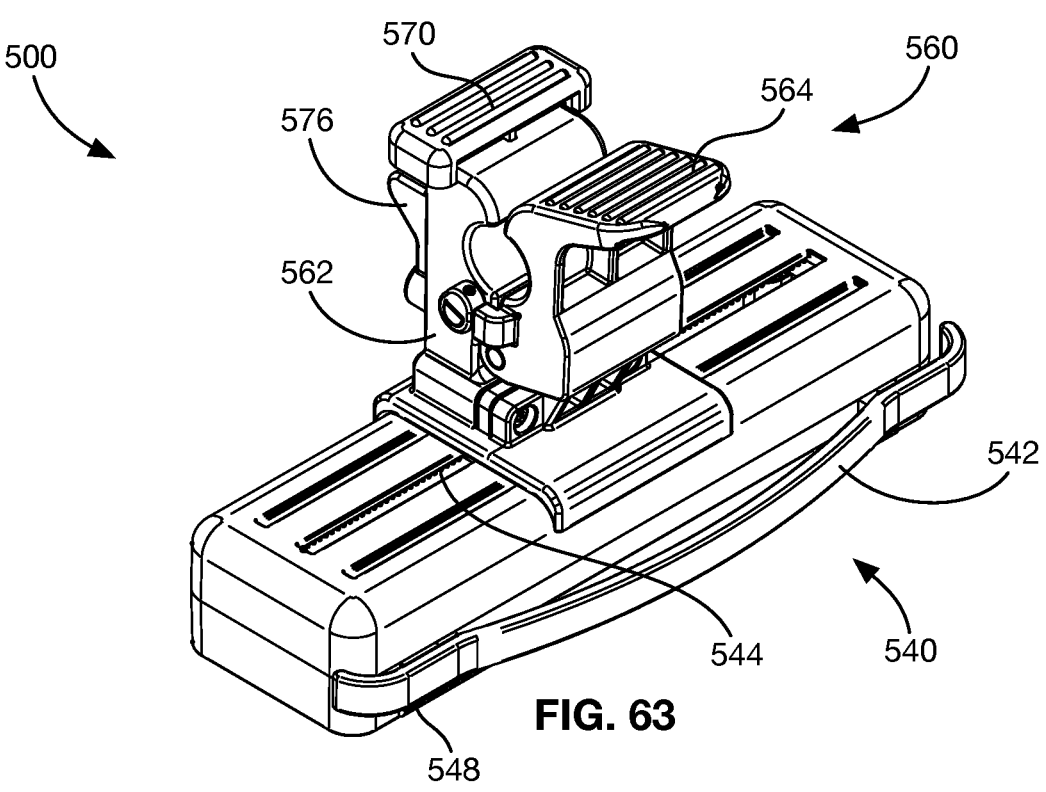
Figure 64:
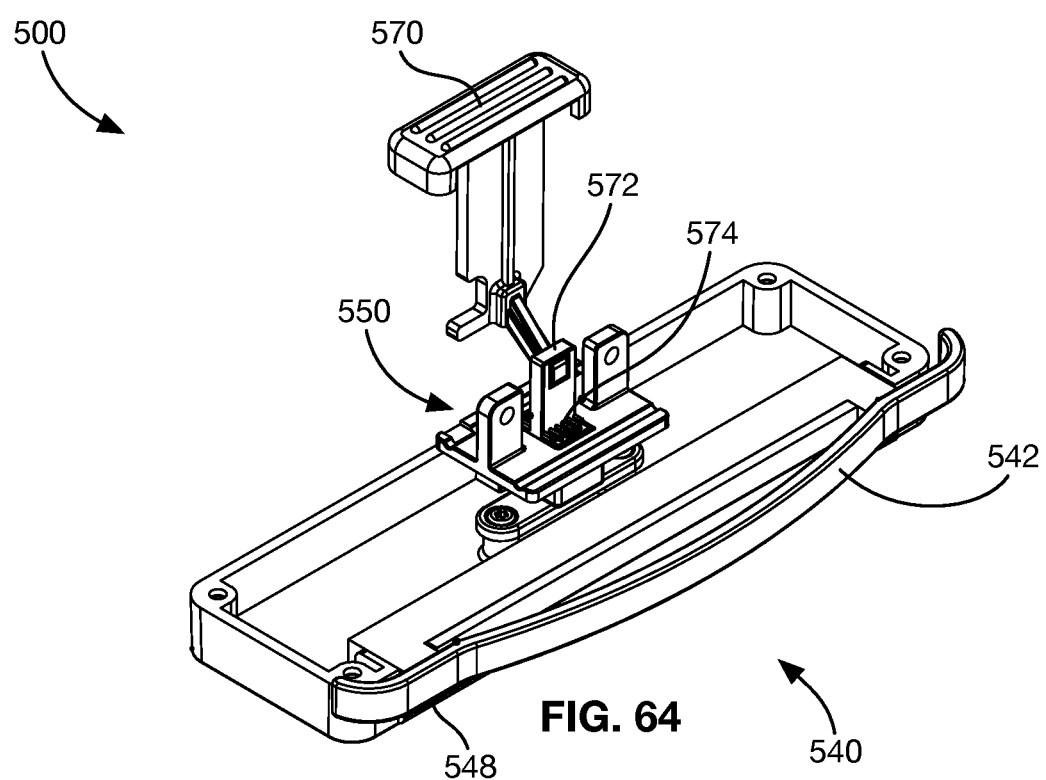

Referring to FIGS. 57 and 58, in the "free rotate" position, a cam portion 476 of the selection lever 468 engages an actuation portion 480 of the movable jaw 464. This engagement causes the movable jaw 464 to pivot in the opening direction, thereby partially opening the clamp 460. This partial opening allows a medical device, such as a catheter, that is retained in the clasp to freely rotate. The clutch 472 is unaffected by the "free rotate" position of the selection lever 468 and remains engaged with the worm drive 452 unless released by actuation of the release button 470.

Referring now to FIGS. 59-75, an example of a stabilizing system or device 500 is shown. The stabilizing system/device 500 can include one or more of a base plate 520, a carriage 540 attached to the base plate 520 (or carriage portion/feature formed in or as part of the base plate), and one or more clamps 560. The one or more clamps can be attachable to the carriage 540. The stabilizing system/device 500 can incorporate any of the features of stabilizing systems or devices disclosed herein and can be made from any suitable material, such as metal or plastic.

Referring now to FIGS. 59-62, the stabilizing device 500 includes a release or release button 542 for releasing the carriage 540 from the base plate 520 for disassembly and/or for longitudinal movement of the carriage 540 along the base plate 520. A release 570 arranged at the top of the clamp 560 can be depressed to allow the clamp 560 to be moved back and forth along the carriage 540. In other words, the release 542 can operate as a coarse adjustment mechanism for the position of the clamp 560 relative to the base plate 520 and the release 570 can operates as a fine adjustment mechanism for the position of the clamp 560 relative to the carriage 540.

The base plate 520 can be the same as or similar to the base plate 420 described above. For example, the base plate 520 can have rigid tabs 522 and spring or flexible tabs 524 for attaching to the table 200 (See FIGS. 10-13). The tabs 522, 524 include alignment portions 526 that fit in the gaps 216 of the side walls 212 of the table 200 and retention shoulders 528 that fit underneath the latching protrusions 214 of the side walls 212 of the table 200. The base plate 520 is assembled to the table 200 by first inserting the alignment portions 526 of the rigid tabs 522 into the gaps 216 between the latching protrusions 214 of the side walls 212. The shoulders 528 of the rigid tabs 522 are retained by the latching protrusions 214. The other side of the base plate 520 is then pressed downward so that the alignment portions 526 and shoulders 528 of the flexible tabs 524 snap into the latching protrusions 214 of the opposite side wall 212. The flexible tabs 524 can include a ramp or inclined portion to provide a smoother engagement with the latching protrusions 214.

To remove the base plate 520 from the table 200, the upper ends of the flexible tabs 524 are pressed inward until the shoulders 528 are released from beneath the latching protrusions 214 to enable the base plate 520 to be lifted upward and removed from the table 200. Sufficient space is provided between the base plate 520 and table 200 so that a sterile barrier, such as a drape, can be provided between the two. That is, a sterile barrier can be laid on top of the table 200 before the base plate 520 is snapped into place between the side walls 212 of the table 200. Like the base plate 320 shown in FIGS. 13 and 35, the base plate 520 can be configured to attach the stabilizing device 500 to one or more tables 200 described above and shown in FIGS. 10-12.

The carriage 540 is moveably and removably attached to the base plate 520 by a first mounting rail 530 and a second mounting rail 532 and latched in place. The first and second mounting rails 530, 532 extend across the base plate 520 and are spaced apart by the width of the carriage 540. Each mounting rail includes a recess for receiving retaining features of the carriage 540—i.e., a retaining lip 556 that engages the first mounting rail 530 and a latch 548 that engages the second mounting rail 532.

The latch 548 is identical to the latch 448 and associated mechanisms disclosed above. The latch 548 is opened by the release button or bar 542. The second mounting rail 532 also includes locking teeth 534 extending downward from the upper surface of the recess to for engaging and meshing together with corresponding teeth extending upward from the latch 548. The engagement of the teeth prevents movement of the carriage 540 along the base plate 520 once the second mounting rail 532 has been engaged by the latch 548.

Referring now to FIGS. 63-75, various views of examples of carriage 540, clamp 560, and mechanisms thereof are shown. In some implementations, the latch mechanism for latching the carriage 540 to the mounting rails 530, 532 of the base plate 520 is the same as or similar to the mechanism shown in FIGS. 42-46 and described in detail above. The carriage 540 can be attached or moved to any position on the mounting rails 530, 532 by actuating the release 542. Actuating the release 542 retracts the latch 548 out of the recess of the second mounting rail 532 to disengage the teeth of the latch 548 from the teeth of the second mounting rail 532. As a result, the carriage 540 can be removed from or moved along the base plate 520.

The latch 548 can optionally be biased to a closed position by a biasing member, such as, for example, a spring, shape memory material, elastic member, etc. The latch 548 can also include a beveled bottom edge so that the carriage 540 can be attached to the base plate 520 by inserting the retaining lip 556 in the recess of the first mounting rail 530 and then pressing down on the carriage 540 to snap the carriage 540 onto the second mounting rail 532—that is, by causing the latch 548 to open via the application of force against the inclined portion. Once past the second mounting rail 532, the latch 548 springs closed and engages the latch recess and locking teeth 534.

Once attached, a rough or coarse adjustment of the position of the carriage 540 can be made by actuating the release 542. This moves the latch 548 out from the recess of the second mounting rail 532 to disengage the teeth of the latch 548 from the locking teeth 534. As a result, the carriage 540 is free to be moved along the mounting rails 530, 532.

Optionally, in some implementations, the carriage can be formed in or as part of the base plate such that the rails 530, 532 are not necessary, and the clamp is moved within the carriage. The carriage need not be movable relative to the base plate in these implementations.

Referring now to FIGS. 63-71, the carriage 540 is shown fully assembled (FIG. 63) and with various components removed to show the mechanism for adjusting the position of the clamp 560 relative to the carriage 540. For example, the position of the clamp 560 relative to the carriage 540 can be adjusted using an actuator or free slide lever 576 and/or a release 570. Though specific examples, such as levers, buttons, or knobs may be described, various types of actuators could be used in their place.

Figures 65, 66, 67:
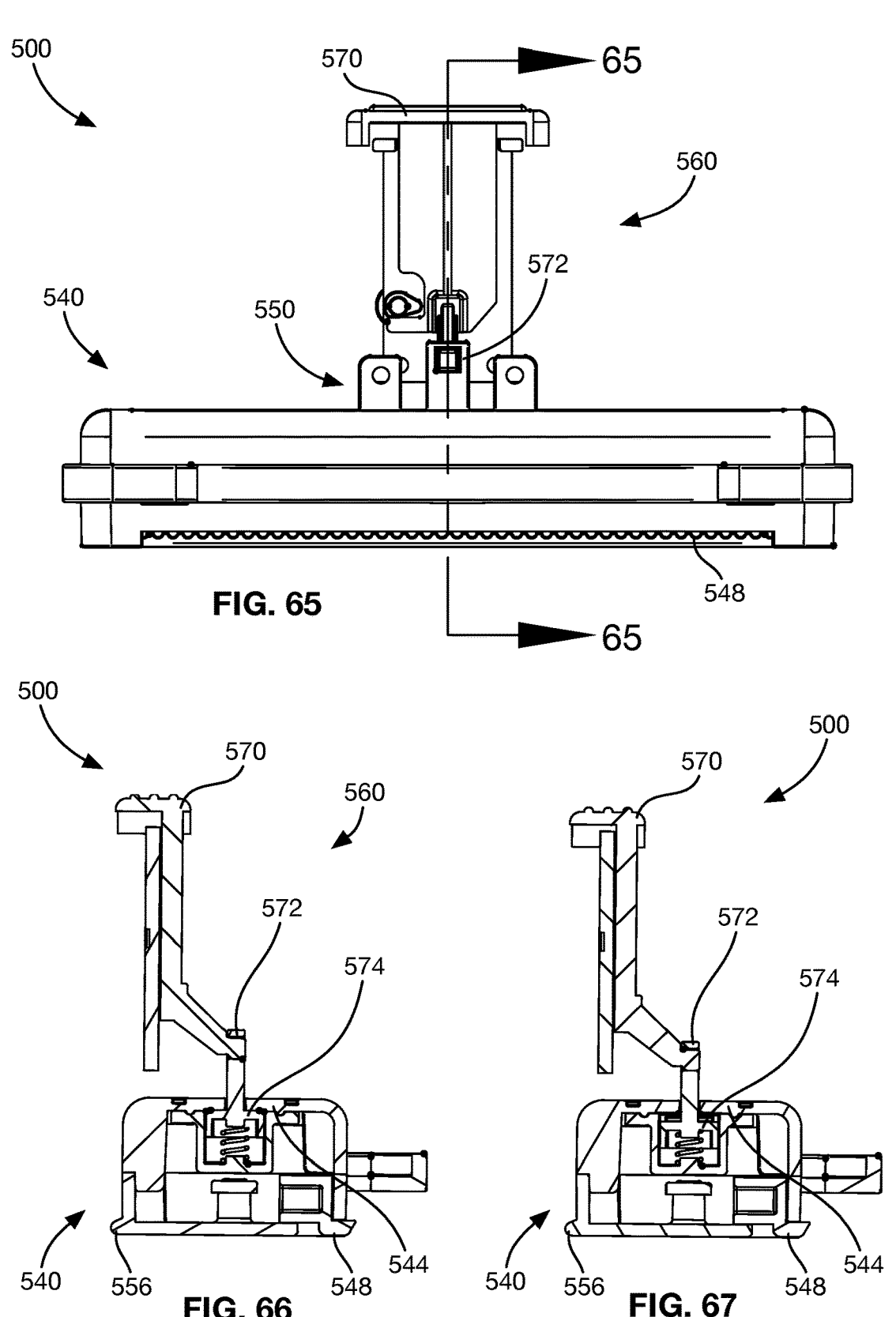
Figures 68, 69:
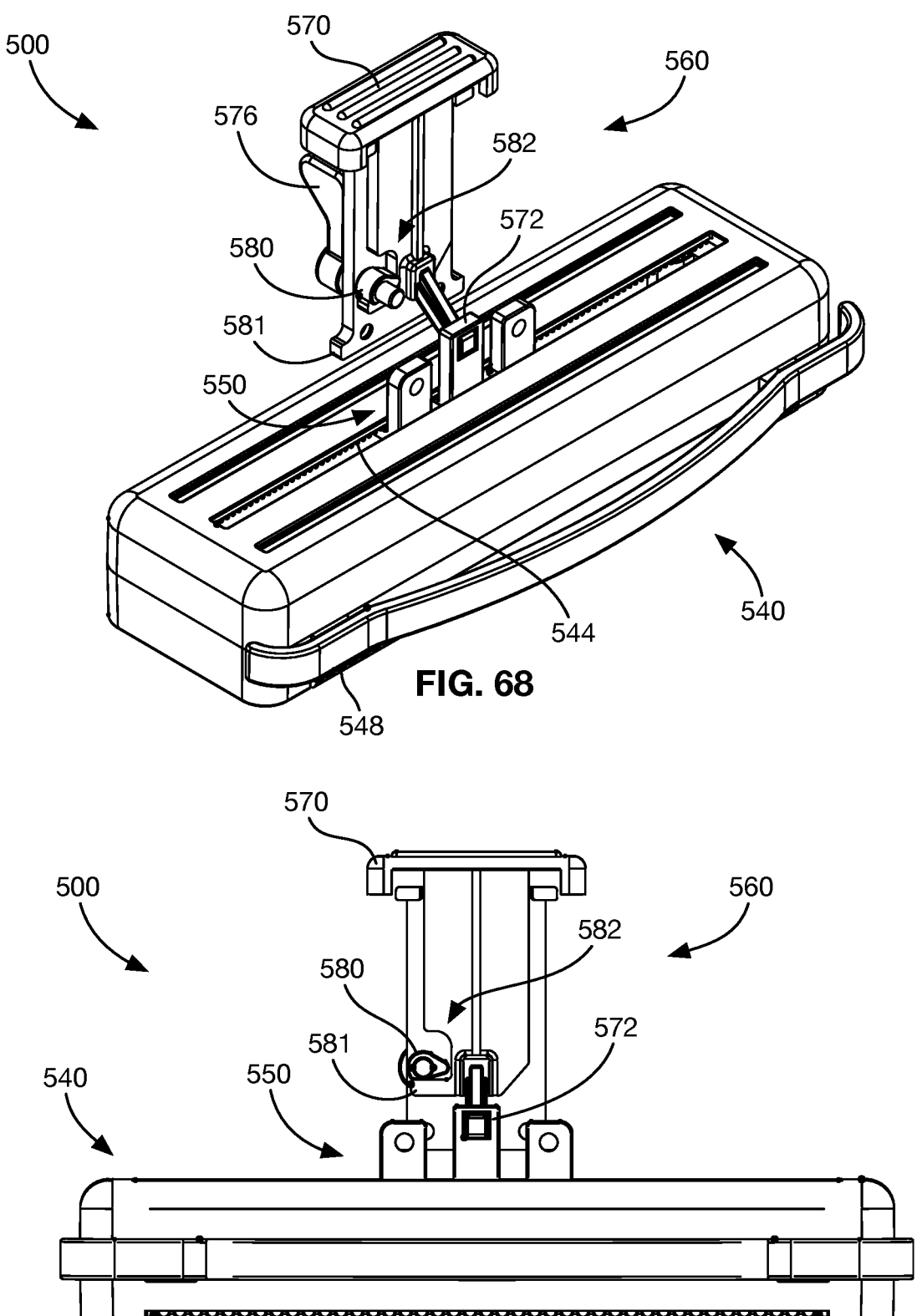
Figures 70, 71:
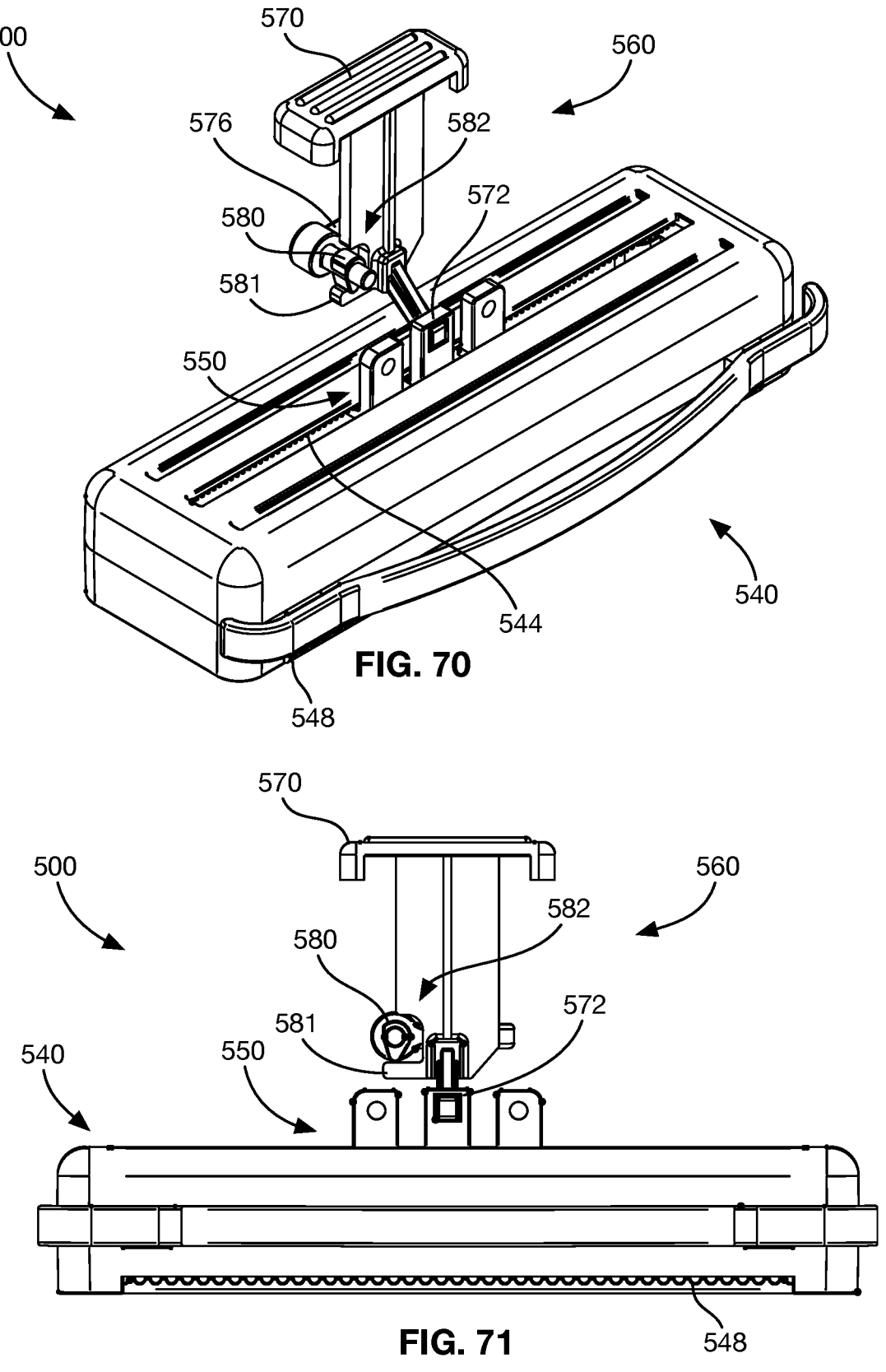
Figure 72:
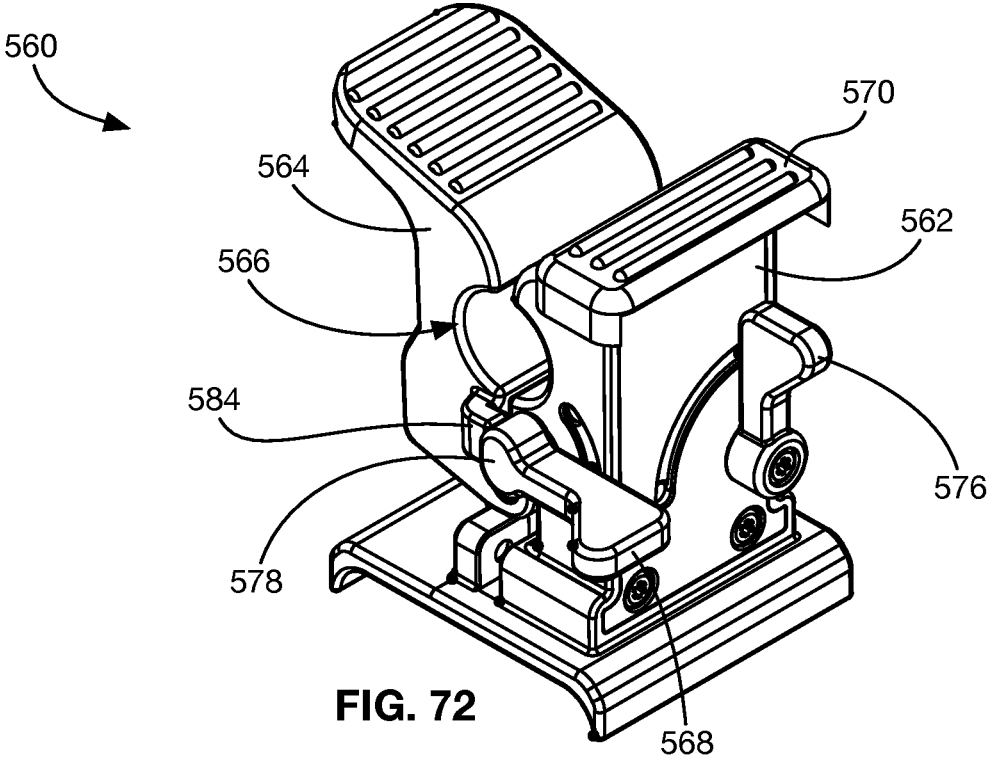
Figure 73:
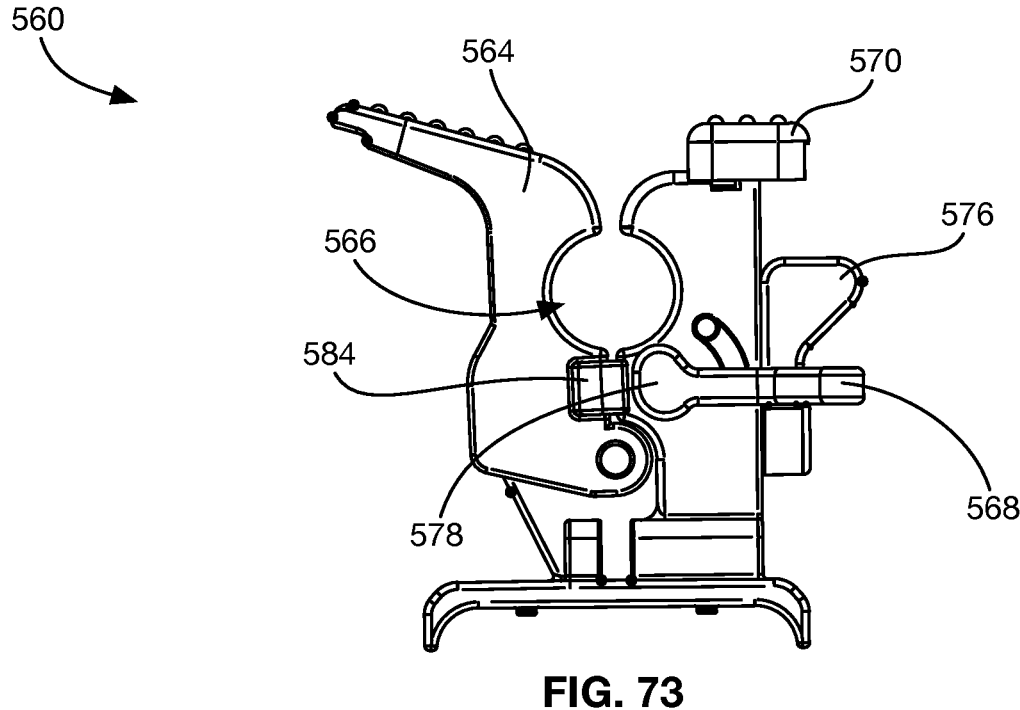

Referring to FIGS. 68 and 69, in some implementations, a traveler 550 extends above the carriage 540 for attachment to the clamp 560. When attached to the clamp 560, the traveler 550 secures the clamp 560 for movement along the top of the carriage 540. Referring to FIGS. 66 and 67, a clutch 572 extends through the center of the traveler 550. The clutch is biased upward to engage an inside top surface of the carriage 540. The clutch 572 includes an engagement portion 574 that includes teeth (See FIG. 64) extending upward to engage teeth 544 (See FIG. 70) arranged along the inside upper surface of the carriage.

Referring to FIGS. 72-75, an example clamp 560 includes a fixed jaw 562 and a movable jaw 564 that is opened and closed by pivoting the movable jaw 564 relative to the fixed jaw 562. The movable jaw 564 is biased with a spring toward the fixed jaw 562 so that the clamp 560 remains in a closed condition unless opened by an application of an opening force to the movable jaw 564. The jaws 562, 564 of the clamp 560 come together to form an opening 566 for receiving the medical device (not shown), such as a catheter, to be stabilized by the stabilizing device 500. In the closed position, the fixed and movable jaws 562, 564 might remain spaced apart so that the closing force of the clamp 560 is applied to the medical device to stabilize and prohibit rotation of the medical device. Similar clamps and/or features of this clamp 560 can be used for other clamps herein.

The clamp 560 is configured to receive and engage with a mounting portion of the traveler 550 so that the position of the clamp 560 can be adjusted along the length of the carriage 540 by actuating the release button 570 and sliding the clamp 560. As can be seen in FIGS. 64-71, the release button 570 engages the clutch 572 so that pressing down on the release button 570 causes the clutch 572 to also move down, thereby disengaging the engagement portion 574 from the teeth 544 of the carriage 540. While the release button 570 is held down, the engagement portion 574 remains disengaged from the teeth 544 so that the clamp 560 can be moved along the carriage 540. The release button 570 is biased in an upward direction so that removing the actuation force from the release button 570 allows the release button 570 and clutch 572 to move upward, thereby re-engaging the teeth 544 of the carriage 540 with the engagement portion 574. If the teeth of the engagement portion 574 are not aligned with the teeth 544 of the carriage 540, the clamp 560 can be moved longitudinally until the engagement portion 574 slips into place.

Referring now to FIGS. 68-71, an example of an actuator configured as a free slide or slide release lever 576 is shown in greater detail. The free slide lever 576 can be moved from a disengaged position to a free slide position. The lever 576 can include retaining features, such as a ball detent (e.g., in FIGS. 72-75), to hold the lever 576 in each position. Moving the lever 576 downward from the disengaged position (FIGS. 68-69) into the "free slide" position (FIGS. 70-71) causes a cam portion 580 to engage a shelf or projection 571 of an actuation portion 582 of the release button 570, thereby causing the release button 570 to move downward. The downward movement of the release button 570 disengages the engagement portion 574 so that the clamp 560 can be moved freely along the carriage 540. Thus, when the lever 576 is moved into the free slide position, the lever 576 remains in the free slide position and the engagement portion 574 remains disengaged from the teeth 544 until the lever 576 is moved back into the disengaged position shown in FIGS. 68-69.

Figure 74:
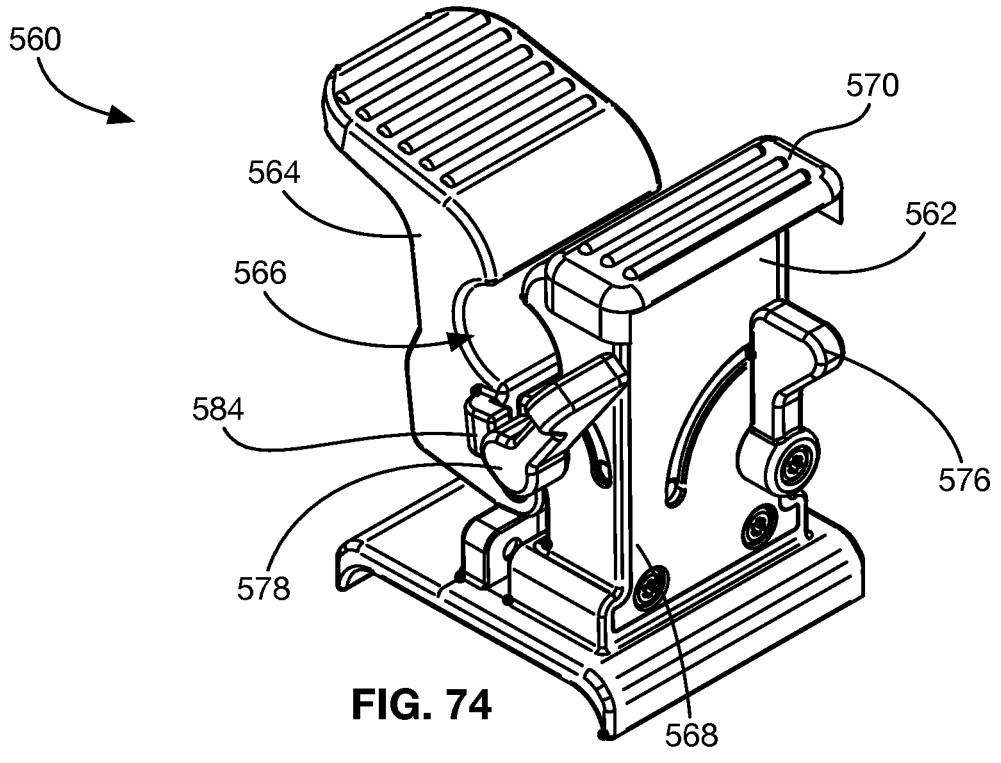
Figure 75:
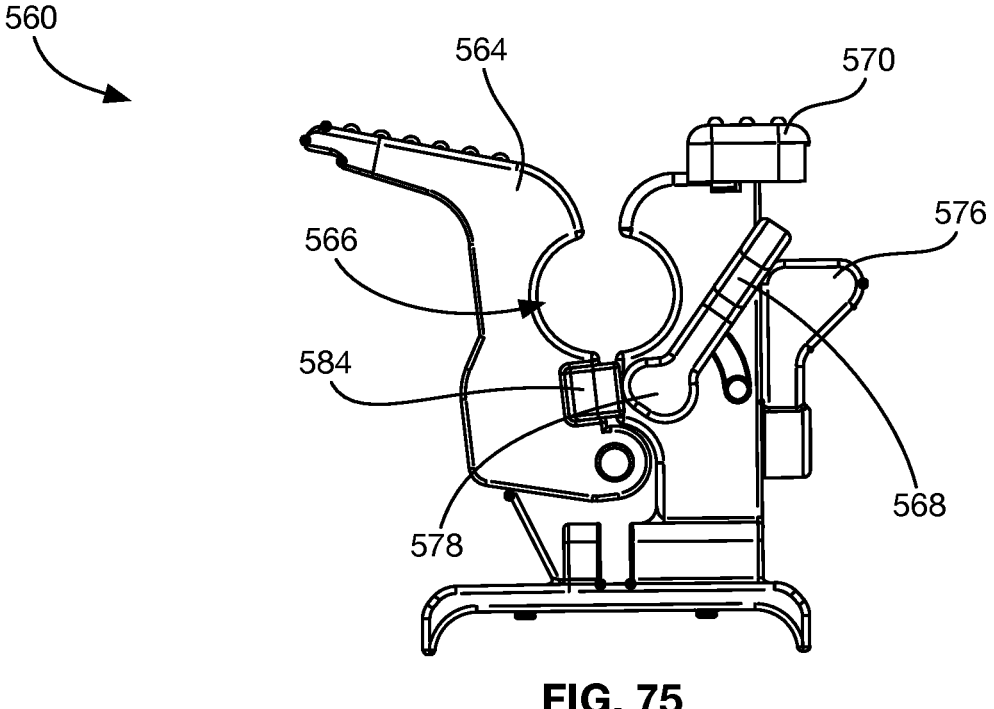
Figure 76:
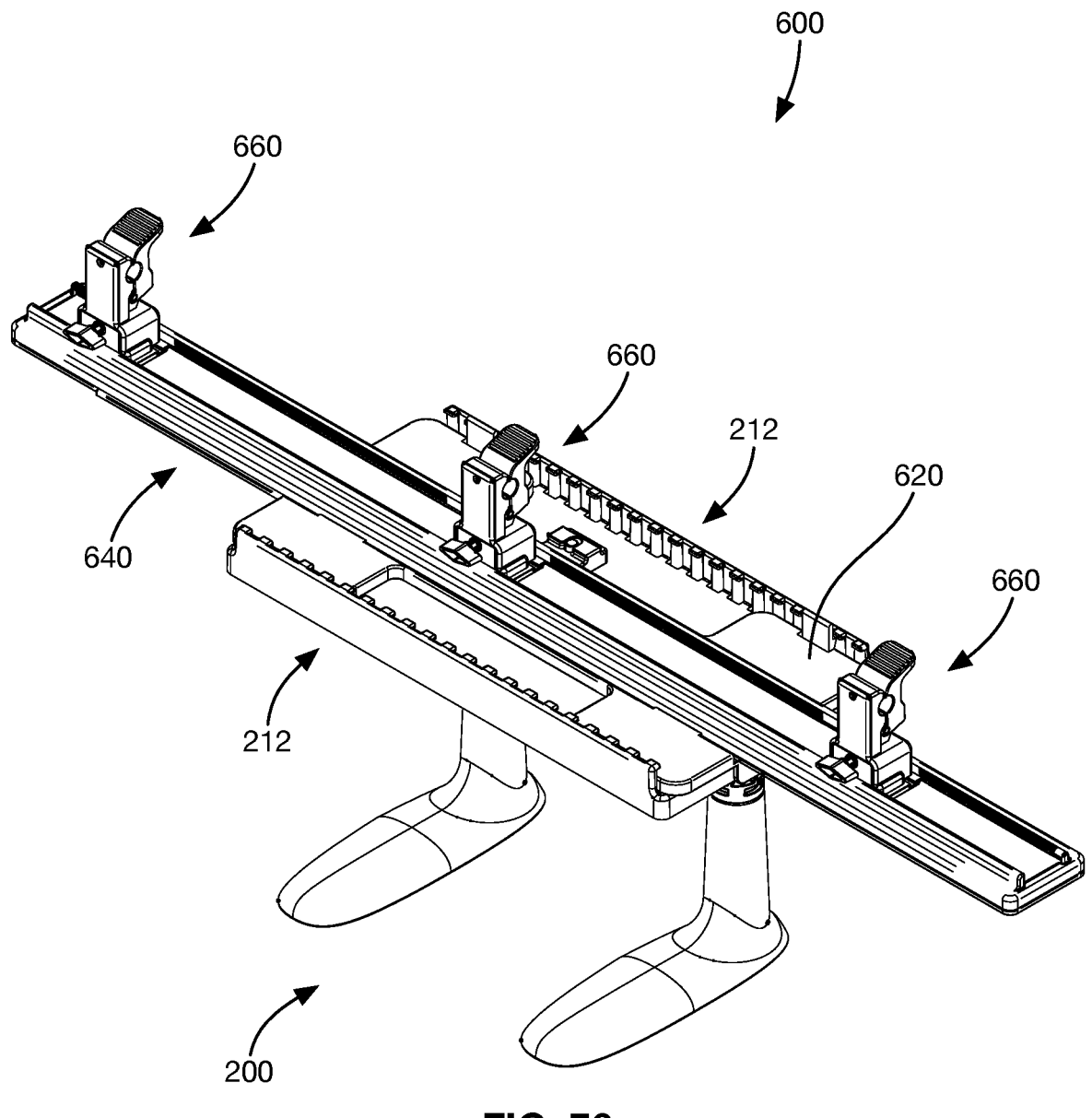
Figure 77:
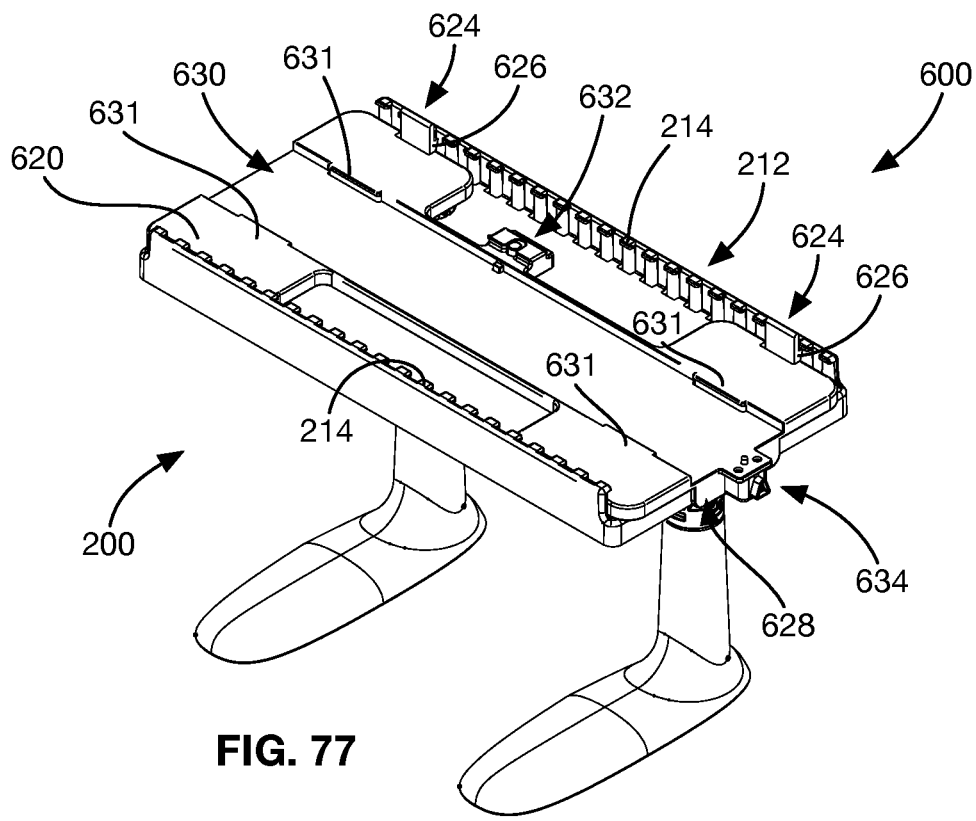
Figure 78:
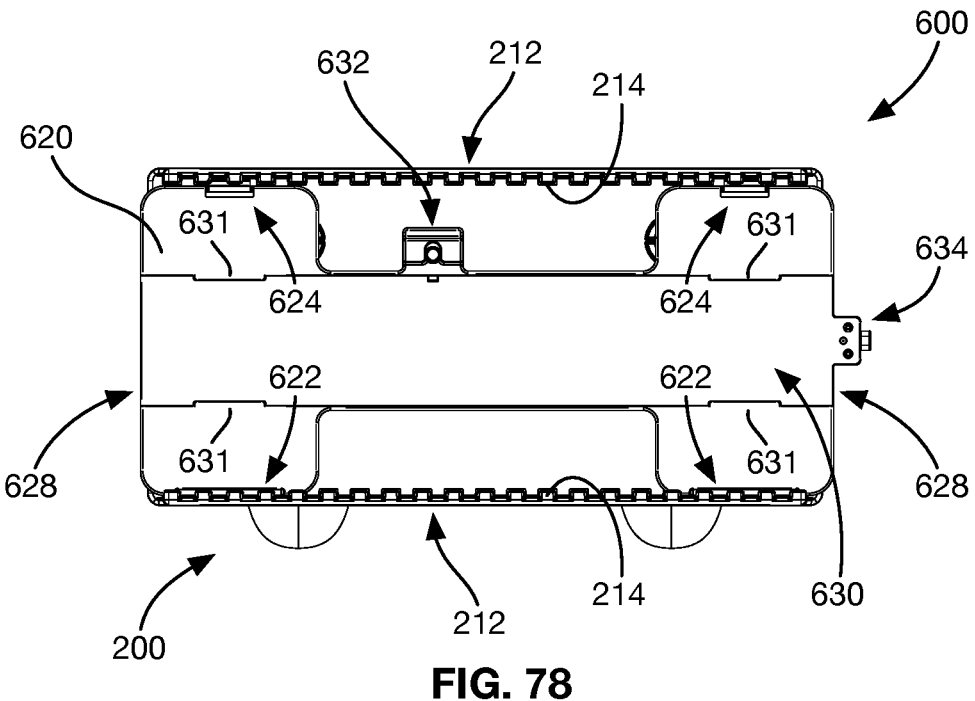
Figure 79:
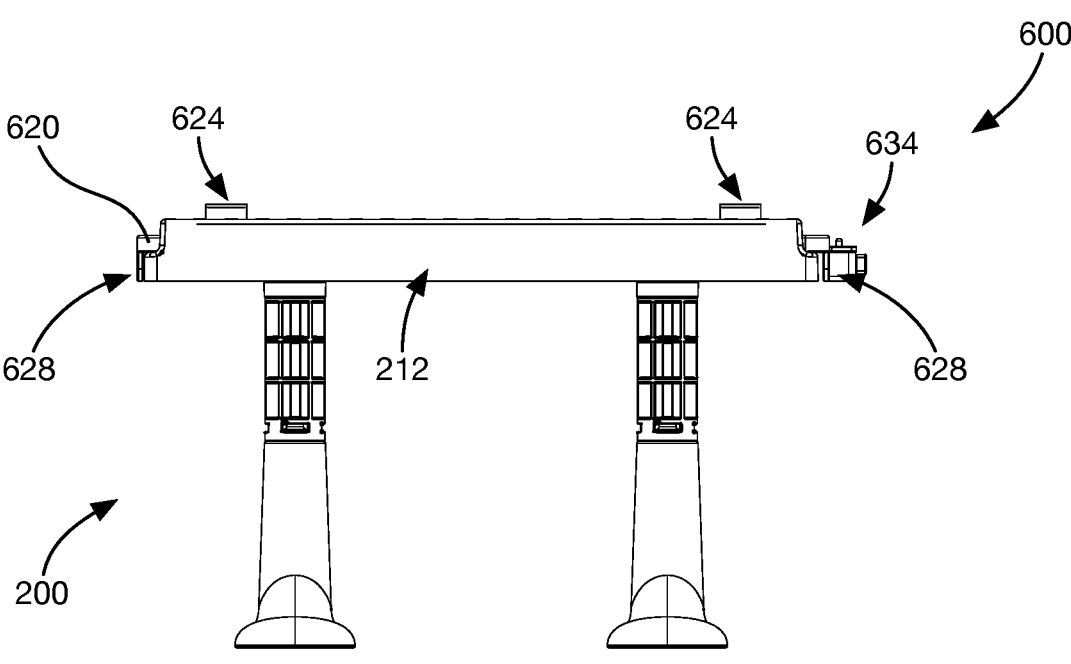
Figure 80:
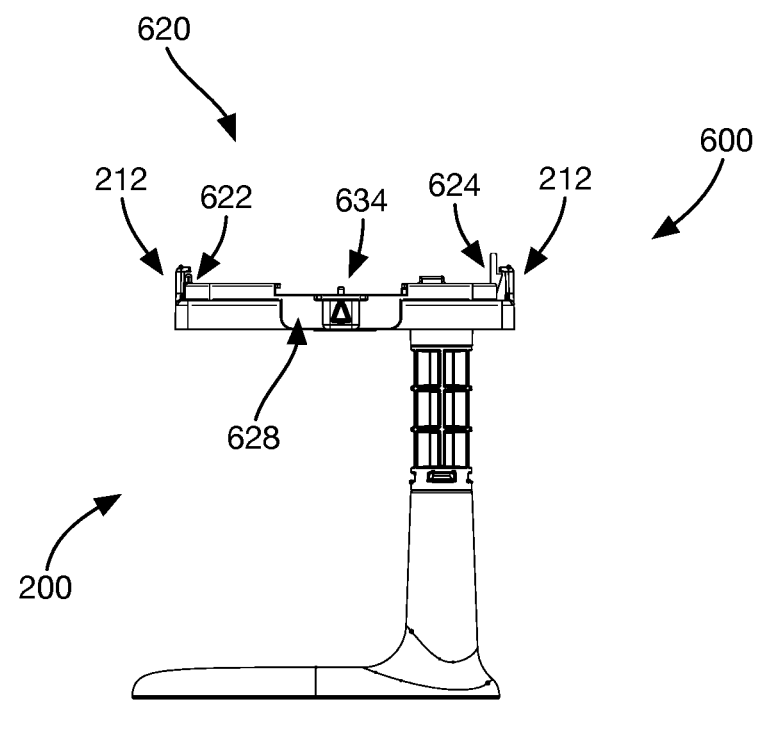

Referring now to FIGS. 72-75, an example actuator configured as a free rotate lever 568 is shown in greater detail. The free rotate lever 568 can be moved from a disengaged position (FIGS. 72-73) to a free rotate position (FIGS. 74-75). In the free rotate position, a cam portion 578 of the lever 568 engages an actuation portion 584 of the movable jaw 564. This engagement causes the movable jaw 564 to pivot in the opening direction, thereby partially opening the clamp 560 so that a medical device, such as a catheter, retained therein is able to freely rotate.

The free rotate lever 568 and the free slide lever 576 can be independently operated. As a result, the free rotate lever 568 and free slide lever 576 can be set to allow both free rotation of a medical device in the clamp and free sliding of the clamp on the carriage, set to allow free rotation of a medical device in the clamp, but fix the clamp on the carriage, set to fix the medical device in the clamp, but allow free sliding of the clamp on the carriage, or set to fix the medical device in the clamp and fix the clamp on the carriage.

Referring now to FIGS. 76-116, an example of a stabilizing system or device 600 is shown. In some implementations, the stabilizing system/device 600 can include one or more of a base plate 620, a carriage 640 attached to the base plate 620 (or a carriage portion or carriage feature formed in or as part of the base plate), and one or more clamps 660. The one or more clamps are attachable to the carriage 640. The stabilizing system/device 600 can incorporate any of the features of stabilizing systems or devices disclosed elsewhere herein and can be made from any suitable material, such as metal, plastic, polymers, fibers, combinations of materials, etc.

Referring now to FIGS. 77-94, an example base plate 620 is shown assembled to the table 200 and details of the mechanisms of the base plate 620 are shown in greater detail. The base plate 620 can be the same as or similar to the base plates 420, 520 described above. For example, in some implementations, the base plate 620 can include rigid tabs 622 and spring or flexible tabs 624 for attaching to the table 200. The rigid tabs 622 fit underneath the latching protrusions 214 of the side walls 212 of the table 200 and are wide enough to engage multiple latching protrusions 214. The flexible tabs 624 include retention shoulders 626 that also fit underneath the latching protrusions 214 of the side walls 212 of the table 200.

In some implementations, the base plate 620 also includes alignment tabs 628 extending downward from each end of the base plate 620 to align the base plate 620 on the table 200. Optionally, the rigid and/or flexible tabs 622, 624 can include alignment portions like the base plates 320, 420, 520 described above.

Figure 81:
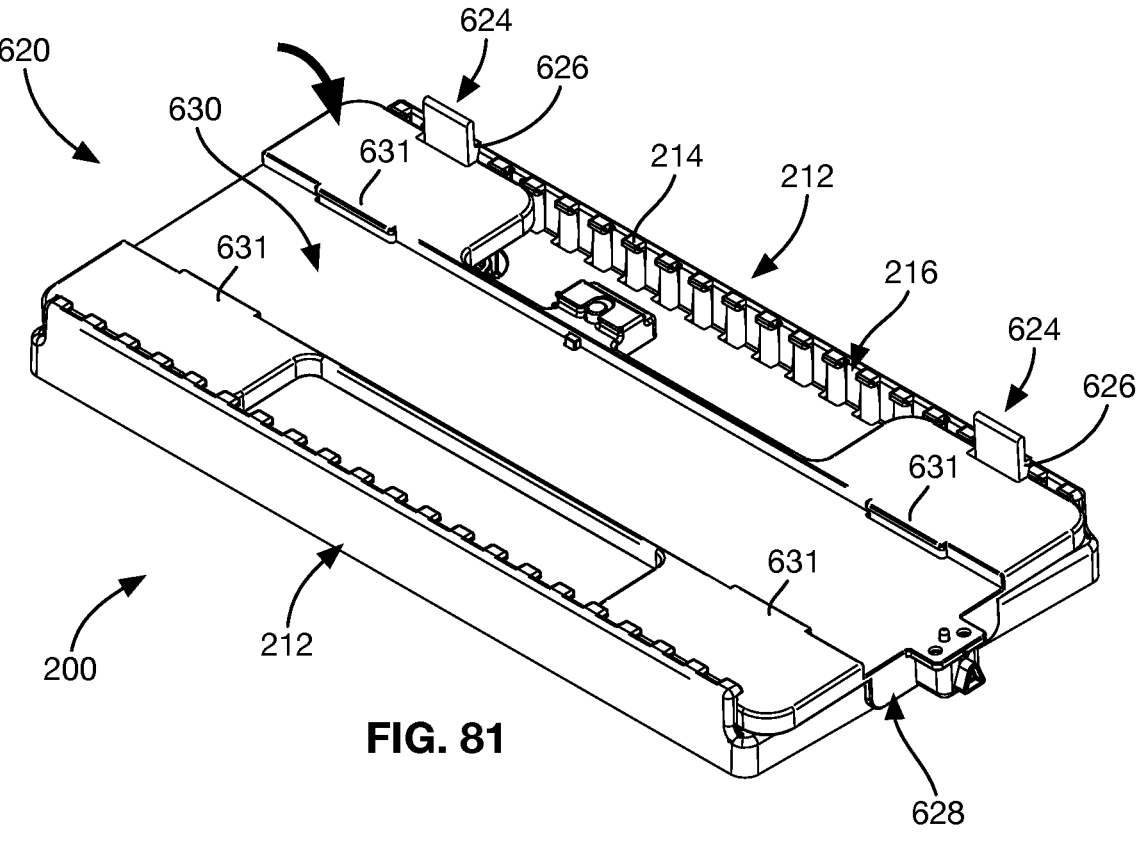
Figure 82:
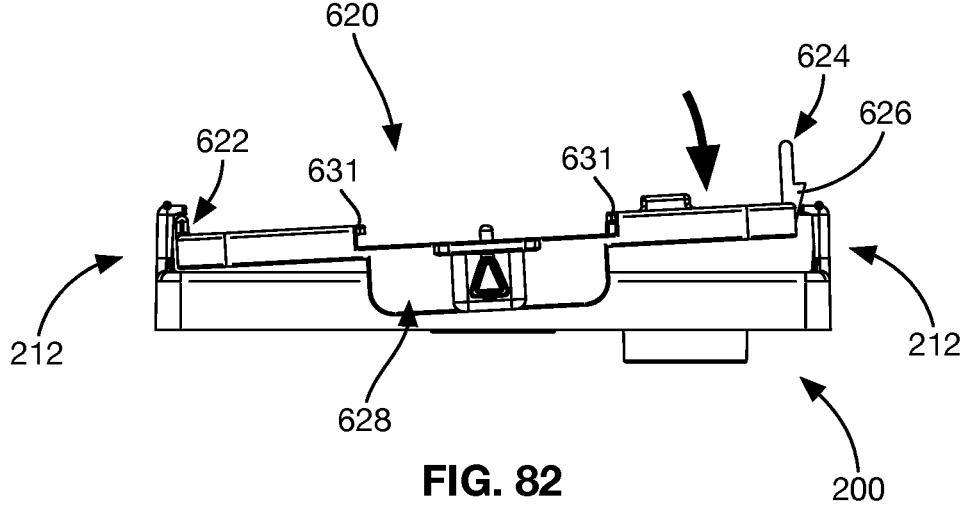
Figure 83:
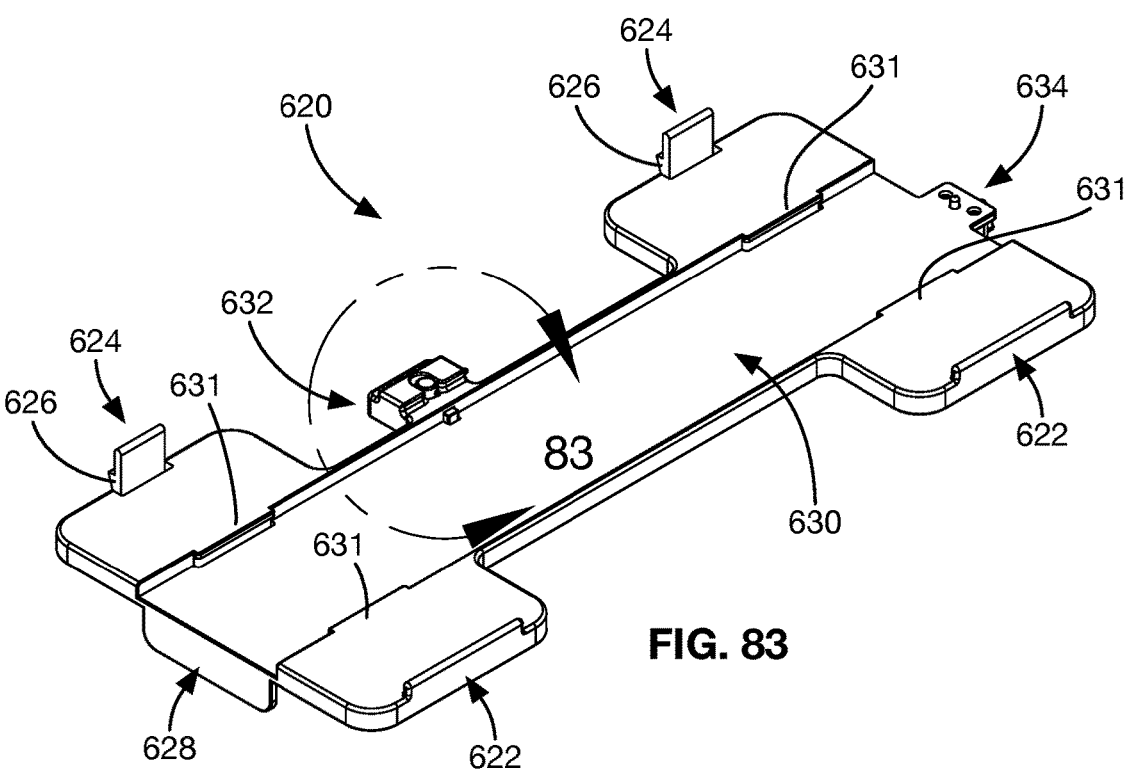
Figure 84:
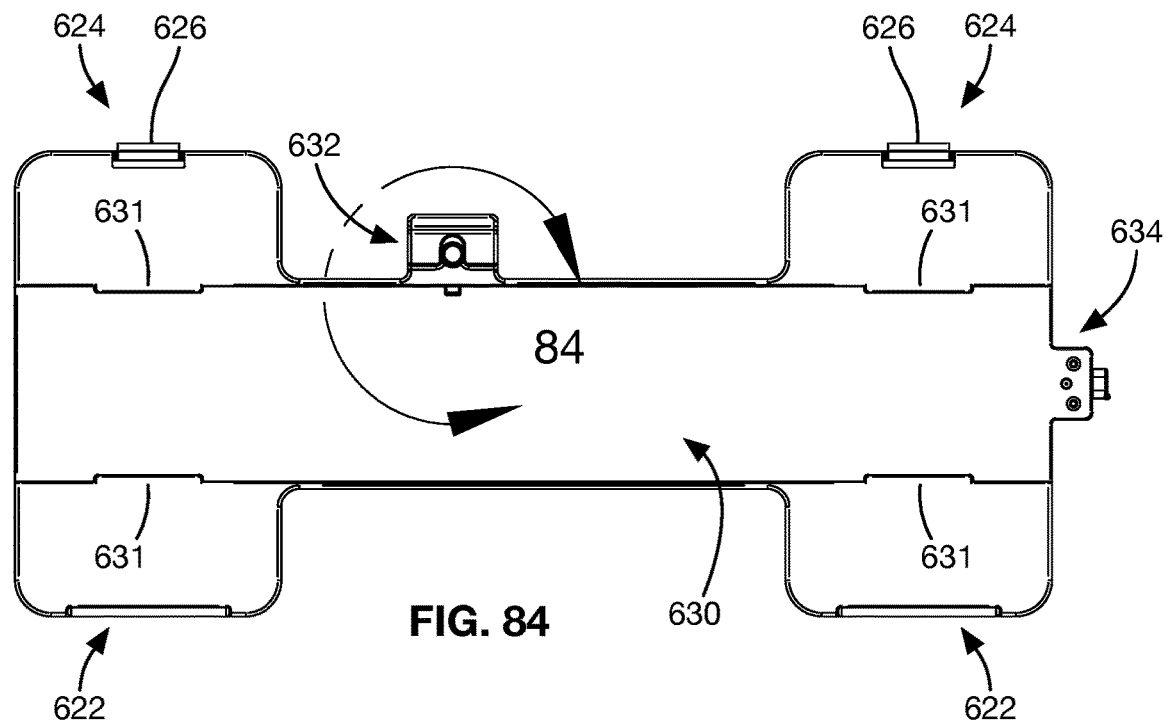
Figure 89:
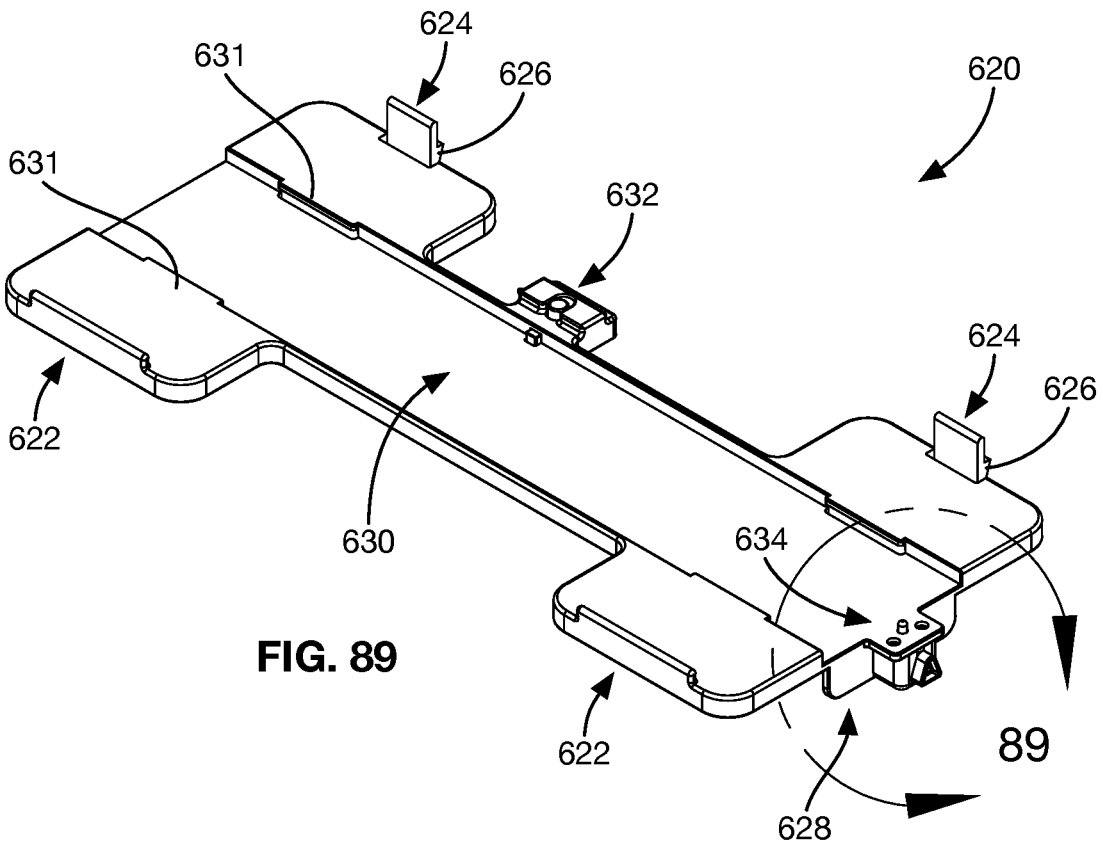
Figure 90:
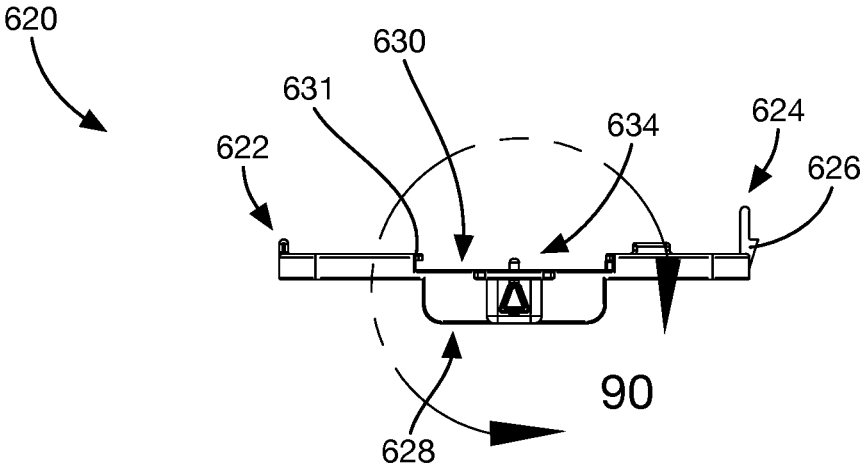

As is shown in FIGS. 81 and 82, in some implementations, the base plate 620 is assembled to the table 200 by first inserting the rigid tabs 622 underneath the latching protrusions 214 of one of the side walls 212 and moving the base plate 620 laterally to align the alignment tabs 628 on the ends of the table 200. The other side of the base plate 620 is then pressed downward so that the retention shoulders 626 of the flexible tabs 624 snap into the latching protrusions 214 of the opposite side wall 212 (FIGS. 77-80). The flexible tabs 624 can include a ramp or inclined portion to provide a smooth engagement with the latching protrusions 214.

In some implementations, to remove the base plate 620 from the table 200, the upper ends of the flexible tabs 624 are pressed inward until the shoulders 626 are released from beneath the latching protrusions 214 to enable the base plate 620 to be lifted upward and removed from the table 200. Sufficient space can be provided between the base plate 620 and table 200 so that a sterile barrier, such as a drape, can be provided between the two. That is, a sterile barrier can be laid on top of the table 200 before the base plate 620 is snapped into place between the side walls 212 of the table 200.

In some implementations, the base plate 620 is not configured to be assembled with more than one table 200. Rather, the carriage 640 of the stabilizing device 600 can be moved laterally along the base plate 620 and is also elongated sufficiently to receive two or more clamps 660.

In some implementations, the base plate 620 can be configured to be assembled or used with more than one table or a variety of tables or support surfaces. For example, the base plate can include one or more of a clamp(s), gripper(s), latch(es), keyed portions, interlocking portions, etc. In some implementations, one or more clamps or grippers can be configured to attach to a wide variety of tables or supports. For example, a clamp or clamps (or other grippers) can be arranged on the bottom and/or edges of the base plate that can be configured to slide or adjust to fit and clamp on different shapes and/or sizes of tables/supports.

In some implementations, the base plate 620 can include a mounting channel 630 for receiving and attaching to the carriage 640. In some implementations, retaining tabs 631 protrude into the channel 630 to engage and retain retaining edges or flanges 642 of the carriage 640 so that the carriage 640 is restrained to longitudinal movement along the mounting channel 630. The position of the carriage 640 within the mounting channel 630 can be locked in place by a side latch 632 (see FIGS. 85-88) and/or a bottom latch 634 (see FIGS. 91-94). That is, the side and bottom latches 632, 634 can be opened to allow the carriage 640 to slide relative to the base plate 620 and are closed to prohibit further movement of the carriage 640 within the mounting channel 630 of the base plate 620. The latches 632, 634 can be biased in a closed direction so that the latches 632, 634 close when an actuating or opening force is removed. Only one of the latches 632, 634 is needed to attach the carriage 640 to the base plate 620. Both latches 632, 634 are shown in the illustrated example to demonstrate the engagement of each of the latches 632, 634 with the carriage 640.

In some implementations, the carriage 640 can be formed in or as part of the base plate 620, e.g., such that the carriage is a carriage portion/feature of the base plate.

Referring now to FIGS. 83-94, example mechanisms of the side latch 632 and bottom latch 634 are shown in greater detail. In some implementations, the side latch 632 is operated by pressing outward on a cylindrical upper portion of the latch 632 that is arranged above and to one side of the mounting channel 630. As can be seen in FIGS. 83-86, in the closed condition, a latch member 636 of the side latch 632 protrudes into the mounting channel 630. When the side latch 632 is opened, as shown in FIGS. 87 and 88, the latch member 636 retracts into the base plate 620 and out of the mounting channel 630.

Figures 91, 93:
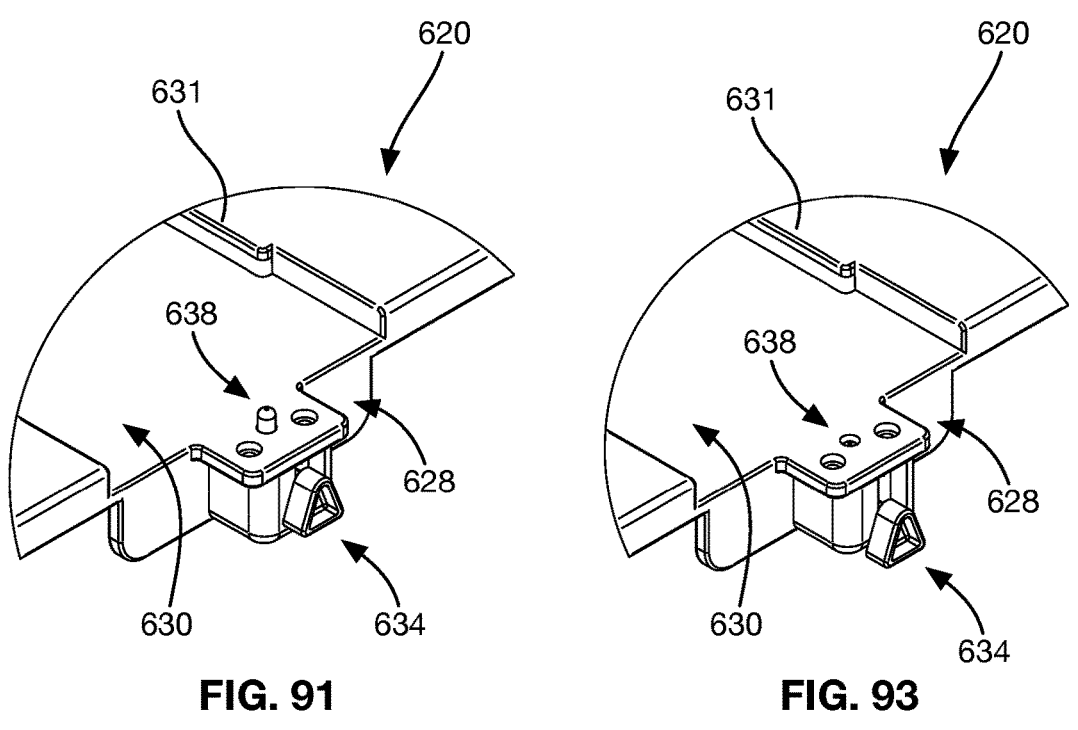
Figures 92, 94:
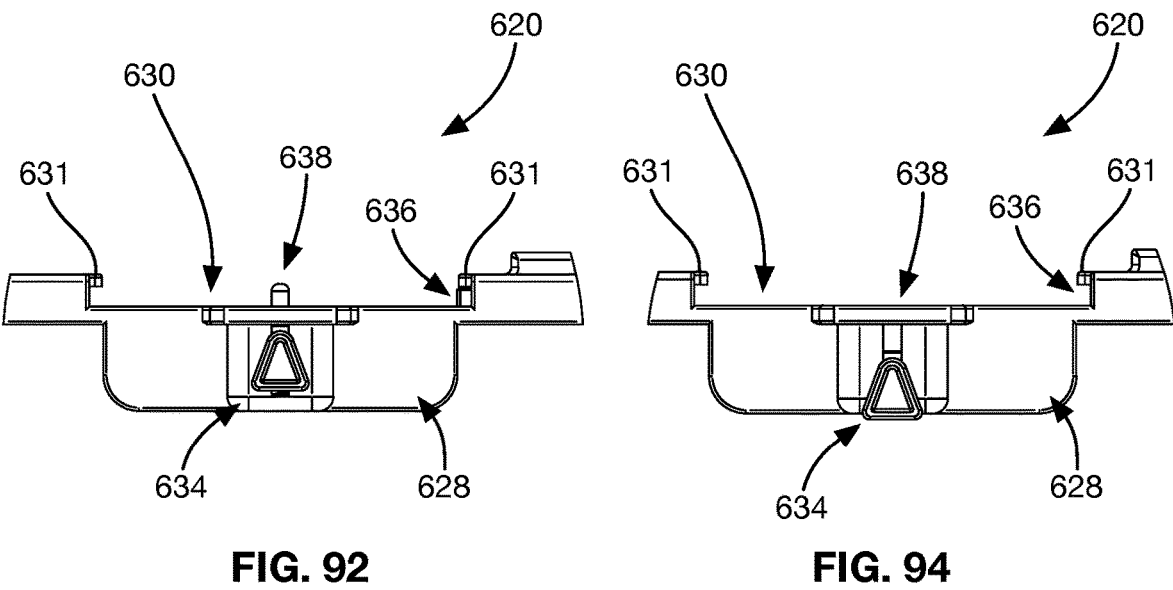

Referring to FIGS. 89-94, in some implementations, the bottom latch 634 is operated by pressing downward on an actuator, such as the illustrated triangle shaped portion, arranged at one end of the base plate 620 and below the mounting channel 630. As can be seen in FIGS. 89-92, in the closed condition, a latch pin 638 of the bottom latch 634 protrudes into the mounting channel 630. When the bottom latch 634 is opened, as shown in FIGS. 93 and 94, the latch pin 638 retracts into the base plate 620 and out of the mounting channel 630. Other arrangements are also possible.

Figures 95, 96, 97:
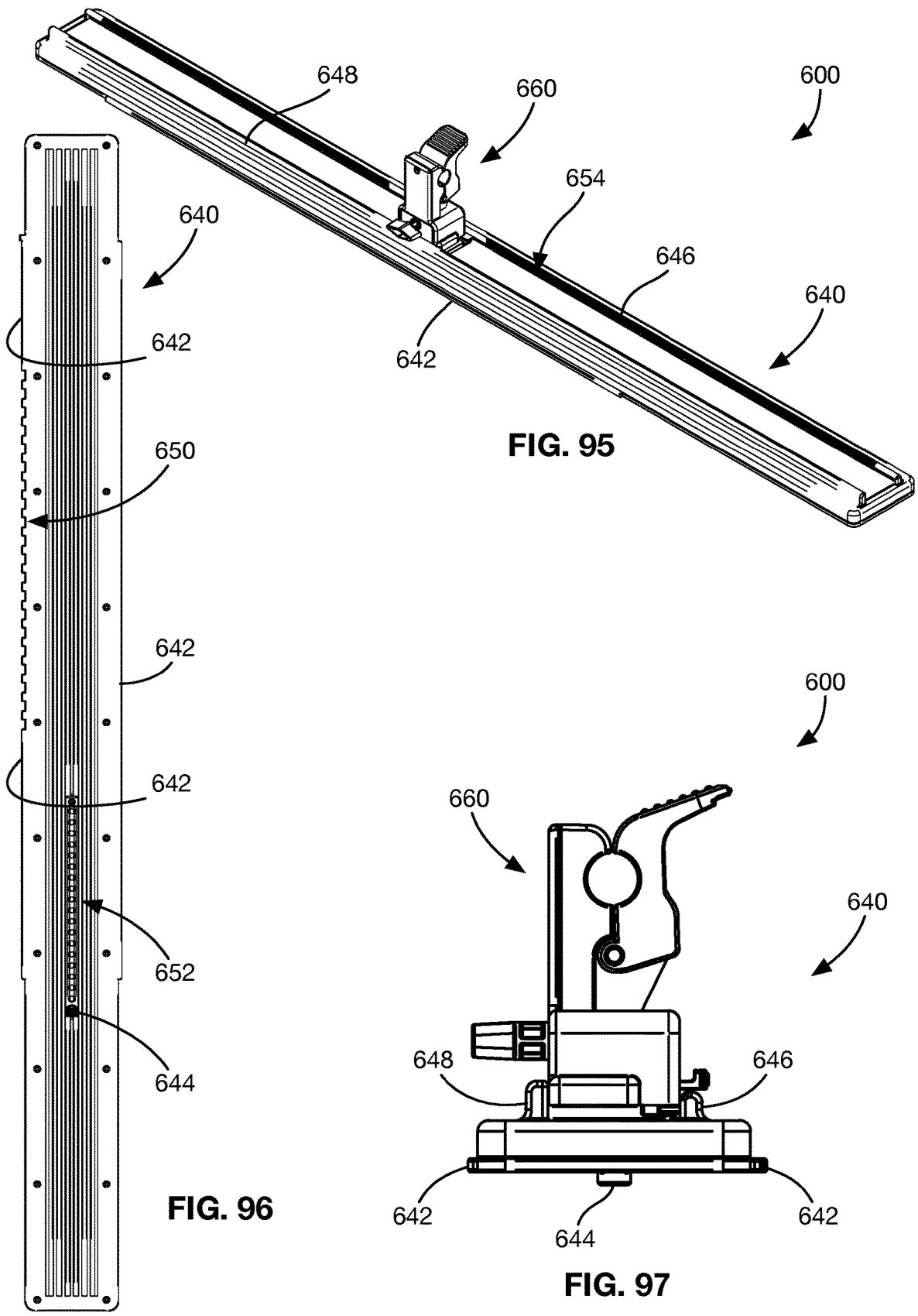
Figure 98:
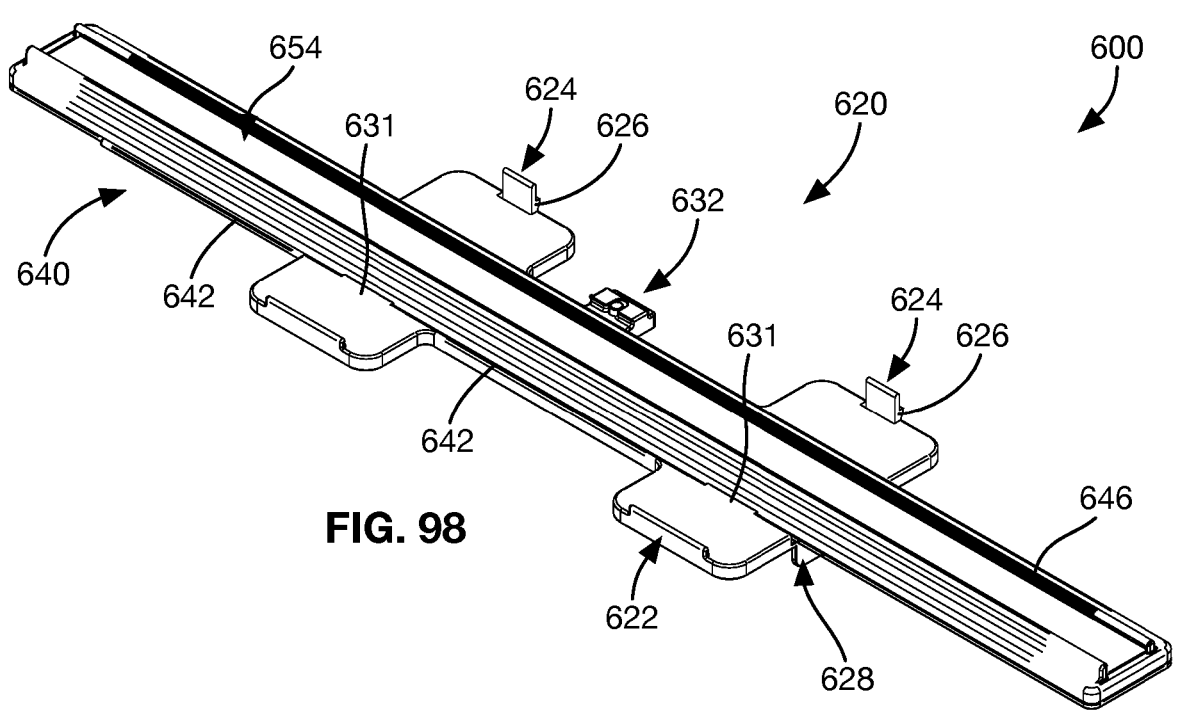
Figure 99:
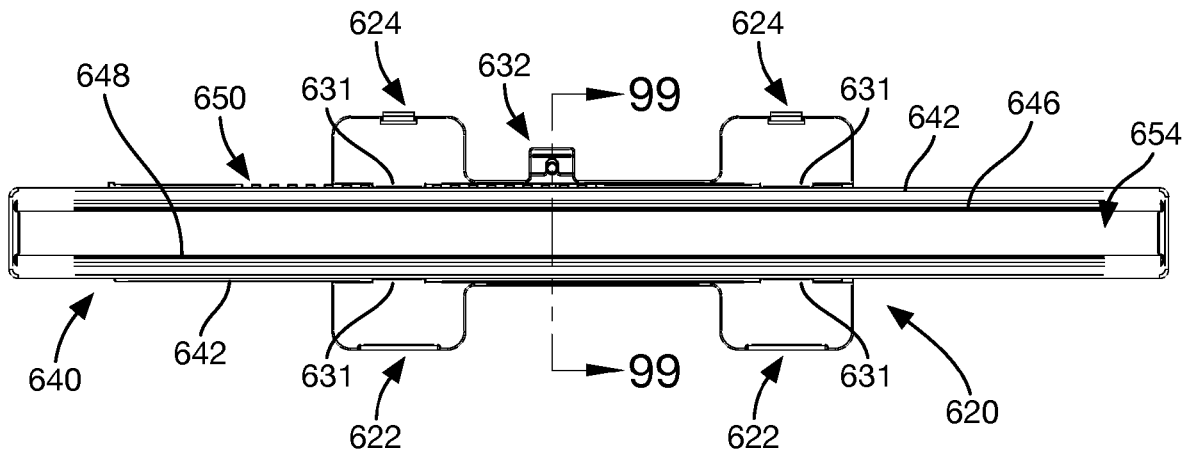
Figure 100:
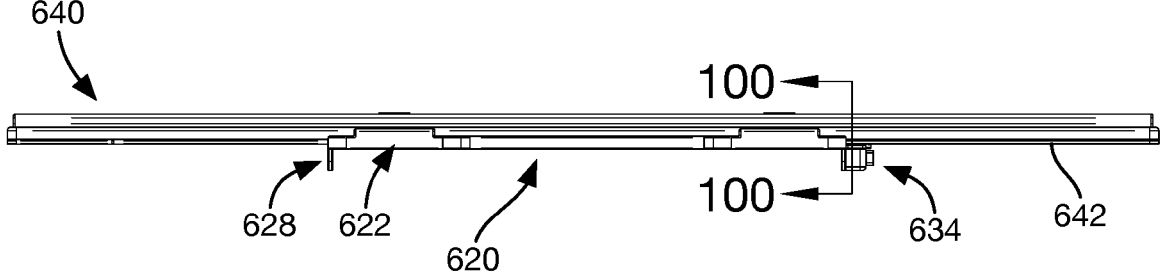
Figure 101:
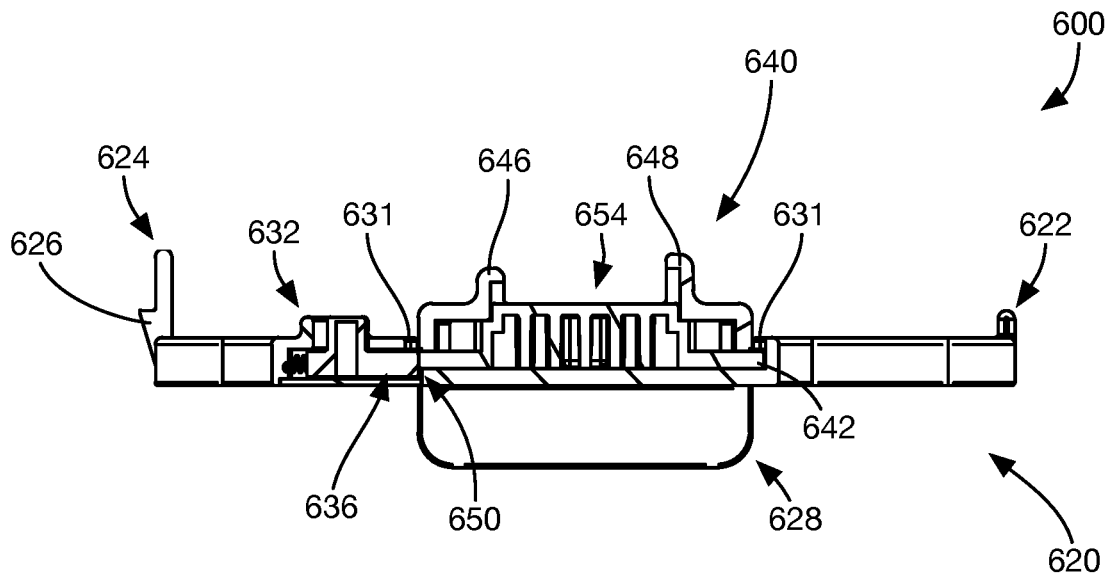

Referring now to FIG. 95, one clamp 660 is shown assembled to the carriage 640 (which can be a separate carriage or a carriage portion/feature of a base plate). In some implementations, first and second mounting rails 646 and 648 extend upward and define a clamp mounting channel 654 for holding and positioning one or more clamps 660, as is shown in FIG. 97.

In some implementations, the carriage can be configured to act as a base plate (e.g., as an integrated base plate and carriage portion), for example, the base plate can look and be configured to be similar to what is shown in FIGS. 95 and 96. In some implementations, the carriage can be configured to attach to a separate base plate. Referring to FIG. 96, in some implementations, the carriage can include one or more retaining edges or flanges 642 on both sides for engaging the retaining tabs 631 of the base plate 620.

Referring to FIGS. 95 and 96, in some implementations, an optional lateral stop 644 extends below the carriage 640 to prevent movement of the carriage 640 beyond a desired amount.

Referring now to FIGS. 98-102, the carriage 640 is shown combined with the base plate 620. In some implementations, the carriage is formed in or as part of, e.g., integral with, the base plate. In these implementations, the carriage (which can also be referred to as a carriage portion or carriage feature of the base plate) need not be movable relative to the base plate.

In some implementations, the carriage is held in place with side and bottom latches 632, 634. In some implementations, side positioning recesses 650 are arranged along one side of the carriage 640 and are configured to receive the latch member 636 of the side latch 632 of the base plate 620. The side positioning recesses 650 and side latch 632 enable an operator to slide and lock the carriage 640 in a desired position in the mounting channel 630 of the base plate 620. The latch member 636 engages one of the positioning recesses 650—as can be seen in the cross-sectional view of FIG. 101—to prohibit unwanted longitudinal movement of the carriage 640 relative to the base plate 620.

Figure 102:
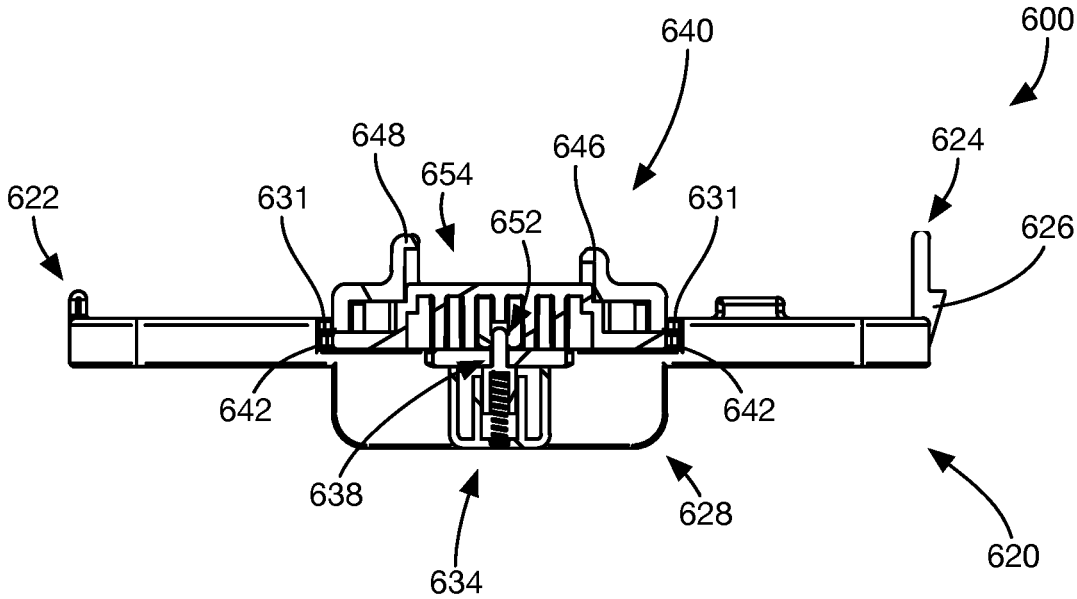

Referring to FIGS. 96 and 102, in some implementations, bottom positioning recesses 652 are also provided along the bottom of the carriage 640 leading up to the stop 644. The bottom positioning recesses 652 and bottom latch 634 enable an operator to slide and lock the carriage 640 in a desired position in the mounting channel 630 of the base plate 620. In some implementations, a latch pin 638 (or similar element) engages one of the bottom positioning recesses 652—as can be seen in the cross-sectional view of FIG. 102—to prohibit unwanted movement of the carriage 640 relative to the base plate 620. Thus, the movement of the carriage 640 relative to the base plate 620 is restrained in two locations to provide a secure and stabile connection for supporting the clamps 660.

Figures 103, 104:
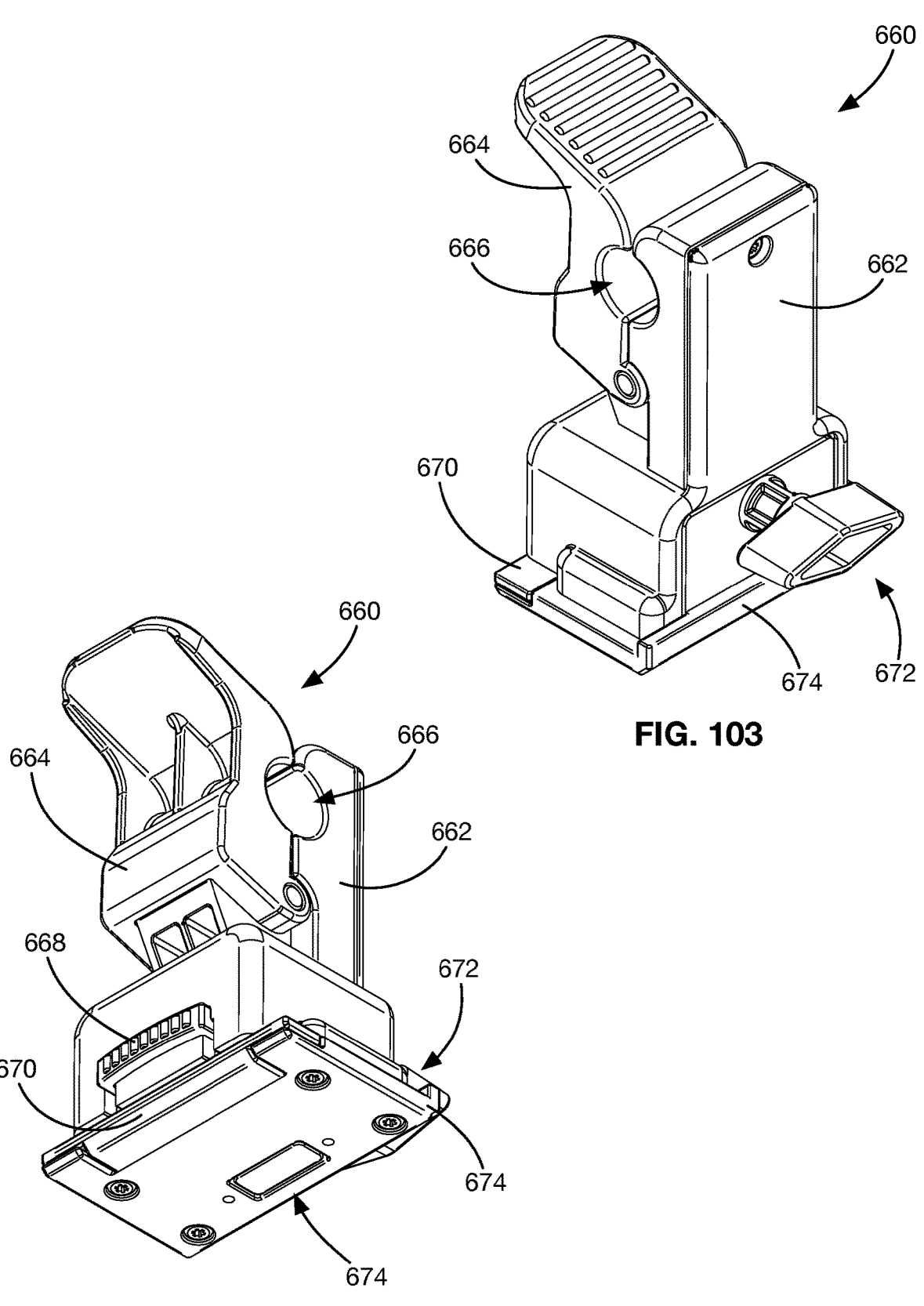

Referring now to FIGS. 103-116, an example clamp 660 and the mechanisms for attaching and positioning the clamp 660 on the carriage 640 are shown in greater detail. As can be seen in FIGS. 103 and 104, in some implementations, the clamp 660 includes a fixed jaw 662 and a movable jaw 664 that is opened and closed by pivoting the movable jaw 664 relative to the fixed jaw 662. The movable jaw 664 can be biased with a spring toward the fixed jaw 662 so that the clamp 660 remains in a closed condition unless opened by an application of an opening force to the movable jaw 664. The jaws 662, 664 of the clamp 660 come together to form an opening 666 for receiving the medical device (not shown), such as a catheter, to be stabilized by the stabilizing device 600. In the closed position, the fixed and movable jaws 662, 664 might remain spaced apart so that the closing force of the clamp 660 is applied to the medical device to stabilize and prohibit rotation of the medical device.

In some implementations, an actuator 668, such as a latch button or bar, on one side of the clamp 660, shown in greater detail in FIGS. 105-110, is operably connected to a movable retaining flange 670 that is configured to be received within a recess of the first mounting rail 646. In some implementations, a fixed retaining flange 674 extends from the side of the clamp 660 opposite the movable retaining flange 670 and is configured to be inserted into a recess of the second mounting rail 648 when assembling the clamp 660 to the carriage 640.

Referring to FIGS. 108-110, in some implementations, actuating an actuator, such as pressing on the latch button 668, retracts the movable retaining flange 670 so that the bottom of the clamp 660 can be inserted into the clamp mounting channel 654. In some implementations, the actuator or latch button 668 and movable retaining flange 670 are biased outward so that releasing pressure on the latch button moves the movable retaining flange 670 outward and into the recess of the first mounting rail 646. The movable retaining flange 670 can also include a beveled bottom edge so that the clamp 660 can be attached to the carriage 640 by inserting the fixed retaining flange 674 into the second mounting rail 648 and then pressing down on the clamp 660 to snap the clamp 660 onto the first mounting rail 646—that is, by causing the movable retaining flange 670 to open via the application of force against the inclined portion. Once the clamp is bottomed in the clamp mounting channel 654, the movable retaining flange 672 springs outward and engages the recess of the first mounting rail 646.

Figure 111:
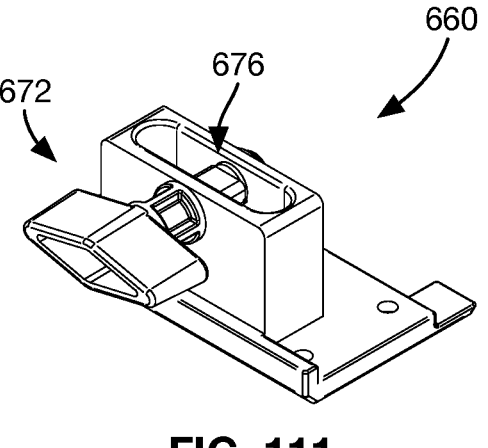
Figure 114:
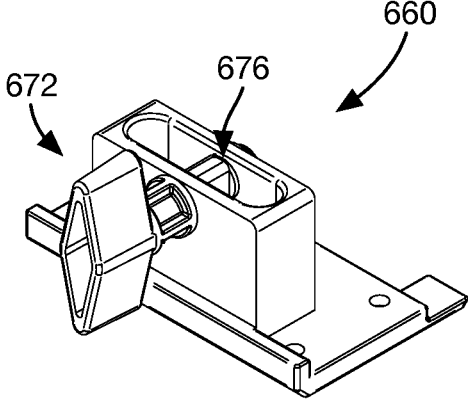
Figure 112:
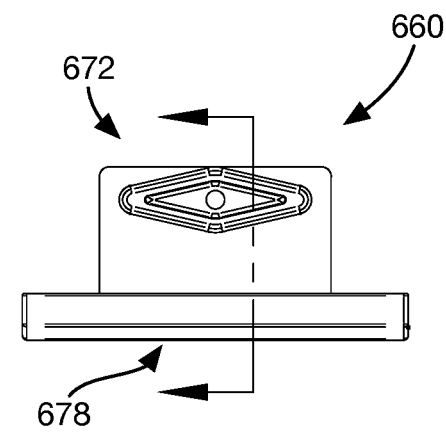
Figure 115:
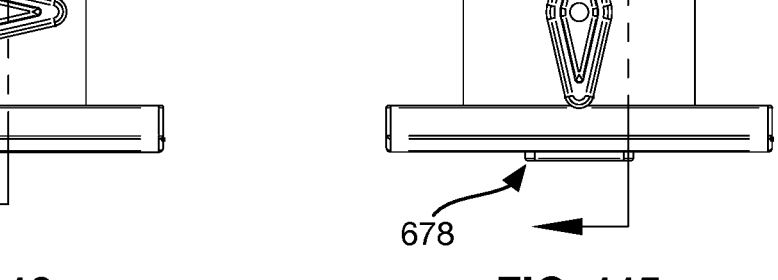
Figure 113:
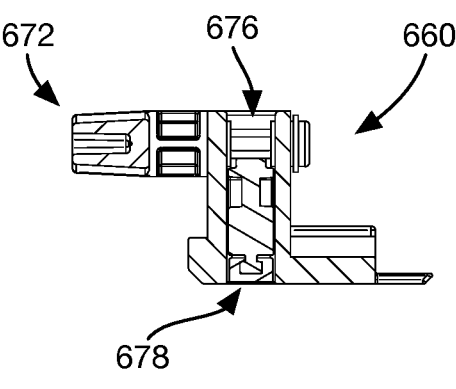
Figure 116:
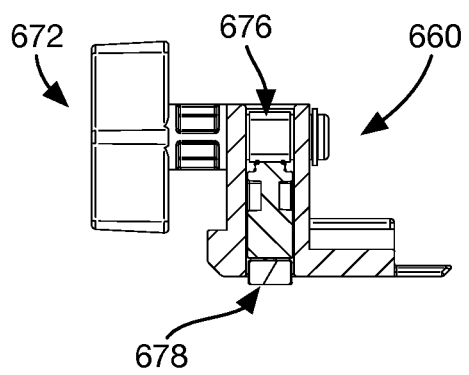

Once inserted into the clamp mounting channel 654, the clamp 660 can be freely moved (e.g., slid) along the length of the carriage 640 to a desired position. To hold the clamp 660 in a desired location, a locking knob 672 (or other actuator) can be rotated (or otherwise actuated) from a free slide position to a locked position. In some implementations, the locking knob 672 is connected to a rotating cam portion 676 so that rotating the locking knob 672 causes the rotating cam portion 676 to rotate. In some implementations, as the rotating cam portion 676 is rotated, an oblong portion of the rotating cam portion 676 engages a locking foot 678 (the term "foot" can refer to a variety of types of extensions of various sizes and shapes that can function similarly) and causes the locking foot 678 to move downward to an extended position (FIGS. 114-116). When the locking knob 672 is further rotated, or rotated in the reverse direction, the oblong portion of the rotating cam portion 676 allows the locking foot 678 to move upward to return to a retracted position (FIGS. 111-113). In some implementations, the locking foot 678 includes a biasing member, such as a spring, so that the locking foot 678 remains in the retracted position until the locking knob 672 is actuated. Other mechanisms to accomplish similar results can also be used. For example, in some implementations, one or more of gears, worm gears, pulleys, levers, motors, etc. can be used to extend or retract the foot 678.

When the clamp 660 has been moved along the clamp mounting channel 654 to a desired position, the locking knob 672 can be actuated to extend the locking foot 678. In some implementations, the locking foot 678 presses down on the bottom of the clamp mounting channel 654 and, consequently, causes the movable and fixed retaining flanges 670, 674 to move upward to engage the top surface of the recesses in the first and second mounting rails 646, 648, respectively. The friction generated between the locking foot 678 and the clamp mounting channel 654 and between the retaining flanges 670, 674 and the mounting rails 646, 648 retain the clamp 660 in the desired location. To reposition the clamp 660, the locking knob 672 can be rotated to disengage the locking foot 678 so that the clamp 660 can slide along the channel. If another clamp 660 is in the way, the latch button 668 (or another similar actuator) can be pressed (or actuated) and the clamp removed from the clamp mounting channel 654 altogether and placed back into the channel 654 in another location. Thus, the stabilizer 600 can be easily adjusted or configured for use with various medical devices.

Figures 117, 118, 119:
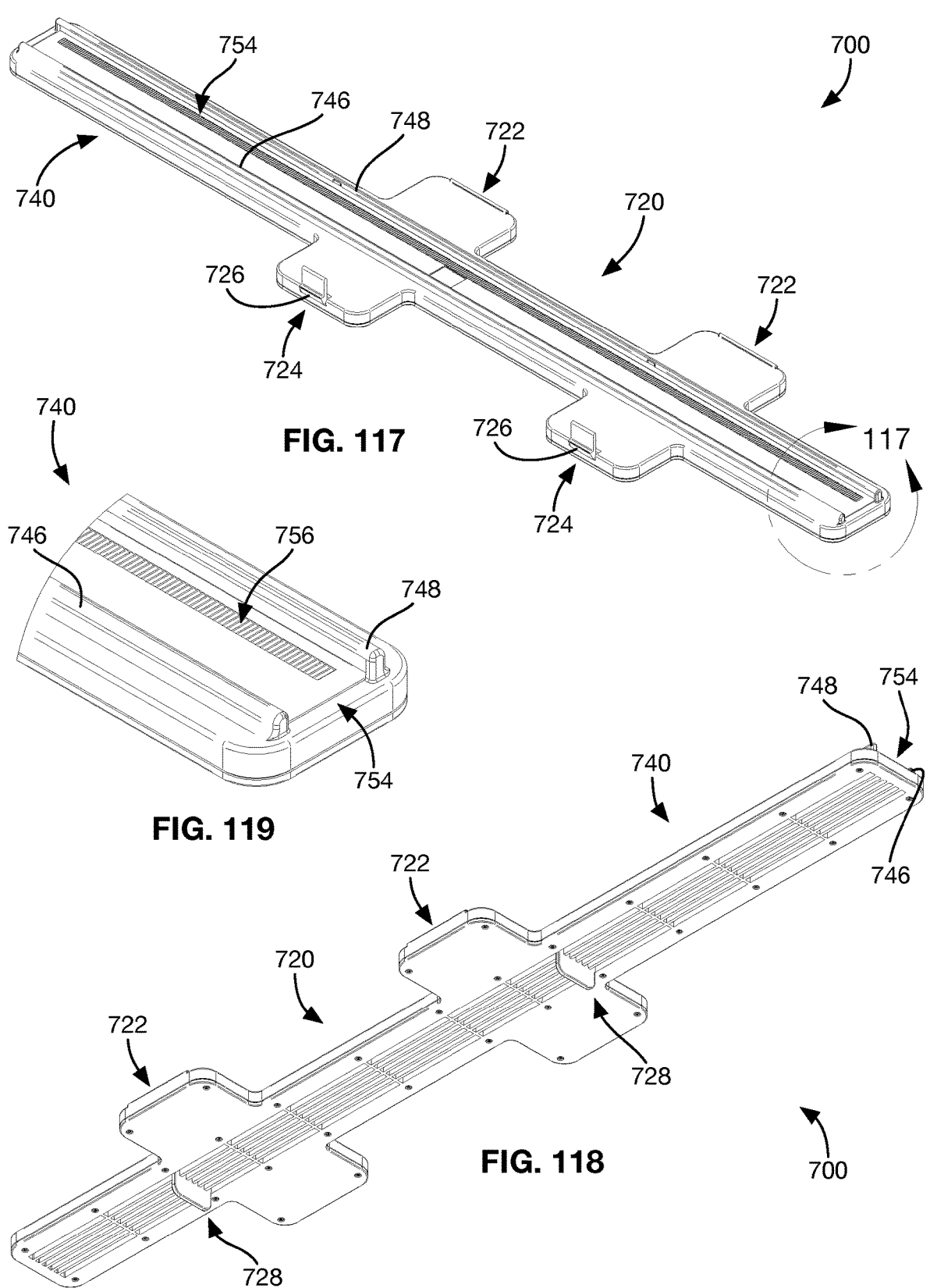
FIGS. 117-119 show various views of an example of an integrally formed baseplate and carriage of a stabilizer for holding a delivery device used to implant an implantable prosthetic.

Any of the components of the stabilizing devices described herein can be integrally formed as a single component. For example, a stabilizing device 700 can include any of the features of any of the baseplates disclosed herein integrally formed with any of the features of any of the carriages disclosed herein. For example, as can be seen in FIGS. 117-119, an example of a stabilizing device 700 can be integrally formed and include features of the baseplate 620 and features of the carriage 640. The stabilizing device 700 can include the features of the baseplate 620 that facilitate connection and/or adjustment of the stabilizing device to a platform, such as the platform 210 disclosed herein. The stabilizing device 700 can include the features of the carriage 640 that facilitate connection and/or adjustment of the clamp(s), such as the clamp(s) 660, to the stabilizing device. The features that facilitate connection of the baseplate 620 and the carriage 640 are eliminated, since the baseplate 620 and the carriage 640 are integrally formed. The device 700 can otherwise be the same as or similar to the device 600, but with an integrally formed base plate portion 720 and a clamp attachment portion 740 that replaces the features of the movable carriage portion 640.

In some implementations, the base plate need not include portions extending from the sides thereof. For example, the base plate can instead be an integral base plate and carriage portion that looks similar to what is shown in FIGS. 95 and 96. In some implementations, the carriage shown in FIGS. 95 and 96 acts as the base plate and can attach to (e.g., as described below) or be placed directly on a table or other support surface.

The system can include a table to which the base plate can be attached or placed thereon. In some implementations, the base plate portion 720 attaches to the table 200 in the same manner as the base plate 620, described above. For example, the base plate portion 720 can include rigid tabs 722 and spring or flexible tabs 724 including retention shoulders 726. In some implementations, alignment tabs 728 extend below the base plate portion 720 to engage the ends of the table (not shown) so that the base plate portion 720 is properly arranged on the table and is prohibited from moving laterally on the table.

Other ways of sitting on or attaching to a table or support are also possible, which need not include any of tabs 722, tabs 724, tabs 728, or shoulders 726. In some implementations, the base plate portion 720 can include one or more different types of attachments means. For example, the base plate portion can include one or more of a clamp(s), gripper(s), latch(es), keyed portions, interlocking portions, etc. In some implementations, one or more clamps or grippers can be configured to attach to a wide variety of tables and/or support surfaces. For example, a clamp or clamps (or other grippers) can be arranged on the bottom and/or edges of the base plate that can be configured to slide or adjust to fit and clamp on different shapes and/or sizes of tables/support surfaces. In some implementations, one or more extensions similar to one of tabs 728 (but these can be different shapes, sizes, and designs, e.g., potentially one or more of longer, wider, contoured to fit with an edge of a table, etc.) can be positioned on the bottom of the base plate to act as one or more sides of a clamp or gripper that can be adjusted to grip or attach the base plate to a variety of different tables/supports of different sizes and shapes. In some implementations, one extension from the bottom of the base plate (which can be similar to one of tabs 728 but configured to interact with a side of a table) can remain stationary relative to the base plate, and another extension from the bottom of the base plate can be movable/slidable relative to the base plate and configured to interact with a side of a table/support, such that the two extensions act as a clamp or gripper that can be adjusted to different sized tables/supports and moved into tight contact with the sides of the table/ support to hold the base plate in position on the table/support. The table/support can include one or more legs and include one or more features of other tables herein.

The clamp attachment portion 740 is similar to the carriage 640 and includes first and second mounting rails 746 and 748 that extend upward and define a clamp mounting channel 754 for holding and positioning one or more clamps 660. In some implementations, the clamp mounting channel 754 includes a friction or gripping strip 756 for engaging the locking foot 678 of the one or more clamps 660.

While various inventive aspects, concepts and features of the disclosures may be described and illustrated herein as embodied in combination in the examples herein, these various aspects, concepts, and features may be used in many alternative examples, either individually or in various combinations and sub-combinations thereof. Unless expressly excluded herein all such combinations and sub-combinations are intended to be within the scope of the present application. Still further, while various alternative examples as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative examples, whether presently known or later developed. Those skilled in the art may readily adopt one or more of the inventive aspects, concepts, or features into additional examples and uses within the scope of the present application even if such examples are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. The words used in the claims have their full ordinary meanings and are not limited in any way by the description of the examples in the specification.

What is claimed is:

1. A stabilizing system for holding a medical device comprising:
   a clamp mounting channel comprising first and second mounting rails;
   a clamp for receiving the medical device, wherein the clamp is slidably disposed in the clamp mounting channel;
   wherein the clamp includes:
      a foot;
      a locking actuator movable from a free slide position to a locked position;

a cam portion connected to the locking actuator; and
wherein moving the locking actuator from the free slide position to the locked position moves the cam portion to engage the foot and cause the foot to move away from the locking actuator to engage the clamp mounting channel to lock a position of the clamp in the clamp mounting channel.

2. The stabilizing system of claim 1 wherein the clamp mounting channel comprises a gripping strip for engaging the foot.

3. The stabilizing system of claim 1 wherein the clamp includes a fixed mounting flange and a movable mounting flange.

4. The stabilizing system of claim 3 wherein the fixed mounting flange and the movable mounting flange are disposable in recesses in the first and second mounting rails.

5. The stabilizing system of claim 4 further comprising a mounting flange actuator that is actuatable to retract the movable mounting flange.

6. The stabilizing system of claim 3 wherein the movable mounting flange is biased away from the fixed mounting flange.

7. The stabilizing system of claim 1 wherein the foot is biased to a retracted position.

8. The stabilizing system of claim 1 wherein the clamp comprises a fixed jaw and a movable jaw that is biased in a closing direction toward the fixed jaw.

9. A stabilizing system for holding a medical device comprising:
   a base plate having a clamp mounting channel;
   a clamp for receiving the medical device, wherein the clamp is slidably disposed in the clamp mounting channel, the clamp comprising:
      a foot;
      a locking actuator movable from a free slide position to a locked position;
      a cam portion connected to the locking actuator; and
      wherein moving the locking actuator from the free slide position to the locked position moves the cam portion to engage the foot and cause the foot to move away from the locking actuator to engage the base plate to lock a position of the clamp in the clamp mounting channel.

10. The stabilizing system of claim 9, wherein the clamp comprises a pair of jaws.

11. The stabilizing system of claim 9 wherein moving the locking actuator from the locked position to the free slide position moves the cam portion to engage the foot and cause the foot to move upward to disengage the base plate.

12. The stabilizing system of claim 9 wherein the locking actuator is a rotatable locking knob.

13. The stabilizing system of claim 9 wherein the cam portion is a rotating cam portion.

14. The stabilizing system of claim 9 wherein the foot is biased to a retracted position.

15. A stabilizing system for holding a medical device comprising:
   a base plate;
   a clamp for receiving the medical device, wherein the clamp is slidably coupled to the base plate, the clamp comprising:
      a foot;
      a knob rotatable from a free slide position to a locked position;
      a cam portion connected to the knob; and
      wherein rotating the knob from the free slide position to the locked position rotates the cam portion to engage the foot and cause the foot to move away from the knob to engage the base plate to lock a position of the clamp.

16. The stabilizing system of claim 15 wherein a portion of the clamp is disposed in a channel of the base plate.

17. The stabilizing system of claim 15, wherein the clamp comprises a pair of jaws.

18. The stabilizing system of claim 15 wherein rotating the knob from the locked position to the free slide position rotates the cam portion to engage the foot and cause the foot to move upward to disengage the base plate.

19. The stabilizing system of claim 15 wherein the foot is biased to a retracted position.

\* \* \* \* \*